(12) United States Patent
Jirousek et al.

(10) Patent No.: US 6,410,562 B1
(45) Date of Patent: Jun. 25, 2002

(54) HYPOGLYCEMIC IMIDAZOLINE COMPOUNDS

(75) Inventors: Michael R. Jirousek, Antioch, IL (US); Michael Paal; Gerd Ruhter, both of Hamburg (DE); Theo Schotten, Vierhufen (DE); Kumiko Takeuchi, Indianapolis, IN (US); Wolfgang Stenzel, Reinbek (DE)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/581,498

(22) PCT Filed: Dec. 18, 1998

(86) PCT No.: PCT/US98/27080

§ 371 (c)(1),
(2), (4) Date: Dec. 8, 2001

(87) PCT Pub. No.: WO99/32482

PCT Pub. Date: Jul. 1, 1999

(51) Int. Cl.[7] .................. A61K 31/47; A61K 31/425; C07D 215/12; C07D 277/04; C07D 403/02

(52) U.S. Cl. .................. 514/314; 514/365; 514/374; 514/396; 514/401; 546/176; 546/177; 548/146; 548/237; 548/312.1; 548/355.1

(58) Field of Search ................... 546/176, 177; 548/146, 237, 312.1, 355.1; 514/314, 365, 374, 396, 401

(56) References Cited

U.S. PATENT DOCUMENTS

| | | | |
|---|---|---|---|
| 2,161,938 A | 6/1939 | Sonn | 260/309 |
| 2,731,471 A | 1/1956 | Synerholm et al. | 548/347.1 X |
| 2,751,393 A | 6/1956 | Schindler et al. | 548/312.1 |
| 2,824,120 A | 2/1958 | Buckley, Jr. et al. | 548/347.1 X |
| 2,890,984 A | 6/1959 | Sahyun | 548/347.1 X |
| 2,899,441 A | 8/1959 | Dornfeld | 260/309.6 |
| 2,948,724 A | 8/1960 | Sahyun et al. | 548/347.1 X |
| 3,287,469 A | 11/1966 | Harvey | 260/309.6 |
| 3,354,175 A | 11/1967 | Fruhstorfer et al. | 548/354.1 X |
| 3,586,695 A | 6/1971 | Wysong et al. | 260/309.6 |
| 3,649,640 A | 3/1972 | Sulkowski et al. | 260/309.6 |
| 3,992,403 A | 11/1976 | Roebke | 260/309.6 |
| 4,539,410 A | 9/1985 | Renfroe | 548/336 |
| 4,659,731 A | 4/1987 | Bigg et al. | 514/397 |
| 4,912,125 A | 3/1990 | Huebner et al. | 514/402 |
| 5,017,584 A | 5/1991 | Hlasta | 514/314 |
| 5,206,332 A | 4/1993 | Hammer et al. | 528/118 |
| 5,614,520 A | 3/1997 | Kondo et al. | 514/236.8 |
| 5,866,579 A | 2/1999 | Wong et al. | 514/259 |

FOREIGN PATENT DOCUMENTS

| | | |
|---|---|---|
| CA | 2121917 | * 10/1994 |
| CH | 204 738 | 5/1939 |
| CH | 204 739 | 5/1939 |
| DE | 3 830 419 | 3/1989 |
| EP | 001 647 | 5/1979 |
| EP | 028 410 | 5/1981 |
| EP | 125 410 | 11/1984 |
| EP | 266 532 | 9/1987 |
| EP | 534 258 | 9/1992 |
| EP | 585116 | * 3/1994 |
| FR | 793 708 | 1/1936 |
| GB | 591 683 | 8/1947 |
| GB | 1 152 920 | 5/1969 |
| GB | 1 170 841 | 11/1969 |
| GB | 2 209 748 | 5/1989 |
| JP | 06-336429 | * 12/1994 |
| JP | 07-304669 | * 11/1995 |
| NL | 7 605 609 | 5/1975 |
| SU | 480 708 | 8/1975 |
| WO | WO 91/00862 | 1/1991 |
| WO | 91-17149 | * 11/1991 |
| WO | WO 92/05171 | 4/1992 |
| WO | WO 92/06972 | 4/1992 |
| WO | WO 93/09113 | 5/1993 |
| WO | WO 97/27181 | 7/1997 |

OTHER PUBLICATIONS

Leighton, CA 123:144331, 1995.*
Chau, CA 125:248175, 1996.*
Shafer, CA 124:260953, 1996.*
Shimano, CA 124:87710, 1995.*
Andrus, CA 128:48160, 1997.*
Puts, CA 127:34173, 1997.*
Ruzinsky, CA 128:243984, 1997.*
Amin, CA 120:144354, 1994.*
Chemical Abstracts, vol. 93, 1980, p. 636.
Chemical Abstracts (28–Heterocycles), vol. 95, 1981, p. 729.
Chemical Abstracts, vol. 96, 1982, p. 604.
Chemical Abstracts (28–Heterocycles), vol. 119, 1993, p. 925.
Chemical Abstracts (28–Heterocycles), vol. 120, 1994, p. 871.

* cited by examiner

*Primary Examiner*—D. Margaret Seaman
(74) *Attorney, Agent, or Firm*—MaCharri Vorndran-Jones; Paul Darkes

(57) ABSTRACT

This invention relates to certain novel imidazoline compounds and analogues thereof, to their use for the treatment of diabetes, diabetic complications, metabolic disorders, or related diseases where impaired glucose disposal is present, to pharmaceutical compositions comprising them, and to processes for their preparation.

38 Claims, No Drawings

HYPOGLYCEMIC IMIDAZOLINE COMPOUNDS

This application is a 371 of PCT/US98/27080, filed Dec. 18, 1998.

FIELD OF THE INVENTION

This invention relates to certain novel imidazoline compounds and analogues thereof, to their use for the treatment of diabetes, diabetic complications, metabolic disorders, or related diseases where impaired glucose disposal is present, to pharmaceutical compositions comprising them, and to processes for their preparation.

BACKGROUND OF THE INVENTION

It is generally accepted that the control of blood glucose levels for the treatment of patients diagnosed with type II diabetes will have a beneficial effect. Established oral therapies for treating type II diabetes either improve insulin action or cause enhanced insulin secretion. The agents currently approved as therapies for type II diabetes patients that cause an enhanced insulin secretion contain a sulphonlyurea moiety. These compounds act by depolarising the beta cell by modulating closure of the K-ATP channel. Additional compounds that act at the K-ATP channel are under consideration for treatment of type II diabetes and that are not sulphonylurea compounds and have a fast onset of activity and short duration of action such as (−)-N-(trans4-isopropylcyclohexanecarbonyl)-D-phenylalanine (A-4166) (*Brit. J. Pharm.* 1997,120,137–145).

All agents that function at the molecular level by modulating the K-ATP channel have the potential for inducing hypoglycemia. Hypoglycemia is the major cause of adverse reactions in patients receiving sulphonylurea therapy and the prevalence of hypoglycemic episodes can be as high as 20% of patients. Compounds that potentiate insulin secretion under high glucose conditions and have little or no effect at low blood glucose levels would offer a distinct advantage in the treatment of type II diabetes.

SUMMARY OF THE INVENTION

Compounds of the present invention potentiate the secretion of insulin from beta cells under high glucose conditions and have minimal effect under low glucose conditions.

The compounds are also operable in additional disease states where impaired glucose disposal is present. For example, these include cardiovascular disease where above normal glucose levels are present or initial insulin resistance has occurred. The compounds can also be used to treat post operative insulin resistance induced by anaesthesia.

The present invention provides compounds of the following Formula (I), and the use of said compounds in the treatment of diabetes, especially Type II diabetes, diabetic complications, and metabolic disorders or related diseases in particular where impaired glucose disposal is present.

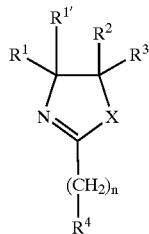

(I)

wherein

X is —O—, —S—, or —NR$^5$—;

R$^5$ is hydrogen, C$_{1-8}$ alkyl, or an amino protecting group,

R$^1$, R$^{1'}$, R$^2$, and R$^3$ are independently hydrogen or C$_{1-8}$ alkyl;

R$^1$ and R$^2$ optionally together form a bond and R$^{1'}$ and R$^3$ are independently hydrogen or C$_{1-8}$ alkyl;

R$^1$ and R$^2$ optionally combine together with the carbon atoms to which they are attached form a C$_{3-7}$ carbocyclic ring and R$^{1'}$ and R$^3$ are independently hydrogen or C$_{1-8}$ alkyl;

R$^1$ and R$^{1'}$ together with the carbon atom to which they are attached optionally combine to form a C$_{3-7}$ spirocarbocyclic ring and R$^2$ and R$^3$ are independently hydrogen or C$_{1-8}$ alkyl;

R$^2$ and R$^3$ together with the carbon atom to which they are attached optionally combine to form a C$_{3-7}$ spirocarbocyclic and R$^1$ and R$^{1'}$ are independently hydrogen or C$_{1-8}$ alkyl;

n is 0, 1, or 2;

m is 0, 1 or 2;

m' is 0, 1, or 2;

q' is 0,1,2,3,4, or 5;

R$^4$ is

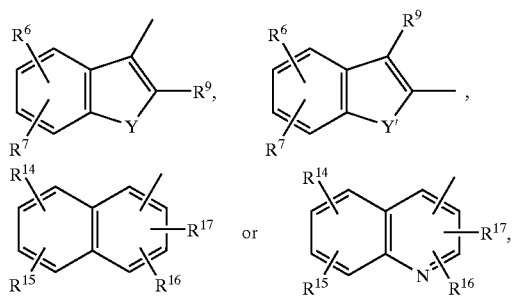

Y is —O—, —S—, or —NR$^8$—;

Y' is —O— or —S—;

R$^6$ and R$^7$ are independently hydrogen, C$_{1-8}$ alkyl, C$_{3-7}$ cycloalkyl, C$_{1-8}$ alkoxy, C$_{1-8}$ alkylthio, halo C$_{1-8}$ alkylthio, C$_{1-8}$ alkylsulfinyl, C$_{1-8}$ alkylsulfonyl, C$_{3-7}$ cycloalkoxy, aryl-C$_{1-8}$ alkoxy, halo, halo-C$_{1-8}$ alkyl, halo-C$_{1-8}$ alkoxy, nitro, —NR$^{10}$R$^{11}$, —CONR$^{10}$R$^{11}$, aryl C$_{1-8}$ alkyl, optionally substituted heterocyclyl, optionally substituted phenyl, optionally substituted naphthyl, optionally halo substituted acylamino, cyano, hydroxy, COR$^{12}$, halo C$_{1-8}$ alkylsulfinyl, or halo C$_{1-8}$ alkylsulfonyl, or alkoxyalkyl of the formula CH$_3$(CH$_2$)$_p$—O—(CH$_2$)$_q$—O—;

where p is 0, 1, 2, 3, or 4; and
q is 1, 2, 3, 4, or 5;
$R^{12}$ is $C_{1-8}$ alkyl or optionally substituted phenyl;
$R^8$ is hydrogen, $C_{1-8}$ alkyl, halo-$C_{1-8}$ alkyl, optionally substituted phenyl, optionally substituted heterocyclyl, COO $C_{1-8}$ alkyl, optionally substituted COaryl, COC$_{1-8}$ alkyl, SO$_2$C$_{1-8}$ alkyl, optionally substituted SO$_2$ aryl, optionally substituted phenyl-$C_{1-8}$ alkyl, $CH_3(CH_2)_p$—O—$(CH_2)_q$—O—;
$R^9$ is hydrogen, halo, $C_{1-8}$ alkyl, halo $C_{1-8}$ alkyl, $C_{1-8}$ alkylthio, halo $C_{1-8}$ alkylthio, $C_{3-7}$ cycloalkylthio, optionally substituted arylthio or heteroarylthio, $C_{1-8}$ alkoxy, $C_{3-7}$ cycloalkoxy, optionally substituted aryloxy, optionally substituted heteroaryloxy, or optionally substituted aryl or heteroaryl, $C_{3-7}$ cycloalkyl, halo $C_{3-7}$ cycloalkyl, $C_{3-7}$ cycloalkenyl, cyano, COOR$^{10}$, CONR$^{10}$R$^{11}$ or NR$^{10}$R$^{11}$, $C_{2-6}$ alkenyl, optionally substituted heterocyclyl, optionally substituted aryl $C_{1-8}$ alkyl, optionally substituted heteroaryl $C_{1-8}$ alkyl in which the alkyl group can be substituted by hydroxy, or $C_{1-8}$ alkyl substituted by hydroxy,
$R^{10}$ and $R^{11}$ are independently hydrogen, $C_{1-8}$ alkyl, optionally substituted aryl $C_{1-8}$ alkyl, optionally substituted phenyl, or $R^{10}$ and $R^{11}$ together with the nitrogen atom to which they are attached may combine to form a ring with up to six carbon atoms which optionally may be substituted with up to two $C_{1-8}$ alkyl groups or one carbon atom may be replaced by oxygen or sulfur;
$R^{14}$ and $R^{16}$ are independently hydrogen, halo, $C_{1-8}$ alkyl, $C_{3-7}$ cycloalkyl, $C_{3-7}$ cycloalkoxy, $C_{3-7}$ cycloalkylC$_{1-8}$ alkoxy, halo-$C_{1-8}$ alkyl, halo-$C_{1-8}$ alkoxy, $C_{1-8}$ alkoxy, carbo($C_{1-8}$)alkoxy, optionally substituted aryl, or optionally substituted heteroaryl;
$R^{15}$ and $R^{17}$ are independently hydrogen, halo, $C_{1-8}$ alkoxy, $C_{3-7}$-cycloalkyl, $C_{3-7}$ cycloalkylC$_{1-8}$ alkoxy, $C_{1-8}$ alkyl, $C_{3-7}$ cycloalkoxy, hydroxy, halo $C_{1-8}$ alkoxy, carbo($C_{1-8}$)alkoxy, optionally substituted phenyl, optionally substituted phenyl-$C_{1-8}$ alkyl, optionally substituted phenyloxy, optionally substituted phenyl-$C_{1-8}$ alkoxy, (tetrahydropyran-2-yl)methoxy, $C_{1-8}$ alkyl-S(O)$_m$—, optionally substituted aryl-$C_{1-8}$ alkyl-S(O)$_m$—, $CH_3(CH_2)_p$—Z$^1$—(CH$_2$)$_q$—Z$^2$—, or Z$^3$—(CH$_2$)$_q'$—Z$^2$—;
$Z^1$ and $Z^2$ are independently a bond, O, S, SO, SO$_2$, sulphoximino, or NR$^{10}$;
$Z^3$ is hydroxy, protected hydroxy, NR$^{10}$ R$^{11}$, protected amino, SH or protected SH;
provided that when $R^1$, $R^{1'}$, $R^2$ and $R^3$ are all hydrogen; n is 0; $R^4$ is naphthyl; and $R^{14}$, $R^{15}$ and $R^{16}$, or $R^{15}$, $R^{16}$ and $R^{17}$ are all hydrogen, then $R^{17}$ or $R^{14}$, respectively, is other than halo, methoxy, or C1–6 alkyl.
and pharmaceutically acceptable salts and esters thereof.

One embodiment of the present invention is the use of a compound of formula (I), or a pharmaceutically acceptable salt or ester thereof, in the manufacture of a medicament for treating diabetes or a related disorder.

Another embodiment of the present invention is a method of treating diabetes or a related disorder, which comprises administering to a patient a compound of formula (I), or a pharmaceutically acceptable salt thereof.

DETAILED DESCRIPTION OF THE INVENTION

In the above formulae, a "$C_{1-8}$ alkyl" group can be any alkyl group, branched or unbranched, containing up to eight carbon atoms, and examples include methyl, ethyl, propyl, isopropyl, butyl, isobutyl, tertiary butyl, pentyl and hexyl. Preferred values of $C_{1-8}$ alkyl are $C_{1-6}$ alkyl, and most preferably methyl and ethyl.

A "$C_{3-7}$ cycloalkyl" group is cyclopropyl, cyclobutyl, cyclohexyl or cyclopentyl.

A "$C_{3-7}$ cycoalkyl-$C_{1-8}$ alkyl" group is one such cycloalkyl group attached through a $C_{1-8}$ alkyl group (an alkylene group) to the ring.

A "$C_{1-8}$ alkoxy" group is one of the above-mentioned $C_{1-8}$ alkyl groups attached through oxygen to the ring, and preferred examples are methoxy and ethoxy.

A "$C_{3-7}$ cycloalkoxy" group is a $C_{3-7}$ cycloalkyl group as mentioned above linked through an oxygen atom to the ring as, for example, cyclopropyloxy, cyclopentyloxy and cyclohexyloxy.

A "$C_{3-7}$ cycloalkylC$_{1-8}$ alkoxy" group is a $C_{3-7}$ cycloalkyl-$C_{1-8}$ alkyl as mentioned above linked through an oxygen atom to the ring as, for example, cyclohexylmethoxy.

A "carbo($C_{1-8}$)alkoxy" group is a

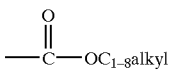

group, for example a carbomethoxy or carboethoxy group.

An "optionally substituted aryl" group is a mononuclear or polynuclear aromatic hydrocarbon group, for example phenyl or naphthyl, which is optionally substituted with one or more, preferably one to three, substituents independently selected from, for example, $C_{1-8}$ alkyl, $C_{1-8}$ alkoxy, carboxy, hydroxy, cyano, halo, trifluoromethyl, SCH$_3$, nitro, phenyl, 3,4-methylenedioxy, amino, and phenyl which is optionally substituted by from one to three independently selected from the group consisting of $C_{1-8}$ alkyl, $C_{1-8}$ alkoxy, carboxy, hydroxy, cyano, halo, trifluoromethyl, SCH$_3$, nitro, phenyl, 3,4-methylenedioxy, and amino.

"Heteroaryl" means about a four to about a ten membered aromatic mononuclear or polynuclear ring system in which one or more of the atoms in the ring is an element other than carbon, for example nitrogen, oxygen, or sulfur. Examples of heteroaryl groups include indolyl, imidazolyl, furanyl, thiophenyl, benzofuranyl, benzothiopenyl, pyridyl, quinolinyl, oxazolyl, pyrrolyl, isoxazolyl, pyrimidyl, thiazolyl, and benzimidazolyl. An "optionally substituted heteroaryl" group is a heteroaryl group which is optionally substituted with one or more, preferably one to three, substituents independently selected from, for example, $C_{1-8}$ alkyl, $C_{1-8}$ alkoxy, carboxy, hydroxy, cyano, halo, trifluoromethyl, SCH$_3$, nitro, phenyl, 3,4-methylenedioxy, amino, and phenyl which is optionally substituted by from one to three substituents independently selected from the group consisting of $C_{1-8}$ alkyl, $C_{1-8}$ alkoxy, carboxy, hydroxy, cyano, halo, trifluoromethyl, SCH$_3$, nitro, phenyl, 3,4-methylenedioxy, and amino.

"Optionally substituted heterocyclyl" means about a four to about a 10 membered mononuclear or polynuclear saturated or partially unsaturated ring system in which one or more of the atoms in the ring is an element other than carbon, for example nitrogen, oxygen, or sulfur, and which is optionally substituted with one or more, preferably one to three, substituents independently selected from, for example, $C_{1-8}$ alkyl, $C_{1-8}$ alkoxy, carboxy, hydroxy, cyano, halo, trifluoromethyl, SCH$_3$, nitro, phenyl, amino, and phenyl which is optionally substituted by from one to three substituents independently selected from the group consisting of $C_{1-8}$ alkyl, $C_{1-8}$ alkoxy, carboxy, hydroxy, cyano, halo, trifluoromethyl, $SCH_3$, nitro, phenyl, 3,4-methylenedioxy, and amino. Examples of heterocyclyl groups inicude piperidyl, imidazolidinyl, tetrahydrofuranyl, morpholinyl, homopiperidinyl, tetrahydroquinolinyl, dioxanyl, and tetrahydranpyranyl.

An "aryl-$C_{1-8}$ alkyl" group can be, for example, optionally substituted phenyl-$C_{1-8}$ alkyl or optionally substituted naphthyl-$C_{1-8}$ alkyl, such optionally substituted groups being optionally substituted with one or more, preferably one to three, substituents selected from, for example, $C_{1-8}$ alkyl, $C_{1-8}$ alkoxy, carboxy, hydroxy, cyano, halo, trifluoromethyl, $SCH_3$, nitro and amino. A preferred aryl-$C_{1-8}$ alkyl group is optionally substituted phenyl-$(CH_2)_x$— where x is 1 or 2, most preferably optionally substituted benzyl.

A halo group is preferably chloro, bromo or fluoro.

A halo $C_{1-8}$ alkyl or halo $C_{1-8}$ alkoxy group is a substituent in which one or more, preferably one to three, hydrogen atoms on the $C_{1-8}$ alkyl moiety is replaced by a halo atom, preferably chloro, bromo or fluoro.

An "alkoxyalkoxy" group is of the formula $CH_3(CH_2)_p$—O—$(CH_2)_q$—O—, where p is 0–4 and q is 1–5, preferred examples being those in which p is 0 or 1 and q is 1–3, especially methoxyethoxy, ethoxyethoxy, ethoxypropoxy, or methoxypropoxy.

A "$C_{1-8}$ acylamino" substituent is preferably of the formula RCONH— where RCO is any appropriate acid residue, RCO containing from 1–8 carbon atoms. Examples of R include $C_{1-8}$ alkyl, in particular methyl or ethyl, acetyl being the most preferred acyl group. R can also be aryl $C_{1-8}$ alkyl, especially benzyl, or R can be halo-$C_{1-8}$ alkyl, especially trifluoromethyl.

The "acyl" moiety, alone or in combination, is derived from an alkanoic acid containing from one to eight carbon atoms. The term "acyl" also includes moieties derived from an aryl carboxylic acid.

As used herein, the term "aryl coupling" shall mean any appropriate method for coupling two aromatic or heteroaromatic rings known to the artisan. Such methods may include, but are not limited to Stille coupling or Suzuki coupling methods. The Suzuki coupling is an especially preferred coupling method. The Suzuki method using Ar—$B(OH)_2$ and Pd catalyst is particularly preferred for use in the synthesis methods described herein. The artisan will appreciate that there are a variety of available Pd catalysts which are acceptable for the Suzuki coupling. One such Pd catalyst which is preferred for the methods described herein is $Pd(PPh_3)_4$ The term "treating", as used herein, describes the management and care of a patient for the purpose of combating the disease, condition, or disorder and includes the administration of a compound of present invention to prevent the onset of the symptoms or complications, to alleviate the symptoms or complications, or to eliminate the disease, condition, or disorder.

In the above formula (I), the moiety X is preferably —$NR^5$—, where $R^5$ is hydrogen or an amino protecting group, and is most preferably hydrogen, the protected derivatives being mainly useful as intermediates. Protecting groups can be any of the conventional amino protecting groups, see, for instance, T. W. Greene, *Protective Groups in Organic Synthesis* chapter 7, John Wiley and Sons, New York, 1981, and by J. W. Barton, *Protective Groups in Organic Chemistry*, chapter 2, J. F. W. McOmie, ed., Plenum Press, New York, 1973. Examples of such groups include but are not intended to be limited to benzyl and substituted benzyl such as 3,4-dimethoxybenzyl, O-nitrobenzyl, and triphenylmethyl; those of the formula —COOR where R includes such groups as methyl, ethyl, propyl, isopropyl, 2,2,2-trichloroethyl, 1-methyl-1-phenylethyl, isobutyl, t-butyl, t-amyl, vinyl, allyl, phenyl, benzyl, p-nitrobenzyl, O-nitrobenzyl, and 2,4-dichlorobenzyl; acyl groups and substituted acyl such as formyl, acetyl, chloroacetyl, dichloroacetyl, trichloroacetyl, trifluoroacetyl, benzoyl, and p-methoxybenzoyl; and other groups such as methanesulfonyl, p-toluenesulfonyl, p-bromobenzenesulfonyl, p-nitrophenylethyl, p-toluenesulfonylaminocarbonyl, and the like. Preferred nitrogen protecting groups are benzyl, acyl, or silyl.

It is preferred that $R^1$ and $R^{1'}$ are hydrogen or methyl, and $R^2$ and $R^3$ are hydrogen, or $R^1$ and $R^{1'}$ are both hydrogen, and $R^2$ and $R^3$ are hydrogen or methyl, and that

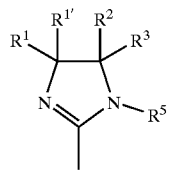

of Formula (I) is an imidazolinyl group. Especially preferred imidazolines are those wherein $R^1$, $R^{1'}$, $R^2$ and $R^3$ are each hydrogen; and $R^5$ is hydrogen or an amino protecting group.

Further preferred compounds of Formula (I), as defined hereinabove, are those which have one or more of the following independently selected features:

(i) $R^1$ and $R^{1'}$ are hydrogen and $R^2$ and $R^3$ are hydrogen or methyl, more preferably $R^1$, $R^{1'}$, $R^2$ and $R^3$ are hydrogen;

(ii) X is —NH—;

(iii) n is 0;

(iv) $R^4$ is

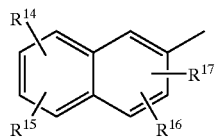

in which $R^{14}$ and $R^{16}$ are indepedently selected from hydrogen, halo, or optionally substituted phenyl, naphthyl or thienyl, more preferably from hydrogen, bromo, chloro, phenyl, 2-fluorophenyl, 3-fluorophenyl, 4-fluorophenyl, 4-methylphenyl, 3-methylphenyl, 2-methylphenyl ,4-chlorophenyl, 3-chlorophenyl, 2-chlorophenyl, 2,3-dichlorophenyl, 2,4-dichlorophenyl, 3,4-dichlorophenyl, 3,5-dichlorophenyl, 3-chloro-4-fluorophenyl, 5-chloro-2-thienyl, 2-thienyl, 3-thienyl, 4-(trifluoromethyl)phenyl, 2,4-dimethoxyphenyl, 4-methoxyphenyl, 3-methoxyphenyl, 2-methoxyphenyl, 3-(trifluoromethyl)phenyl, biphenyl, 4'-chlorobiphenyl, or 3-nitrophenyl, and most preferably from hydrogen, bromo, chloro, phenyl, 2-fluorophenyl, 3-fluorophenyl, 4-fluorophenyl, 5-chloro-2-thienyl, 2,4-dichlorophenyl, 4-chlorophenyl, 2,4-dichlorophenyl, 3,4-dichlorophenyl, 3,5-dichlorophenyl, 4-methylphenyl, 3-chloro-4-fluorophenyl, 4-(trifluoromethyl)phenyl, 2-methoxyphenyl, or 4-methoxyphenyl, R¹⁵ is selected from hydrogen, halo, methyl, or methoxy, more preferably hydrogen, and R¹⁷ is selected from benzyloxy, propoxy, butoxy, $H_3C(CH_2)_p$—O—$(CH_2)_q$—O—, $H_3C(CH_2)_p$—S—$(CH_2)_q$—O—, $H_3C(CH_2)_p$—SO_2—$(CH_2)_q$—O—, (tetrahydropyran-2-yl)methoxy, cyclobutylmethoxy, cyclopentylmethoxy, or cyclohexylmethoxy, more preferably from $H_3C$—O—$(CH_2)_2$—O—, $H_3CCH_2$—O—$(CH_2)_2$—O—, $H_3C$—O—$(CH_2)_3$—O—, $H_3CCH_2$—O—$(CH_2)_3$—O—, or cyclobutylmethoxy, and most preferably $H_3C$—O—$(CH_2)_2$—O—;

(v) R⁴ is an indol-3-yl group of the formula

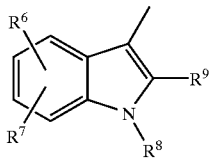

in which

R⁶ is selected from hydrogen, halo, nitro, cyano, $C_{1-6}$ alkyl, halo $C_{1-6}$ alkyl, halo $C_{1-6}$ alkoxy, or halo $C_{1-6}$ alkylthio, more preferably from chloro, fluoro, methyl, trifluoromethyl, or pentafluoroethyl which are in the 5-position of the indole nucleus, R⁷ is hydrogen, halo, or methyl, more preferably in the 7-position of the indole nucleus, still more preferably hydrogen or chloro, and most preferably hydrogen, R⁸ is hydrogen, methyl, or optionally substituted benzyl, more preferably hydrogen or 2-chlorobenzyl, and most preferably hydrogen, R⁹ is hydrogen, C1–6 alkyl, halo C1–6 alkyl, optionally substituted benzyl, optionally substituted phenyl, or optionally substituted thienyl, more preferably hydrogen, methyl, trifluoromethyl, benzyl, 3-chlorobenzyl, phenyl, 4-methylphenyl, 2,4dichlorophenyl, 3-methyl-2-thienyl, 2,5-dimethyl-3-thienyl, 4-methoxyphenyl, 2-methoxyphenyl, 4-chlorophenyl, 3-chlorophenyl, 2-chlorophenyl, 2-methylphenyl, 3-methylphenyl, 3-thienyl, 2-bromophenyl, 4-chloro-3-methylphenyl, 2,4-dimethylphenyl, 2-(trifluoromethyl)phenyl, or 3-fluorophenyl, and most preferably hydrogen, methyl, benzyl, 3-chlorobenzyl, 4-chlorophenyl, 3-chlorophenyl, 2-chlorophenyl, 3-methylphenyl, 4-chloro-3-methylphenyl, 4-methoxyphenyl, or 2-methoxyphenyl;

(vi) R⁴ is a benzofuran-3-yl (Y=O) or benzothien-3-yl (Y=S) group

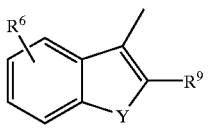

in which

R⁶ is selected from hydrogen, halo, $C_{1-6}$ alkyl, or halo $C_{1-6}$ alkyl, more preferably from chloro, fluoro, methyl, or trifluoromethyl which are in the 5-position of the bicyclic nucleus, and most preferably chloro, R⁹ is $C_{1-6}$ alkyl or optionally substituted phenyl, more preferably methyl, 4-methylphenyl, 4-methoxyphenyl, 2-methoxyphenyl, 4-chlorophenyl, 3-chlorophenyl, or 2-chlorophenyl, and most preferably methyl or 2-chlorophenyl;

(vii) R⁴ is a benzofuran-2-yl group

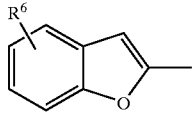

in which R⁶ is selected from hydrogen, halo, C1–6 alkyl, or optionally substituted phenyl, naphthyl, or thienyl, more preferably from bromo, phenyl, 4-methylphenyl, 5-chloro-2-thienyl, 2-thienyl, 3-thienyl, 3-trifluoromethylphenyl, 3-methoxyphenyl, 2-methoxyphenyl, 3,5-bistrifluoromethylphenyl, 4-fluorophenyl, or 3-fluorophenyl;

(viii) R⁴ is a benzothien-2-yl group

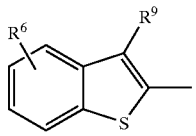

in which

R⁶ is selected from hydrogen, halo, $C_{1-6}$ alkyl, halo $C_{1-6}$ alkyl, $C_{1-6}$ alkoxy, and more preferably from hydrogen, chloro, bromo, methoxy, methyl, or trifluoromethyl, and R⁹ is hydrogen, halo, $C_{1-4}$ alkoxy, $C_{1-4}$ alkyl, optionally substituted phenyl, naphthyl, or thienyl, or an optionally substituted phenylmethyl, optionally substituted naphthylmethyl, optionally substituted thienylmethyl, or optionally substituted pyridylmethyl group in which the methyl group is substituted by hydroxy;

(ix) R⁴ is a quinolin-3-yl group

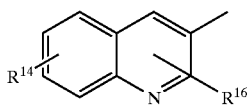

in which

R¹⁴ is selected from hydrogen, halo, C1–4 alkyl, C1–4 alkoxy, or halo C1–4 alkyl, more preferably from halo, C1–4 alkyl, or trifluoromethyl, and most preferably from chloro, methyl, or trifluoromethyl in the 6-position of the quinoline nucleus, and R¹⁶ is C1–4 alkyl, halo C1–4 alkyl, or optionally substituted phenyl, more preferably methyl, trifluoromethyl, phenyl, or 4-methylphenyl in the 2-position of the quinoline nucleus, and mostly preferably methyl.

Preferred compounds of the present invention include:

3-(4,5-Dihydroimidazol-2-yl)-2,5-dimethyl-1H-indole;

5-Chloro-3-(4,5-dihydroimidazol-2-yl)-2-methyl-1H-indole;

3-(4,5-Dihydroimidazol-2-yl)-2-methyl-5-trifluoromethyl-1H-indole;

3-(4,5-Dihydroimidazol-2-yl)-2-methyl-5-pentafluoroethyl-1H-indole;

5,7-Dichloro-3-(4,5-dihydroimidazol-2-yl)-2-methyl-1H-indole;
3-(4,5-Dihydroimidazol-2-yl)-5-fluoro-2-methyl-1H-indole;
3-(4,5-Dihydroimidazol-2-yl)-2-methyl-5-nitro-1H-indole;
5-Bromo-3-(4,5-dihydroimidazol-2-yl)-2-methyl-1H-indole;
5-Chloro-3-(4,5-dihydroimidazol-2-yl)-2-phenyl-1H-indole;
5,7-Dichloro-3-(4,5-dihydroimidazol-2-yl)-2-phenyl-1H-indole;
5-Chloro-3-(4,5-dihydroimidazol-2-yl)-7-methyl-2-phenyl-1H-indole;
5-Chloro-2-(4-chlorophenyl)-3-(4,5-dihydroimidazol-2-yl)-1H-indole;
5-Chloro-2-(3-chlorophenyl)-3-(4,5-dihydroimidazol-2-yl)-1H-indole;
5-Chloro-2-(2-chlorophenyl)-3-(4,5-dihydroimidazol-2-yl)-1H-indole;
2-(4-Chlorophenyl)-5,7-dichloro-3-(4,5-dihydroimidazol-2-yl)-1H-indole;
2-(2-Chlorophenyl)-3-(4,5-dihydroimidazol-2-yl)-5-fluoro-1H-indole;
2-(2-Bromophenyl)-5-chloro-3-(4,5-dihydroimidazol-2-yl)-1H-indole;
5-Chloro-3-(4,5-dihydroimidazol-2-yl)-2-(3-fluorophenyl)-1H-indole;
5-Chloro-3-(4,5-dihydroimidazol-2-yl)-2-(4-iodophenyl)-1H-indole;
5-Chloro-3-(4,5-dihydroimidazol-2-yl)-2-(4-methylphenyl)-1H-indole;
5-Chloro-3-(4,5-dihydroimidazol-2-yl)-2-(3-methylphenyl)-1H-indole;
5,7-Dichloro-3-(4,5-dihydroimidazol-2-yl)-2-(3-methylphenyl)-1H-indole;
5-Chloro-3-(4,5-dihydroimidazol-2-yl)-2-(2-methylphenyl)-1H-indole;
5-Chloro-3-(4,5-dihydroimidazol-2-yl)-2-(2-trifluoromethylphenyl)-1H-indole;
2-(2,4-Dichlorophenyl)-3-(4,5-dihydroimidazol-2-yl)-5-fluoro-1H-indole;
3-(4,5-Dihydroimidazol-2-yl)-2-(2,4-dimethylphenyl)-5-fluoro-1H-indole;
5-Chloro-3-(4,5-dihydroimidazol-2-yl)-2-(2,4-dimethylphenyl)-1H-indole;
5-Chloro-3-(4,5-dihydroimidazol-2-yl)-2-(2,5-dimethylphenyl)-1H-indole;
5-Chloro-3-(4,5-dihydroimidazol-2-yl)-2-(2-methoxyphenyl)-1H-indole;
5-Chloro-3-(4,5-dihydroimidazol-2-yl)-2-(4-methoxyphenyl)-1H-indole;
5-Chloro-2-(4-chloro-3-methylphenyl)-3-(4,5-dihydroimidazol-2-yl)-1H-indole;
5-Chloro-3-(4,5-dihydroimidazol-2-yl)-2-(4-(2-methoxyethoxy)phenyl)-1H-indole;
5-Chloro-3-(4,5-dihydroimidazol-2-yl)-2-(2-(2-methoxyethoxy)phenyl)-1H-indole;
5-Chloro-3-(4,5-dihydroimidazol-2-yl)-1H-indole;
5-Chloro-2-cyclohexyl-3-(4,5-dihydroimidazol-2-yl)-1H-indole;
5-Chloro-2-(cyclohexen-1-yl)-3-(4,5-dihydroimidazol-2-yl)-1H-indole;
2,5-Bistrifluoromethyl-3-(4,5-dihydroimidazol-2-yl)-1H-indole;
2-Benzyl-5-chloro-3-(4,5-dihydroimidazol-2-yl)-1H-indole;
5-Chloro-2-(2-chlorobenzyl)-3-(4,5-dihydroimidazol-2-yl)-1H-indole;
5-Chloro-2-(3-chlorobenzyl)-3-(4,5-dihydroimidazol-2-yl)-1H-indole;
5-Chloro-1-(2-chlorobenzyl)-3-(4,5-dihydroimidazol-2-yl)-2-methyl-1H-indole;
5-Chloro-3-(4,5-dihydro-4,4-dimethylimidazol-2-yl)-2-methyl-1H-indole;
5-Chloro-2-(2-chlorophenyl)-3-(4,5-dihydro-4,4-dimethylimidazol-2-yl)-1H-indole;
5-Chloro-3-(4,5-dihydroimidazol-2-yl)-2-pyridin-4-yl)-1H-indole;
5-Chloro-3-(4,5-dihydroimidazol-2-yl)-2-(3-thienyl)-1H-indole;
5-Chloro-3-(4,5-dihydroimidazol-2-yl)-2-(2,5-dimethyl-3-thienyl)-1H-indole;
5-Chloro-3-(4,5-dihydroimidazol-2-yl)-2-(3-methyl-2-thienyl)-1-indole;
2-[2-(2-(2-Fluorophenyl)indol-3-yl)ethyl]-4,5-dihydroimidazole;
2-[2-(2-(2-Chlorophenyl)indol-3-yl)ethyl]-4,5-dihydroimidazole;
2-[5-Chloro-2-(2-chlorophenyl)benzofuran-3-yl]-4,5-dihydro-1H-imidazole;
2-[5-Chloro-2-(3-chlorophenyl)benzofuran-3-yl]-4,5-dihydro-1H-imidazole;
2-[5-Chloro-2-methylbenzofuran-3-yl]-4,5-dihydro-1H-imidazole;
2-[5-Fluoro-2-methylbenzofuran-3-yl]-4,5-dihydro-1H-imidazole;
2-[2-(2-Chlorophenyl)-5-fluorobenzo[b]thiophen-3-yl]-4,5-dihydro-1H-imidazole;
2-[5-Fluoro-2-(4-methylphenyl)benzo[b]thiophen-3-yl]-4,5-dihydro-1H-imidazole;
2-(5-Chloro-2-methylbenzo[b]thiophen-3-yl)-4,5-dihydro-4,4-dimethyl-1H-imidazole;
2-[7-Bromo-3-(2-methoxyethoxy)naphthalen-2-yl]-4,5-dihydro-1H-imidazole;
2-[3-(2-Methoxyethoxy)-7-phenyl-naphthalen-2-yl]-4,5-dihydro-1H-imidazole;
2-[7-(2-Fluorophenyl)-3-(2-methoxyethoxy)naphthalen-2-yl]-4,5-dihydro-1H-imidazole;
2-[7-(3-Fluorophenyl)-3-(2-methoxyethoxy)naphthalen-2-yl]-4,5-dihydro-1H-imidazole;
2-[7-(4-Fluorophenyl)-3-(2-methoxyethoxy)naphthalen-2-yl]-4,5-dihydro-1H-imidazole;
2-[7-(3,5-Dichlorophenyl)-3-(2-methoxyethoxy)naphthalen-2-yl]-4,5-dihydro-1H-imidazole;
2-[3-(2-Methoxyethoxy)-7-(4-methylphenyl)naphthalen-2-yl]-4,5-dihydro-1H-imidazole;
2-[3-(2-Methoxyethoxy)-7-(2-thienyl)naphthalen-2-yl]-4,5-dihydro-1H-imidazole;
2-[3-(2-Methoxyethoxy)-7-(3-thienyl)naphthalen-2-yl]-4,5-dihydro-1H-imidazole;
2-[7-(5-Chloro-2-thienyl)-3-(2-methoxyethoxy)naphthalen-2-yl]-4,5-dihydro-1H-imidazole;
2-[7-(2-Methoxyphenyl)-3-(2-methoxyethoxy)naphthalen-2-yl]-4,5-dihydro-1H-imidazole;
2-[7-(4-Methoxyphenyl)-3-(2-methoxyethoxy)naphthalen-2-yl]-4,5-dihydro-1H-imidazole;
2-[3-(2-Methoxyethoxy)-7-(3-nitrophenyl)naphthalen-2-yl]-4,5-dihydro-1H-imidazole;
2-[7-Bromo-4-chloro-3-(2-methoxyethoxy)naphthalen-2-yl]-4,5-dihydro-1H-imidazole;
2-[4-Bromo-7-(5-chloro-2-thienyl)-3-(2-methoxyethoxy)naphthalen-2-yl]-4,5-dihydro-1H-imidazole;
2-[4-Chloro-7-(5-chloro-2-thienyl)-3-(2-methoxyethoxy)naphthalen-2-yl]-4,5-dihydro-1H-imidazole;
2-[4-Chloro-3-(2-methoxyethoxy)-7-(3-thienyl)naphthalen-2-yl]-4,5-dihydro-1H-imidazole;

2-[4-Chloro-3-(2-methoxyethoxy)-7-(4-methylphenyl) naphthalen-2-yl]-4,5-dihydro-1H-imidazole;
2-[4-Chloro-7-(4-chlorophenyl)-3-(2-methoxyethoxy) naphthalen-2-yl]-4,5-dihydro-1H-imidazole;
2-[4-Chloro-3-(2-methoxyethoxy)-7-(3-methoxyphenyl) naphthalen-2-yl]-4,5-dihydro-1H-imidazole;
2-[4-Chloro-3-(2-methoxyethoxy)-7-(4-trifluoromethylphenylnaphthalen-2-yl]-4,5-dihydro-1H-imidazole;
2-[3-(2-Ethoxyethoxy)-7-(4-methylphenyl)naphthalen-2-yl]-4,5-dihydro-1H-imidazole;
2-[7-(4-Methylphenyl)-3-(tetrahydropyran-2-yl) methoxynaphthalen-2-yl]-4,5-dihydro-1H-imidazole;
2-[7-(4-Fluorophenyl)-3-(2-methylthioethoxy)naphthalen-2-yl]-4,5-dihydro-1H-imidazole;
2-[7-(4-Methoxyphenyl)-3-(3-methoxypropoxy) naphthalen-2-yl]-4,5-dihydro-1H-imidazole;
2-[7-(5-Chloro-2-thienyl)-3-butoxynaphthalen-2-yl]-4,5-dihydro-1H-imidazole;
2-[7-(5-Chloro-2-thienyl)-3-(2-ethoxyethoxy)naphthalen-2-yl]-4,5-dihydro-1H-imidazole;
2-[4-Bromo-3-(2-methoxyethoxy)naphthalen-2-yl]-4,5-dihydro-1H-imidazole;
2-[3-(2-Methoxyethoxy)-4-(4-methylphenyl)naphthalen-2-yl]-4,5-dihydro-1H-imidazole;
2-[4-(4-Chlorophenyl)-3-(2-methoxyethoxy)naphthalen-2-yl]-4,5-dihydro-1H-imidazole;
2-[4-(2,4-Dichlorophenyl)-3-(2-methoxyethoxy) naphthalen-2-yl]-4,5-dihydro-1H-imidazole;
2-[3(2-Methoxyethoxy)-4-(4-methoxyphenyl)naphthalen-2-yl]-4,5-dihydro-1H-imidazole;
2-[3-(2-Methoxyethoxy)-4-(3methoxyphenyl)naphthalen-2-yl]-4,5-dihydro-1H-imidazole;
2-[3-(2-Methoxyethoxy)-4-(2-methoxyphenyl)naphthalen-2-yl]-4,5-dihydro-1H-imidazole;
2-[3-(2-Methoxyethoxy)-4-(2-thienyl)naphthalen2–2yl]-4,5-dihydro-1H-imidazole;
2-[4-(5-Chloro-2-thienyl)-3-(2-methoxyethoxy)naphthalen-2-yl]-4,5-dihydro-1H-imidazole;
2-[4-Bromo-3-propoxynaphthalen-2-yl]-4,5-dihydro-1H-imidazole;
2-[4-(3,4-Dichlorophenyl)-3-(2-methoxyethoxy) naphthalen-2-yl]-4,5-dihydro-1H-imidazole;
2-[4-(3-Chloro-4-fluorophenyl)-3-(cyclobutylmethoxy) naphthalen-2-yl]-4,5-dihydro-1H-imidazole;
6-Chloro-3-(4,5-dihydro-1H-imidazol-2-yl)-3-methylquinoline;
3-(4,5-Dihydro-1H-imidazol-2-yl)-3-phenylquinoline;
2-(3-Phenylbenzo[b]thiophen-2-yl)-4,5-dihydro-1H-imidazole;
2-(3-Butoxybenzo[b]thiophen-2-yl)-4,5-dihydro-1H-imidazole;
(2-(4,5-Dihydro-1H-imidazol-2-yl)benzo[b]thiophen-3yl)-(naphthalen-1-yl)methanol;
(4-tert.-Butylphenyl)-(2-(4,5-dihydro-1H-imidazol-2yl) benzo[b]thiophen-3-yl)methanol;
2-(5-Phenylbenzofuran-2-yl)-4,5-dihydro-1H-imidazole;
2-(5-(3,5-Bistrifluoromethylphenyl)benzofuran-2-yl)-4,5-dihydro-1H-imidazole;
2-(5-(4-Fluorophenyl)benzofuran-2-yl)-4,5-dihydro-1H-imidazole;
2-(5-(4-Methylphenyl)benzofuran-2-yl)-4,5-dihydro-1H-imidazole;
2-(5-(3-Thienyl)benzofuran-2-yl)-4,5-dihydro-1H-imidazole;
2-(5-(3-Fluorophenyl)benzofuran-2-yl)-4,5-dihydro-1H-imidazole;
2-(5-(3-Trifluoromethylphenyl)benzofuran-2-yl)-4,5-dihydro-1H-imidazole;
2-(5-(2-Thienyl)benzofuran-2-yl)-4,5-dihydro-1H-imidazole;
2-(5-(5-Chloro-2-thienyl)benzofuran-2-yl)-4,5-dihydro-1H-imidazole;
2-(5-(3-Methoxyphenyl)benzofuran-2-yl)-4,5-dihydro-1H-imidazole;
2-(5-(2-Methoxyphenyl)benzofuran-2-yl)-4,5-dihydro-1H-imidazole;
2-(7-(4-Methylphenyl)benzofuran-2-yl)-4,5-dihydro-1H-imidazole;
2-(7-(3-Thienyl)benzofuran-2-yl)-4,5-dihydro-1H-imidazole;
2-(7-(2-Thienyl)benzofuran-2-yl)-4,5-dihydro-1H-imidazole; and
2-(4-(5-Chloro-2-thienyl)benzofuran-2-yl)-4,5-dihydro-1H-imidazole.

More preferred compounds of the present invention include:

5-Chloro-3-(4,5-dihydroimidazol-2-yl)-2-methyl-1H-indole;
3-(4,5-Dihydroimidazol-2-yl)-2methyl-5-trifluoromethyl-1H-indole;
5-Chloro-2-(3-chlorophenyl)-3-(4,5-dihydroimidazol-2-yl)-1H-indole;
5-Chloro-2-(2-chlorophenyl)-3-(4,5-dihydroimidazol-2-yl)-1H-indole;
6-Chloro-3-(4,5-dihydro-1H-imidazol-2-yl)-3-methylquinoline;
2-[3-(2-Methoxyethoxy)-7-(4-methylphenyl)naphthalen-2-yl]-4,5-dihydro-1H-imidazole;
2-[3-(2-Methoxyethoxy)-7-phenyl-naphthalen-2-yl]-4,5-dihydro-1H-imidazole;
2-[7-(5-Chloro-2-thienyl)-3-(2-ethoxyethoxy)naphthalen-2-yl]-4,5-dihydro-1H-imidazole;
2-[7-(2-Fluorophenyl)-3-(2-methoxyethoxy)naphthalen-2-yl]-4,5-dihydro-1H-imidazole;
2-[7-(4-Methoxyphenyl)-3-(3-methoxypropoxy) naphthalen-2-yl]-4,5-dihydro-1H-imidazole;
2-[4-(4-Chlorophenyl)-3-(2-methoxyethoxy)naphthalen-2-yl]-4,5-dihydro-1H-imidazole; and
2-[4-(2,4-Dichlorophenyl)-3-(2-methoxyethoxy) naphthalen-2-yl]-4,5-dihydro-1H-imidazole.

By virtue of their acidic moieties, some of the compounds of Formula I include the pharmaceutically acceptable base addition salts thereof. Such salts include those derived from inorganic bases such as ammonium and alkali and alkaline earth metal hydroxides, carbonates, bicarbonates, and the like, as well as salts derived from basic organic amines such as aliphatic and aromatic amines, aliphatic diamines, hydroxy alkamines, and the like. Such bases useful in preparing the salts of this invention thus include ammonium hydroxide, potassium carbonate, sodium bicarbonate, calcium hydroxide, methylamine, diethylamine, ethylenediamine, cyclohexylamine, ethanolamine and the like.

Because of a basic moiety, some of the compounds of Formula I can also exist as pharmaceutically acceptable acid addition salts. Acids commonly employed to form such salts include inorganic acids such as hydrochloric, hydrobromic, hydroiodic, sulfuric and phosphoric acid, as well as organic acids such as para-toluenesulfonic, methanesulfonic, oxalic, para-bromophenylsulfonic, carbonic, succinic, citric, benzoic, acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, heptanoate, propiolate, oxalate, malonate, succinate, suberate, sebacate, fumarate, maleate, 2-butyne-1, 4 dioate, 3-hexyne-2, 5-dioate, benzoate, chlorobenzoate, hydroxybenzoate, methoxybenzoate, phthalate, xylenesulfonate, phenylacetate, phenylpropionate, phenylbutyrate, citrate, lactate, hippurate, β-hydroxybutyrate, glycollate, maleate, tartrate, methanesulfonate, propanesulfonate, naphthalene-1-sulfonate, naphthalene-2-sulfonate, mandelate and the like salts.

In addition, it is recognised that compounds of the present invention may form a variety of solvates with a number of different solvents. Representative solvates can be useful as final embodiments of the present invention or as intermediates in the isolation or preparation of the final embodiments of this invention. For example solvates can be prepared with lower alcohols such as ethanol and with alkyl esters such ethylacetate.

It is recognised that various stereoisomeric forms of the compounds of Formula I may exist. The compounds may be prepared as racemates and can be conveniently used as such. Therefore, the racemates, individual enantiomers (including, but in no way limited to atropisomers), diastereomers, or mixtures thereof form part of the present invention. Unless otherwise specified, whenever a compound is described or referenced in this specification all the racemates, individual enantiomers, diastereomers, or mixtures thereof are included in said reference or description.

In addition to the pharmaceutically acceptable salts, other salts are included in the invention. They may serve as intermediates in the purification of compounds or in the preparation of other, for example pharmaceutically acceptable, acid addition salts, or are useful for identification, characterisation or purification.

General methods of synthesis for the compounds of the present invention are described in Schemes I–XII below.

General Scheme for the Synthesis of Indolyl-Imidazolines

Compounds of formula I wherein X is NH; $R^1$, $R^{1'}$, $R^2$, $R^3$ are hydrogen; n is 1 or 2; $R^4$ is

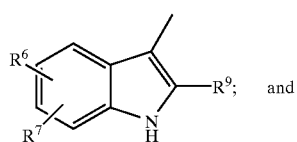
and $R^6$, $R^7$, $R^9$ have the definitions given above can be prepared according to scheme I.

Scheme I

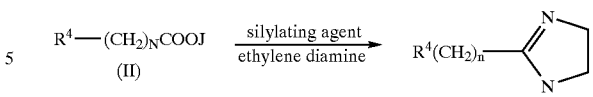

where in $R^4$ and n are as defined herein for Formula I, and J is $C_{1-8}$alkyl, aryl, or aryl $C_{1-8}$alkyl.

The transformation described in Scheme I is novel and represents an additional embodiment of the present invention and is described in Scheme Ia.

Cyclisation is induced by a silylating agent or a mixture of silylating agents, optionally in the presence of an soluble or insoluble base, e.g. triethyl amine or dimethylaminomethyl polystyrene and a solvent. Useful reagents are e.g. described in FLUKA Chemika "Silylating Agents" (1995) ISBN 3-905617-08-0 and the literature cited therein.

In a more prefered embodiment, these silylating agents are trimethyl silyl halogenides, TMS-X (e.g. trimethyl silyl chloride or trimethyl silyl iodide) or hexamethyl disilazane, HMDS or trimethyl silyl diethylamine, TMS-DEA or mixtures of them. In the most prefered embodiment the reactions are carried out either in methylene chloride with excess TMS-Cl or, more prefered, TMS-I in presence of triethyl amine or dimethylaminomethyl polystyrene at ambient temperature, or in neat HMDS or HMDS/TMS-Cl 100/1, without additional base and solvent at 50° C. to reflux, preferably at 70° C. to 90° C. In some cases, using TMS-X as cyclizing reagent, excessive reagent has to be added in several portions within a period of time (up to about a week) to ensure complete conversion. The process described herein is compatible to many functionalities present in an organic molecule, e.g. unprotected hydroxy, unprotected amino, olefinic double bond, cyano, nitro, aromatic halogen, amide and is sucessful in some cases, when conventional methods failed (Chem. Pharm. Bull. 1980, 28, 1394–1402).

Scheme Ia

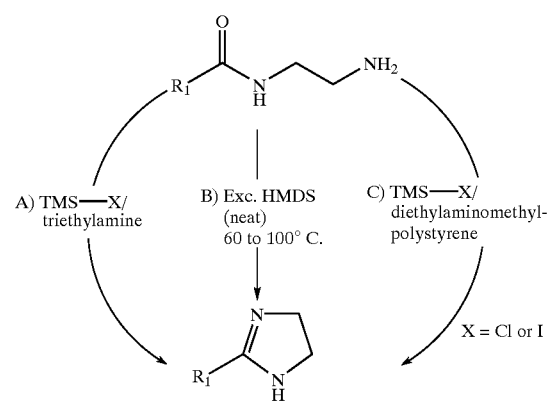

The process described in Scheme Ia affords numerous advantages over similar methods known in the art. The transformation can be achieved in high yield and under mild conditions, whereas, methods known in the art require the use of extreme conditions or reagents Compounds of formula I wherein X is NH; $R^1$, $R^{1'}$, $R^2$, $R^3$ are hydrogen; n is 0; $R^4$ is

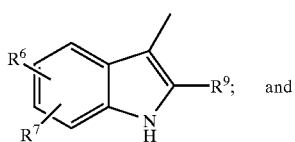 and $R^6$, $R^7$, $R^9$ have the definitions given above can be prepared according to scheme II.

Scheme II

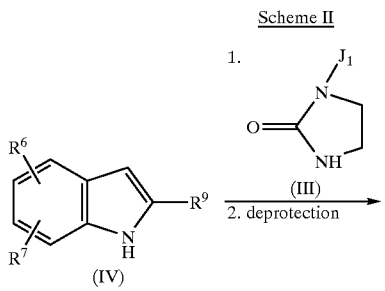

$J_1$ is $COR_2$ or $CO_2R_2$ and
$R_2$ is $C_1$–$C_8$ alkyl, aryl, or aryl $C_1$–$C_8$ alkyl.

The process described in Scheme II is novel and represents another embodiment of the present invention. The process describes the preparation of imidazolines of formula I in which X is NH and R4 is an indole nucleus. The process is affected by treating a compound of formula (IV) with a compound of formula (III) in the presence of a dehydration agent between room temperature and 140° C.; followed by treatment with an alcohol or water between room temperature and the boiling point of the reaction mixturre. The preferred compounds of formula III are 1-acetyl-imidazoline-2-one or 1-(phenyloxycarbonyl)-imidazoline-2-one. The preferred dehydration agent is phosphorus oxychloride or thionylchloride. The preferred reagent for the deprotection of the N-substituted-imidazoline or the N-substituted-imidazole is ethanol or water.

The indole nuclei of formulas (II and IV) utilized in Schemes I and II are known in the art and can be prepared as shown in the Schemes IIIa–IIIf below and as described, for example, in *Bull. Soc. Chim. Fr.* 1969 (4), 1227–34, with the modifications shown, for Schemes IIIa–IIId, and *J. Org. Chem.* (1994) 59, 6372, with the modifications shown, for Scheme IIIf;

Scheme IIIa

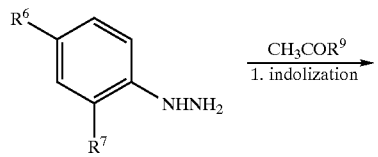

-continued

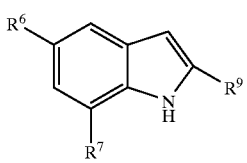

Scheme IIIb

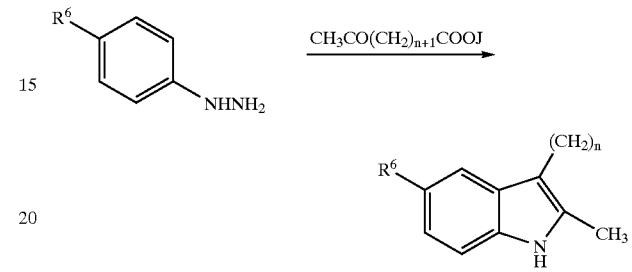

wherein, n, J, and $R^6$ are as defined herein above.

Scheme IIIc

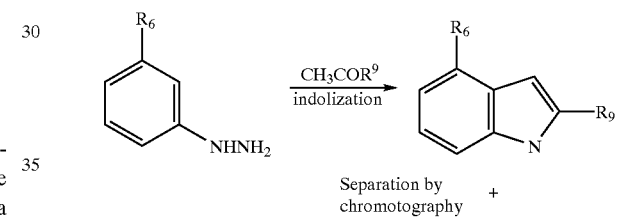

Scheme IIId

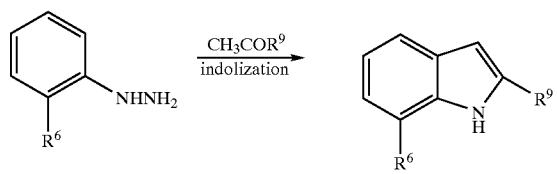

Scheme IIIe

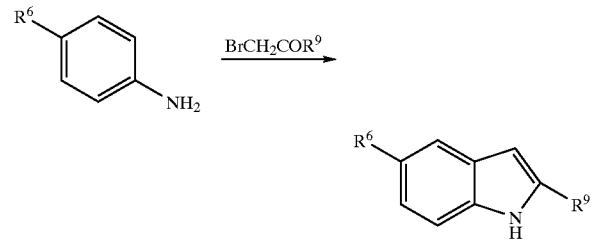

Scheme IIIf

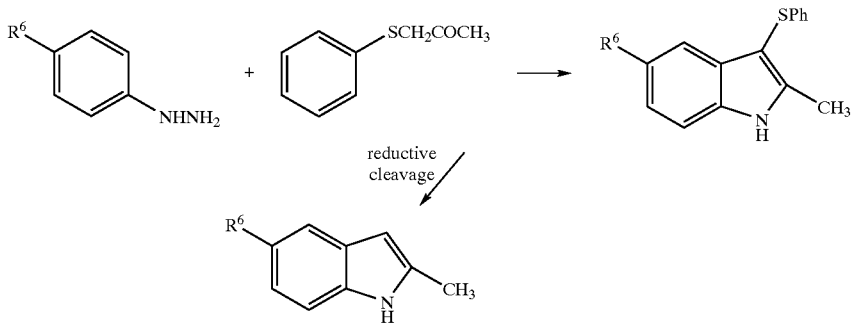

Scheme IIIg, below, describes a method for the synthesis of 3-cyanoindoles and subsequent transformation to the corresponding imidazolines, which are substituted by an aryl or heteroaryl group in position 2 of the indole nucleus. Nitrobenzene derivatives react with acetonitrile derivatives which contain a leaving group L to give (2-nitrophenyl) acetonitriles. Reactions of this type are known, for example as reported by M. Makosza et al., Liebigs Ann. Chem./Recl. 1997, 1805. Typical leaving groups L are halogens, substituted or unsubstituted phenoxy groups, or substituted or unsubstituted phenylthio groups. A preferred value for L is 4-chlorophenoxy. The reaction can be carried out with strong bases, for example, NaOH or KOH, or with alkoxylates, for example, potassium tert.-butoxide in polar solvents such as DMF or DMSO. The resulting acetonitrile is alkylated with benzyl halides or heteroarylmethyl halides, preferably bromides or chlorides. This reaction requires a base typically used for such alkylation. A preferred method uses potassium carbonate and a phase transfer catalyst, for example a crown ether. The following cyclization to 3-cyano-1-hydroxyindoles may also be carried out with strong bases in polar solvents as described above. A preferred procedure uses sodium hydroxide in DMSO. The removal of the 1-hydroxy group can be achieved under conditions which are typically used for this purpose, for example catalytic hydrogenation, reduction with metals, or with phosphorus reagents such as trialkyl phosphites, for example as reported by R. M. Acheson, in "Advances in Heterocyclic Chemistry", Vol. 51, p. 129. In a preferred method the reduction is carried out by heating with trimethyl phosphite. The transformation of the cyano group to an imidazoline is achieved by heating with ethylenediamine. This reaction is achieved, in a preferred process, with ethylenediamine tosylate by heating of both reactants at temperatures >300° C.

Scheme IIIg

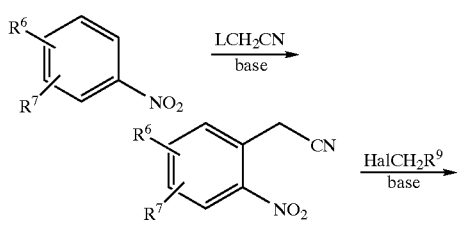

-continued wherein $R^9$ is aryl or heteroaryl.

Scheme IIIh describes a method for the synthesis of indol-3-yl acetates and propionates containing an aryl or heteroaryl group in the 2-position of the indole ring. Indol-3-yl acetates and propionates which are unsubstituted in position 2 are commercially available or may be prepared according to procedures known in the art, for example, in a similar manner as described in Scheme IIIb. The bromination in the 2-position of the indole nucleus may be achieved with bromination reagents and reaction conditions known in the art, for example bromine, NBS, TMS bromide/DMSO, or pyridinium bromide perbromide. A preferred method uses NBS in dichloromethane at 0° C. 2-Bromoindoles are converted to 2-aryl or heteroaryl indoles by standard conditions known in the art for Suzuki coupling reactions using aryl or heteroaryl boronic acids employing a Pd catalyst, preferably Pd(PPh$_3$)$_4$.

Scheme IIIh

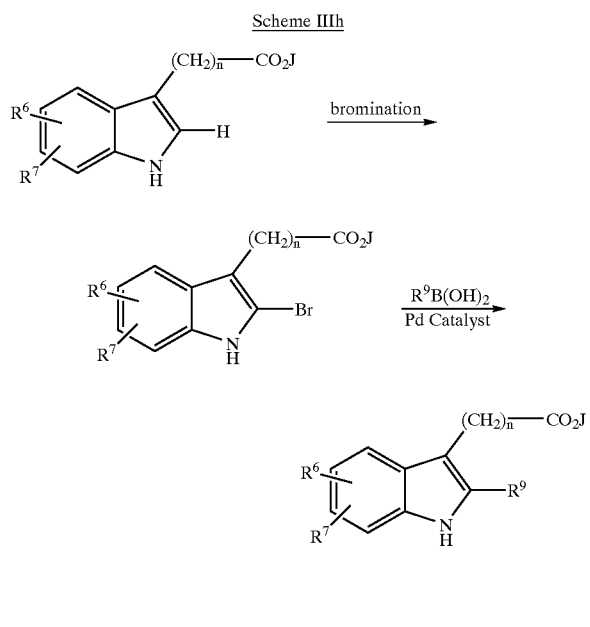

wherein R$^9$ is aryl or heteroaryl, n is 1 or 2, and J is C$_{1-4}$alkyl.

Compounds of Formula I, wherein X is NH; R$^1$, R$^{1'}$, R$^2$, and R$^3$ are hydrogen; n is 0; R$^4$ is

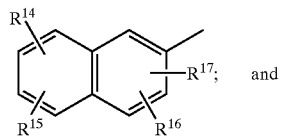

R$^{14}$, R$^{15}$, R$^{16}$, and R$^{17}$ have the definitions given above can be prepared by methods known in the art or as described herein. A skilled artisan would appreciate that the compounds of Formula I could be prepared from the appropriate halo and hydroxy substituted naphthalenes. Such syntheses are illustrated in Schemes IV and V, below.

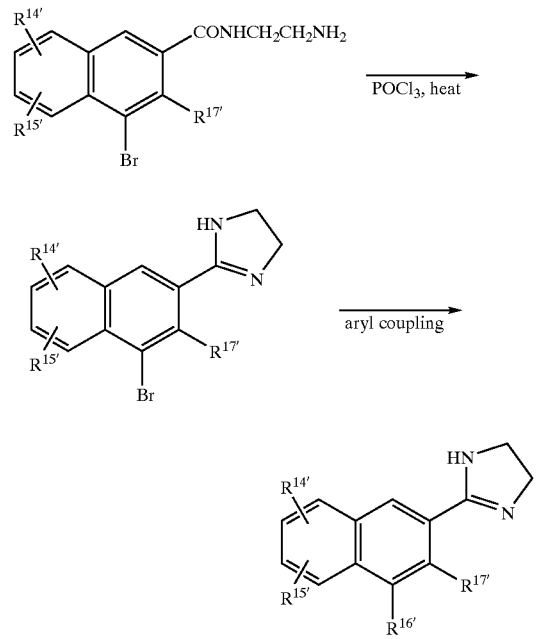

wherein R$^{14'}$, R$^{15'}$, and R$^{17'}$ are R$^{14}$, R$^{15}$, and R$^{17}$, respectively, protected derivatives thereof, or precursor moieties thereto, and R$^{16'}$ is optionally substituted aryl, or optionally substituted heteroaryl.

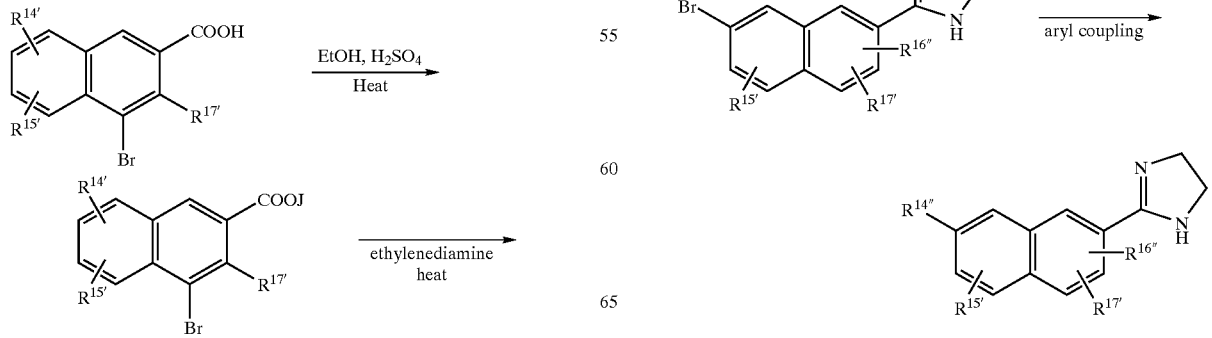

wherein $R^{15'}$, $R^{16''}$ and $R^{17'}$ are $R^{15}$, $R^{16}$, and $R^{17}$, respectively, protected derivatives thereof, or precursor moieties thereto, and $R^{14''}$ is optionally substituted aryl, or optionally substituted heteroaryl.

Scheme VIa illustrates the introduction of the imidazoline group into the 3-position of the benzothiophene (Y=S) or the benzofuran nucleus (Y=O). The unsubstituted bicyclic heterocycle reacts with chloroformates, preferably with ethyl chloroformate to give the corresponding 3-carboxylates. The reaction is catalyzed by Lewis acids, for example, Al(III) chloride, Sn(IV) chloride, Ti(IV) chloride, or boron halides in halogenated hydrocarbons or in carbon disulfide. It should be noted that when carbon disulfide is used, intermediate dithioesters are formed as shown in Scheme VIa. A preferred method uses Al(III) chloride in carbon disulfide at room temperature. The transformation of the carboxylate or dithiocarboxylate to the imidazoline is achieved by reaction with ethylenediamine, preferably by heating in a solvent such as ethanol. This reaction is catalyzed by traces of carbon disulfide.

Scheme VIa

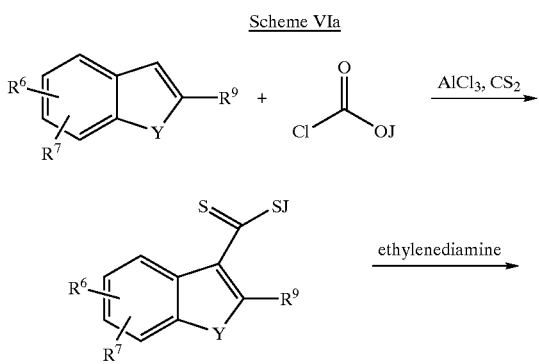

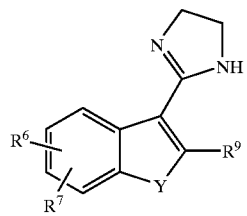

Benzofurans (Y=O) or benzothiophenes (Y=S) with an optionally substituted aryl or optionally substituted heteroaryl group in the 2-position may be prepared as illustrated in Scheme VIb. The unsubstituted heterocycles are prepared by methods known in the art, preferably by heating of (2,2-dialkoxy)ethoxybenzenes or (2,2-dialkoxy) ethylthiobenzenes, respectively, in chlorobenzene with polyphosphoric acid. These intermediates are converted to the corresponding benzofuran-2-yl or benzothiophen-2-yl boronic acids using standard conditions known in the art which use metallation with butyl lithium and trapping of the carbanions with esters of boronic acid like triisopropyl borate followed by an acid work-up procedure. The following aryl coupling reaction is carried out as described above for Scheme IIIh, preferably using a Suzuki coupling method, which preferably is carried out with aryl or heteroaryl bromides or iodides. In another procedure, 2-bromobenzofurans or 2-bromobenzothiophenes are prepared using standard bromination reagents known in the art, for example NBS. In a preferred method, the heterocycles are lithiated with butyl lithium followed by trapping of the carbanions with bromine. The 2-bromoheterocycles are converted to 2-aryl or 2-heteroaryl derivatives in aryl coupling reactions with optionally substituted aryl or optionally substituted heteroaryl boronic acids.

Scheme VIb

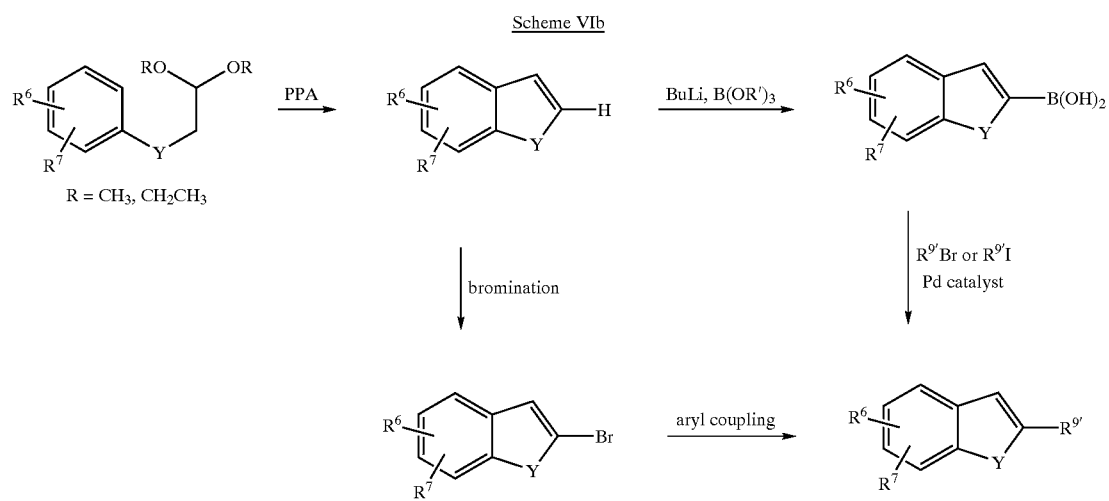

wherein R[9'] is optionally substituted aryl or optionally substituted heteroaryl.

Another route to benzofurans or benzothiophenes which are substituted in the 2-position by an optionally substituted aryl or optionally substituted heteroaryl group is illustrated in Scheme VIc. Phenols or thiophenols are reacted with arylacyl bromides or heteroarylacyl bromides to give the corresponding aryl- or heteroaryloxymethyl or aryl- or heteroarylthiomethylketones, respectively. The reaction is carried out in the presence of a base, for example potassium carbonate. These intermediates are heated under acidic conditions to give the corresponding bicyclic nuclei. A preferred method is heating in polyphosphoric acid (PPA).

Scheme VIc

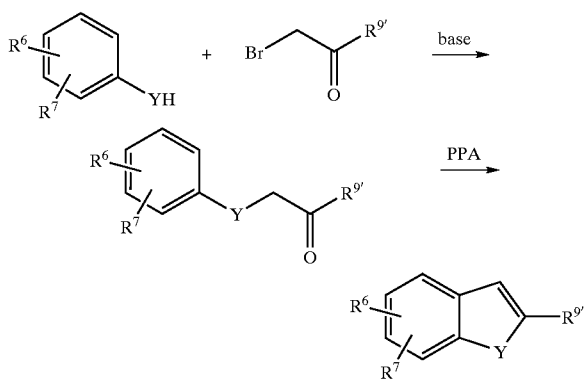

wherein R[9'] is optionally substituted aryl or optionally substituted heteroaryl.

Scheme VId describes a method for preparation of 2-methylbenzofurans or 2-methylbenzothiophenes. In the first step phenols or thiophenols, respectively, are alkylated with allyl halides which contain another leaving group L. A preferred group L is another halogen, and in a preferred method the alkylation is carried out by heating with 2,3-dichloropropene in acetone in the presence of a base, for example potassium carbonate. A preferred method for cyclization to form the heterocyclic rings is heating of the intermediate allylether or allythioether in N,N-diethylaniline. This reaction may or may not require an additional step for ring closure of the intermediate product derived from a Claisen rearrangement, for example by heating with hydrochloric acid.

Scheme VId

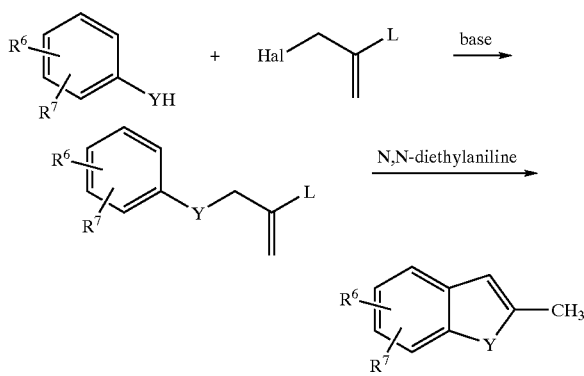

A particular method for the synthesis of benzofurans or benzothiophenes containing a 2-substituted ethyl group in position 2 of the nucleus is described in Scheme VIe.

2-Methylbenzofurans or 2-methylbenzothiophenes are brominated at the methyl group to give 2-bromomethyl derivatives by standard conditions known in the art used for benzylic brominations, preferably with NBS. These are converted to phosphonium salts by heating with phosphines, preferably by heating with triphenylphosphine to triphenylphosphonium bromides which react with aldehydes under standard conditions known in the art for Wittig reactions to give 2-vinylbenzofurans or 2-vinylbenzothiophenes. The corresponding ethyl derivatives are prepared by hydrogenation of the vinyl compounds. A preferred method uses borohydride/Ni(II) acetate, particularly borohydride which is fixed on an exchange resin. Such resins are familiar and readily commercially available from vendors known to the artisan, see for example, Bunin, B. A. (1998) The Combinatorial Index. Academic Press, San Diego. ISBN 0121413403 #10496; Gordon E. M. & Kerwin, J. F. J. (1998) Combinatorial Chemistry and Molecular Diversity in Drug Discovery. John Wiley & Sons, New York. ISBN 0471155187 #9827.

Scheme VIe

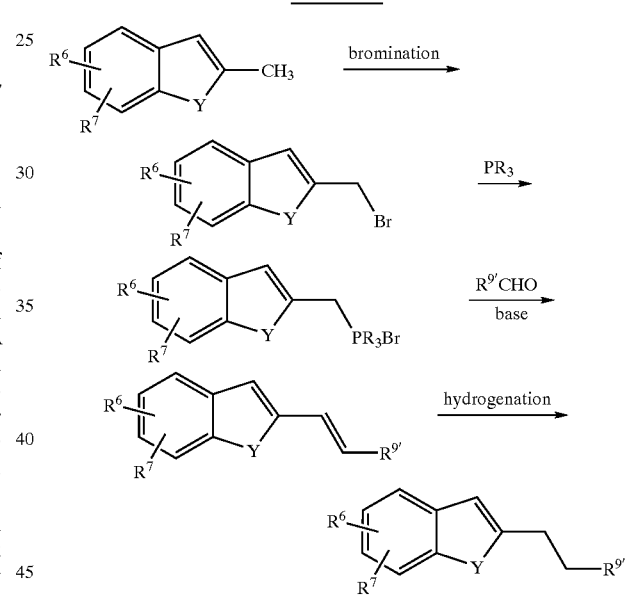

where R[9']CH$_2$CH$_2$— is R[9].

The synthesis of 3-chloro-2-(4,5-dihydro-1H-imidazol-2-yl)benzothiophenes is exemplified in Scheme VII.

Scheme VII

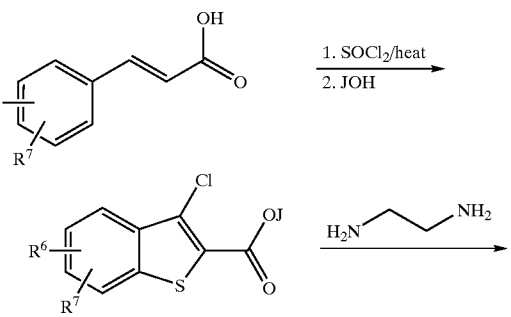

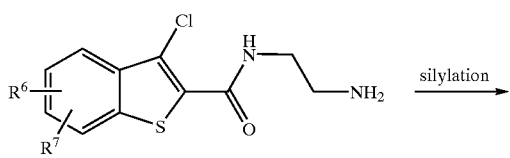

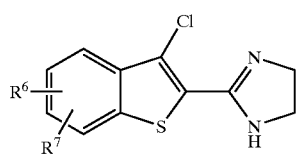

A procedure for the preparation of 3-optionally substituted aryl- and 3-optionally substituted heteroaryl-2-(4,5-dihydro)imidazol-2-yl benzothiophenes using a solid support is exemplified by Scheme VIIIa. The solid support illustrated in Scheme VIIIa may be a resin. Such resins and their use are familiar to the skilled artisan. Such resins can readily be obtained from commercial vendors, for example, but in no way limited to, Novabiochem, Catalog and Peptide Synthesis Handbook, 1999; Novabiochem, The Combinatorial Chemistry Catalog (March 1998); Bachem, Peptides and Biochemicals (1998). See also the following books available to the artisan via Amazon.com and from other vendors known to the skilled artisan, Terrett, N. K. (1998) Combinatorial Chemistry, Oxford University Press, New York ISBN 0198502206 #9825; Terrett, N. K. (1998) Combinatorial Chemistry, Oxford University Press, New York. ISBN0198502192#10542; Wilson, S. R., & Czarnik, A. W. (1997) Combinatorial Chemistry, Synthesis and Applications, John Wiley & Sons, Inc., New York. ISBN 047112687X#8349; and Jung, G (1996) Combinatorial Peptide and Nonpeptide Libraries: A Handbook, VCH, Weinheim; New York. ISBN 3527293809#8474.

Scheme VIIIa

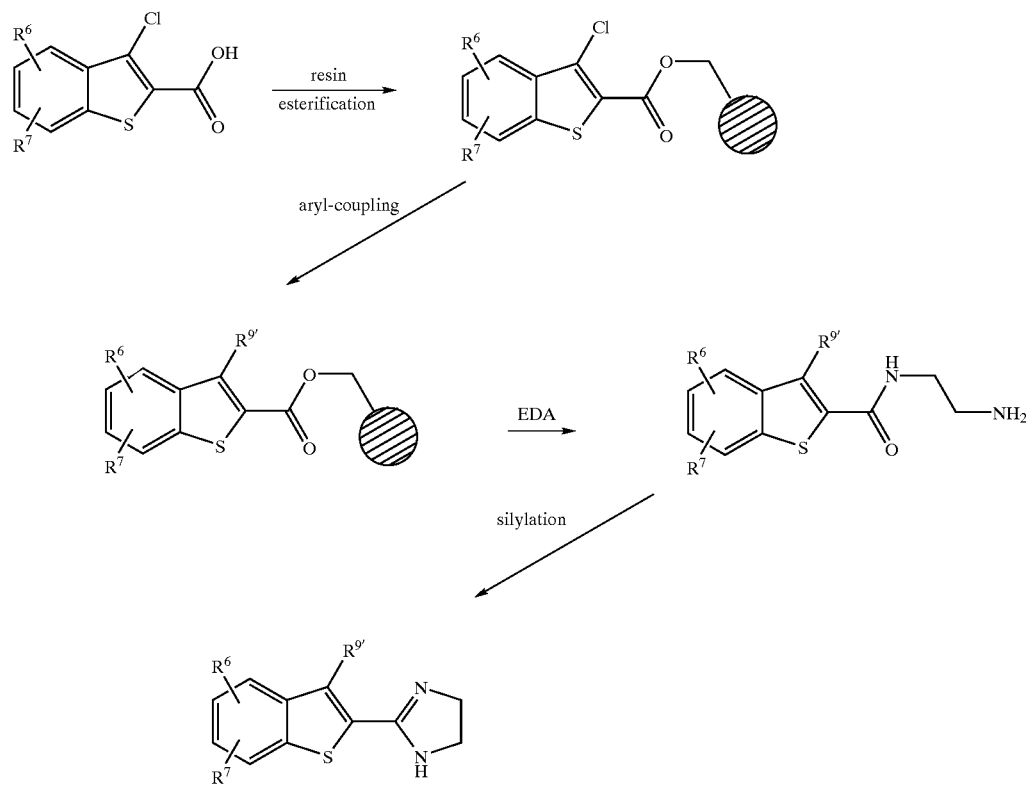

where $R^{9'}$ is optionally substituted aryl or optionally substituted heteroaryl.

The synthesis of several series of benzothiophenes of the present invention is exemplified in Scheme VIIIb.

Scheme VIIIb

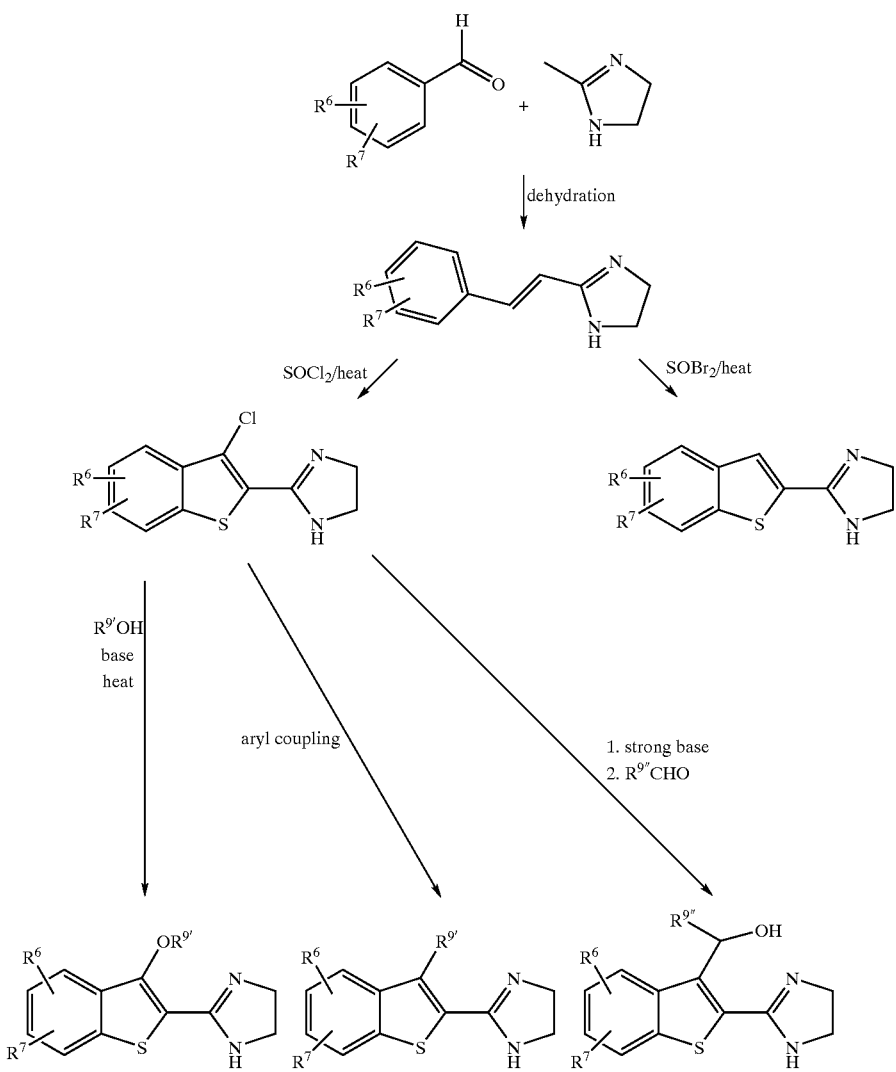

Wherein $R^{9'}$ is $C_{1-8}$ alkyl; $R^{9''}$ is aromatic or heteroaromatic; $R^{9'''}$ is $C_{1-8}$ alkyl, aromatic or heteroaromatic. As used in Scheme VIIIb, the term "strong base" has the meaning as recongized by the skilled artisan. A preferred strong base is an alkyl lithium and the most preferred strong base is n-BuLi.

A procedure for preparing indoles of the present invention which are substituted in the 2-position by an optionally substituted aryl group, or optionally substituted heteroaryl group is exemplified in Scheme IX. Introduction of the ethoxycarbonylmethyl group onto the nitrobenzene is achieved by methods known in the art, for example, as described in *Synthesis* 1988, 1007–9.

Scheme IX

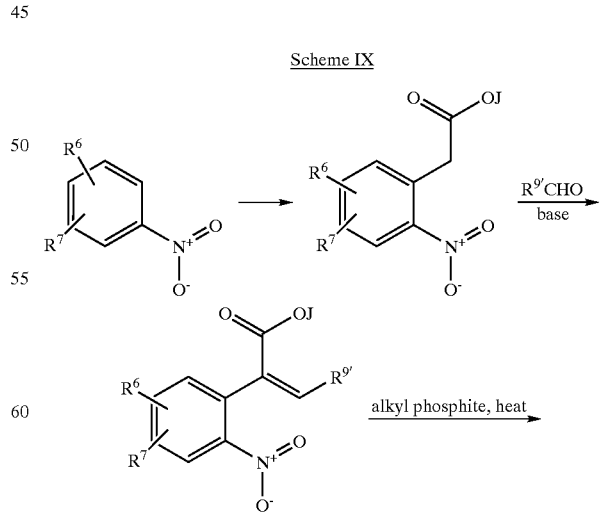

-continued

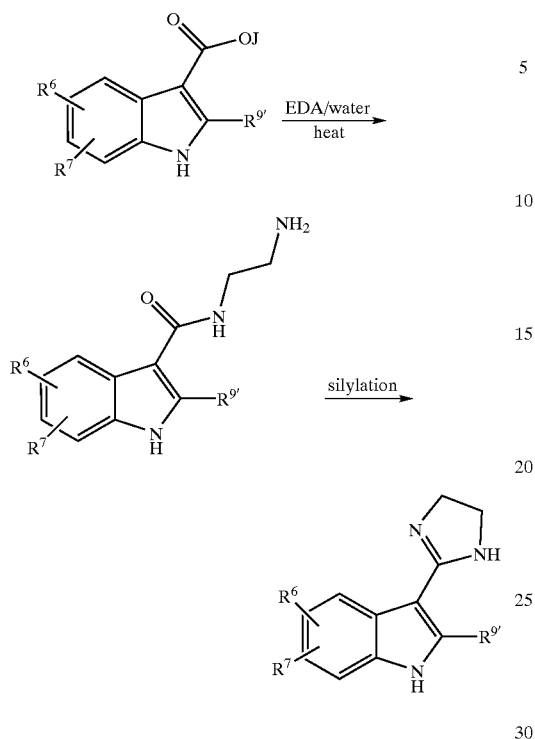

R[9'] is aryl or heteroaryl; all other terms are as defined by Formula I. The term "alkyl phosphite" shall have the meaning understood by the aritsan, and a most preferred alkyl phosphite is $P(OEt)_3$.

Scheme X exemplifies the preparation of 6-optionally substituted aryl- or optionally substituted heteroaryl-2-imidazolinyl napthalenes. Methyl-6-bromo-2-naphthoate is converted into the imidazoline as described, for example, in Example 18, followed by introduction of the aryl or heteroaryl moiety by Suzuki reaction. The Suzuki reaction may be accomplished by methods known in the art, or by procedures described herein.

Scheme X

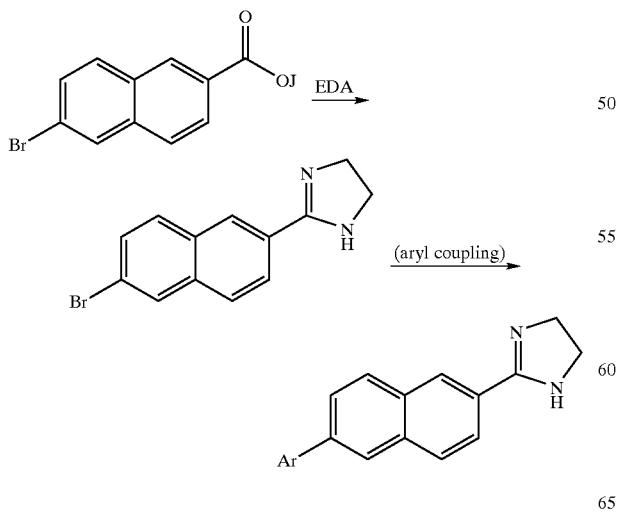

where Ar is optionally substituted aryl or optionally substituted heteroaryl.

Scheme XI illustrates a general route for the synthesis of 2-imidazolinyl quinolines, and Scheme XII illustrates a general route for the synthesis of 3-imidazolinylquinolines.

Scheme XI

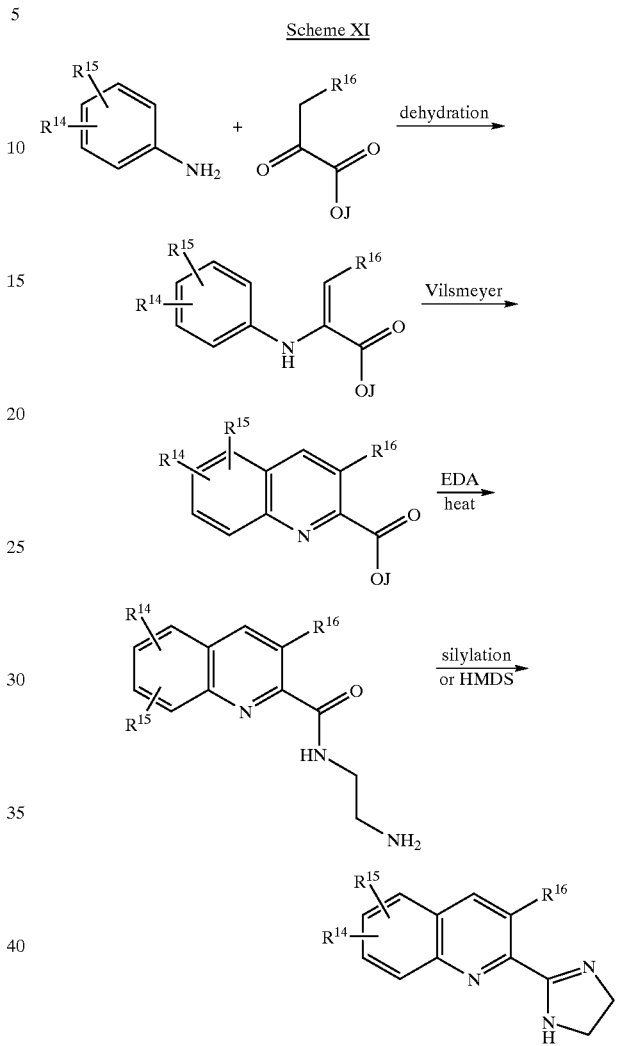

Scheme XII

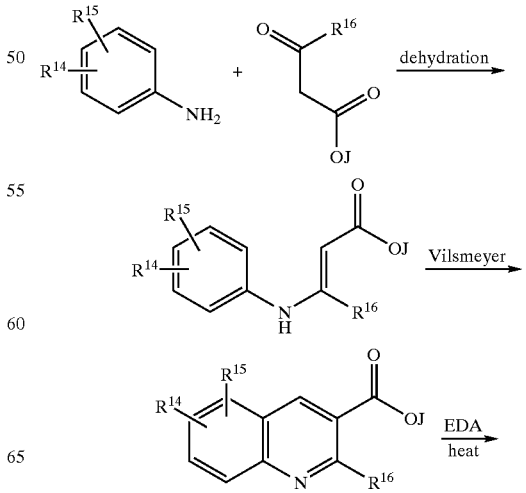

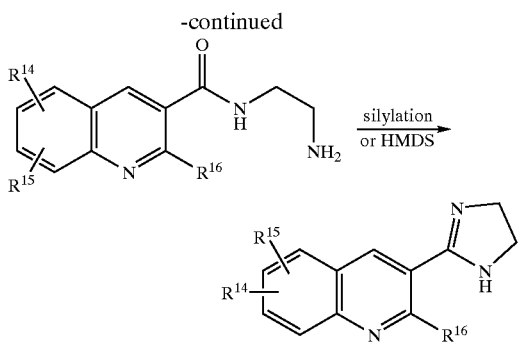

wherein J is $C_{1-8}$alkyl, aryl, or aryl $C_{1-8}$alkyl.

The artisan appreciates that, in some instances, desired isomeric forms may be obtained using separation methods which are generally known.

Compounds of Formula (I) have primary action during hyperglycemia in that they improve glucose tolerance without producing marked reduction in basal plasma glucose levels.

Compounds of the invention were active in screens for activity using assays based on the use of $BTC_6$ cells, for example as described by Poitout, V et al. *Diabetes* 44:306–313 (1995) and D'Ambra, R et al *Endocrinology*, 126: 2815–2822 (1990)] and rat Langerhans islets, for example as described by Lacy, P. E and Kostianovsky, M. *Diabetes* (1967), and as described in more detail in hereinbelow, and in an Intravenous Glucose Tolerance Test as described hereinbelow.

The invention further includes a method of treating diabetes in which an effective amount of a compound of formula (I) or a pharmaceutically acceptable salt or ester thereof is administered to a patient requiring such treatment.

Preparations and Examples

The following examples and preparations are provided merely to further illustrate the invention. The scope of the invention is not construed as merely consisting of the following examples. In the following examples and preparations, melting point, nuclear magnetic resonance spectra, mass spectra, high pressure liquid chromatography over silica gel, gas chromatography, N,N-dimethylformamide, palladium on charcoal, tetrahydrofuran, ethyl acetate, thin layer chromatography and elemental analysis are abbreviated M.Pt. or m.p., NMR MS, HPLC, GC, DMF, Pd/C, THF, EtOAc, TLC and EA respectively. The terms "EA", "TLC", "NMR", and "MS", when being utilised in the preparations, indicate that the data indicated was consistent with the desired structure. Reported melting points are uncorrected and yields are unoptimized.

Preparation 1

Ethyl (2,5-Dimethylindol-3-yl)acetate (X=Me, n=1)

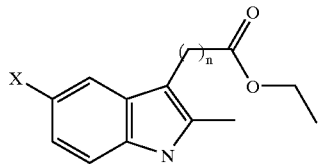

A suspension of 1.6 g (0.01 mol) of p-tolylhydrazine hydrochloride salt in 50 mL of EtOH was treated with ethanolic $NH_3$ to basify, heated n the water bath for 2 minutes, and then the $NH_4Cl$ salt formed was filtered off. the filtrate was concentrated to dryness and treated with 1.4 g (0.01 mol) of ethyl levulinate and 0.92 mL of $PCl_3$ (0.01 mol) in 25 mL of toluene at 130° C. for 4 hours. The reaction mixture was poured into an ice-water and extracted with ethyl acetate which was washed three times with brine to neutral. The extract was dried over $MgSO_4$, concentrated, and chromatographed with $CH_2Cl_2$ as an eluent to yield 1.2 g (48%) of the desired indolylacetate as an oil.

$^1$H NMR ($CDCl_3$) d 7.75 (br. s, 1H), 7.31 (s, 1H), 6.9 (d, J=8.0 Hz, 1H), 6.76 (d, J=8.0 Hz, 1H), 4.12 (q, J=7.0 Hz, 2H), 3.63 (s, 2H), 2.43 (s, 3H), 2.36 (s, 3H), 1.24 (t, J=7.0 Hz, 3H).

The following compounds were prepared from the appropriately substituted hydrazines essentially by the same procedure as described in Preparation 1.

Preparation 2

Ethyl (5-Fluoro-2-methylindol-3-yl)acetate (X=F, n=1). Yield: 21%

Preparation 3

Ethyl (5-Chloro2-methylindol-3-yl)acetate (X=Cl, n=1). Yield 40%

Preparation 4

Ethyl (5-Bromo-2-methylindol-3-yl)acetate (X=Br, n=1). Yield 23%

The following intermediates were prepared substantially in accordance with Preparation 1 from the corresponding hydrazine hydrochloride or hydrazine and ethyl 4-acetylbutyrate. The crude indolylpropionate esters obtained in high yields were used in the subsequent reaction without further purification.

Preparation 5

Ethyl 3-(2,5-Dimethylindol-3-yl)propionate (X=Me, n=2)

Yield: 96%; $^1$H NMR ($CDCl_3$) d 7.66 (br. s, 1H), 7.25 (s, 1H), 7.17 (d, J=8.0 Hz, 1H), 6.92 (d, 8.0 Hz, 1H), 4.11 (q, J=7.0 Hz, 2H), 2.99 (t, J=7.0 Hz, 2H), 2.60 (t, J=8.0 Hz, 2H), 2.44 (s, 3H), 2.36 (s, 3H), 1.24 (t, 7.0 Hz, 3H).

Preparation 6

Ethyl 3-(5-Fluoro-2-methylindol-3-yl)proprionate (X=F, n=2). Yield: 92%

Preparation 7

Ethyl 3-(5-Chloro-2-methylindol-3-yl)propionate (X=Cl, n=2). Yield: 96%

Preparation 8

Ethyl 3-(5-Bromo-2-methylindol-3-yl)propionate (X=Br, n=2). Yield: 62%

Preparation 9

Ethyl 3-(5-Trifluoromethyl-2-methylindol-3-yl) propionate (X=CF3, n=2). Yield: 90%

Preparation 10

(2-Methylindol-3-yl)acetic acid and (2-methyl-5-methoxyindol-3-yl)acetic acid were esterified with ethanolic HCl by conventional methods known in the art to give Ethyl (2-Methylindol-3-yl)acetate (X=H, n=1). Yield: 98%

Ethyl (2-Methyl-5-methoxyindol-3-yl)acetate (X=$OCH_3$, n=1). Yield: 99%

Preparation 11

Ethyl 3-(2-Methylindol-3-yl)propionate (X=H, n=2)

A solution of 1.6 g (10 mmol) of ethyl 4-acetylbutyrate and 1.1 g (10 mmol) of phenylhydrazine in 10 ml of ethanol was treated with 2 ml of ethanolic HCl solution at room temperature for 3 h, and then left standing in the refrigerator overnight. The solution was neutralized with ethanolic ammonia, concentrated, and chromatographed with dichloromethane as an eluent to afford 1.19 g (52%) of the indolylpropionate ester.

$^1$H NMR (CDCl$_3$) d 7.75 (br s, 1H), 7.36 (d, J=7.5 Hz, 1H), 7.24 (d, J=8 Hz, 1H), 7.11 (t, J=7 Hz, 1H), 7.07 (t, J=7 Hz, 1H), 4.10 (q, J=7 Hz, 2H), 3.03 (t, J=7.5 Hz, 2H), 2.61 (t, J=7.5 Hz, 2H), 2.38 (s, 3H), 1.21 (t, J=7 Hz, 3H).

Preparation 12

Ethyl 3-(2-Methyl-5-methoxyindol-3-yl)propionate (X=OCH$_3$, n=2)

The compound was prepared in a manner essentially similar to that of Preparation 11; Yield: 99%.

Preparation 13

Ethyl(2-Bromoindol-3-yl)acetate (X=H, n=1)

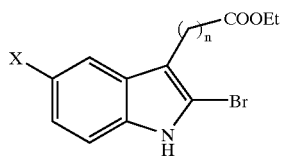

To a solution of 15.0 g (73.8 mmol) of ethyl (indol-3-yl) acetate in 75 ml of anhydrous dichloromethane at 0° C. was added 13.1 g (73.8 mmol) of NBS in small portions. The mixture was stirred at 0° C. for 3 h and then quickly concentrated under reduced pressure (argon was used to normalize the pressure after concentration to avoid decomposition due to the product's instability). Column chromatography with 99:1 toluene/ethanol afforded 10.5 g (50%) of the 2-bromoindole as a yellow oil.

$^1$H NMR (CDCl$_3$) d 8.22 (s, 1H), 7.35 (d, J=8.5 Hz, 1H), 7.20 (d, J=7.5 Hz, 1H), 7.16 (m, 2H), 4.16 (q, J=7 Hz, 2H), 3.72 (s, 2H), 1.25 (t, J=7 Hz, 3H); MS 281 (M$^+$).

The following intermediates were prepared in a manner essentially that of Preparation 13:

Preparation 14

Ethyl (2-Bromo-5-fluoroindol-3-yl)acetate (X=F, n=1)

yellow oil; yield 46%.

Preparation 15

Ethyl (2-Bromo-5-chloroindol-3-yl)acetate (X=Cl, n=1)

yellow oil which solidified rapidly upon standing; yield 47%

Preparation 16

Ethyl 3-(2-Bromoindol-3-yl)propionate (X=H, n=2)

yellow oil; yield 75%

$^1$H NMR (CDCl$_3$) d 8.11 (s, 1H), 7.53 (d, J=8 Hz, 1H), 7.26 (d, J=8 Hz, 1H), 7.13 (m, 2H), 4.12 (q, J=7 Hz, 2H), 3.06 (t, J=7.5 Hz, 2H), 2.64 (t, J=7.5 Hz, 2H), 1.23 (t, J=7 Hz, 3H); MS 295 (M$^+$).

Preparation 17

Ethyl (2-Phenylindol-3-yl)acetate (X, Y=H, n=1)

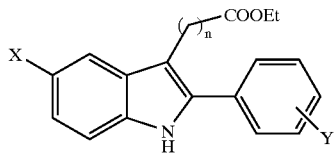

To a solution of 2.0 g (7.1 mmol) of ethyl (2-bromoindol-3-yl)acetate in 40 ml of dioxane was added under argon 1.2 g (0.11 mmol) of Pd(PPh$_3$)$_4$ and 13.3 ml of 2.0 M sodium carbonate. After stirring at room temperature for ca. 15 min, 1.3 g (11 mmol) of benzeneboronic acid was added, and the mixture was heated at 80° C. under argon overnight. The mixture was cooled to room temperature and solids were removed by filtration. The filtrate was concentrated and chromatographed on silica gel with toluene as an eluent to yield 1.6 g (81%) of the 2-phenyl indole as a yellow crystalline solid.

$^1$H NMR (CDCl$_3$) d 8.19 (s, 1H), 7.69–7.14 (m, 9H), 4.13 (q, J=7.5 Hz, 2H), 3.85 (s, 2H), 1.24 (t, J=7 Hz, 3H)

The following intermediates were prepared essentially in the same manner as described in Preparation 17. Substituted benzeneboronic acids, which are not commercially available, were prepared from corresponding substituted iodobenzenes and triisopropylborate Suzuki coupling reactions which are known in the art or as described herein.

Preparation 18

Ethyl [2-(2-Chlorophenyl)indol-3-yl]acetate (X=H, Y=2-Cl, n=1)

yellow oil; yield 61%

Preparation 19

Ethyl [2-(2-Trifluoromethylphenyl)indol-3-yl] acetate (X=H, Y=2-CF$_3$, n=1)

yellow oil; yield 63%

Preparation 20

Ethyl [2-(2,4-Dichlorophenyl)indol-3-yl]acetate (X=H, Y=2,4-C$_2$, n=1)

yellow oil; yield 60%

Preparation 21

Ethyl [2-(2-Chlorophenyl)-5-fluoroindol-3-yl]acetate (X=F, Y=2-Cl, n=1) amorphous solid; yield 94%

Preparation 22

Ethyl [5-Chloro-2-(2-chlorophenyl)indol-3-yl] acetate (X=Cl, Y=2-Cl, n=1)

yellow oil which solidified upon standing; yield 60%

Preparation 23

Ethyl 3-(2-Phenylindol-3-yl)propionate (X, Y=H, n=2)

oil; yield 66%

¹H NMR (CDCl₃) d 8.07 (s, 1H), 7.64–7.13 (m, 9H), 4.09 (q, J=7 Hz, 2H), 3.35 (t, J=8 Hz, 2H), 2.68 (t, J=8 Hz, 2H), 1.21 (t, J=7 Hz, 3H)

Preparation 24

Ethyl 3-[2-(2-Fluorophenyl)indol-3-yl]propionate (X=H, Y=2-F, n=2)

yellow oil; yield 63%

Preparation 25

Ethyl 3-[2-(2-Chlorophenyl)indol-3-yl]propionate (X=H, Y=2-Cl, n=2)

yellow oil; yield 60%

Preparation 26

Ethyl 3-[2-(2-Trifluoromethylphenyl)indol-3-yl] propionate (X=H, Y=2-CF₃, n=2)

yellow oil; yield 61%

Preparation 27

Ethyl 3-[2-(2,4-Dichlorophenyl)indol-3-yl] propionate (X=H, Y=2,4-Cl₂, n=2)

yellow resinous solid; yield 40%

Preparation 28

2-(5-Chloro-2-nitrophenyl)-3-(3-fluorophenyl) propionitrile (X=3-F)

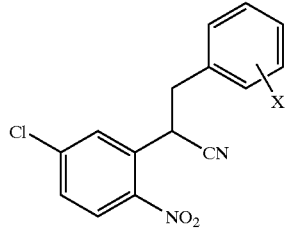

(5-Chloro-2-nitrophenyl)acetonitrile was prepared from 4-chloronitrobenzene and 4-chlorophenoxyacetonitrile according to procedure known in the art (M. Makosza, J. Winiarski, J. Org. Chem. 1984, 49, 1494). To a suspension of 13.8 g (0.1 mol) anhydrous potassium carbonate in 100 ml acetonitrile were added 100 mg 18-crown-6, 3.93 g (20.0 mmol) of (5-chloro-2-nitrophenyl)acetonitrile, and 4.15 g (21.95 mmol) 3-fluorobenzyl bromide, successively. It was stirred at room temperature overnight, and the solids were removed by filtration. The filtrate was concentrated under reduced pressure, and the residue was stirred with a small amount of ethanol to give the pale yellow crystalline title compound, which was collected by filtration, washed with cold ethanol, and dried in vacuo.

yield: 4.9 g (80%)

Except as noted, the following intermediates (Preparations 29–31) were prepared in essentially the same manner as described for Preparation 28, from (5-chloro-2-nitrophenyl)acetonitrile and the corresponding benzyl halides:

Preparation 29

2-(5-Chloro-2-nitrophenyl)-3-(3-trifluoromethylphenyl)propionitrile (X=3-CF₃)

yield: 52%; pale yellow crystalline solid.

Preparation 30

2-(5-Chloro-2-nitrophenyl)-3-(3-iodophenyl) propionitrile (X=3-I)

yield: 36%; pale yellow crystals

Preparation 31

2-(5-Chloro-2-nitrophenyl)-3-(4-iodophenyl) propionitrile (X=44)

The mixture was stirred for 4 h at room temperature, and the title compound was purified by chromatography on silica gel with hexane/ethyl acetate 7:3 to give a yellow oil, which slowly solidified upon standing.

yield: 98%

Preparation 32

5-Chloro-3-cyano-2-(3-fluorophenyl)-1-hydroxy-1H-indole (X=3-F)

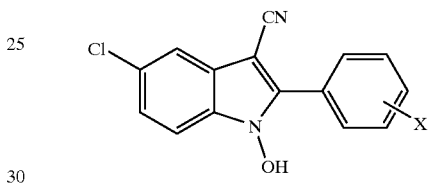

To a solution of 4.6 g (15.1 mmol) 1-(5-chloro-2-nitrophenyl)-2-(3-fluorophenyl)propionitrile in 75 ml dry DMSO were added 2.4 g (60 mmol) powdered sodium hydroxide. The mixture was stirred for 1 h at room temperature and poured with stirring into 800 ml 2N hydrochloric acid. The formed precipitate was collected by filtration, washed with water, and dried in vacuo. The title 1-hydroxyindole was purified by chromatography on silica gel with hexane/ethyl acetate 7:3 to give 3.6 g (83%) of a beige crystalline solid; MS 286 (M⁺).

The following intermediates (Preparations 33–35) were prepared essentially in the same manner as decribed above for Preparation 32:

Preparation 33

5-Chloro-3-cyano-1-hydroxy-2-(3-trifluoromethylphenyl)-1H-indole (X=3-CF₃)

yield: 68%; beige crystalline solid; MS 336 (M⁺).

Preparation 34

5-Chloro-3-cyano-1-hydroxy-2-(3-iodophenyl)-1H-indole (X=3-I)

yield: 98% of 1-hydroxyindole, which was used for the next step without further chromatographic purification; MS 394 (M⁺).

Preparation 35

5-Chloro-3-cyano-1-hydroxy-2-(4-iodophenyl)-1H-indole (X=4-I)

yield: 63%; browne crystalline solid.

Preparation 36

5-Chloro-3-cyano-2-(3-fluorophenyl)-1H-indole (X=3-F)

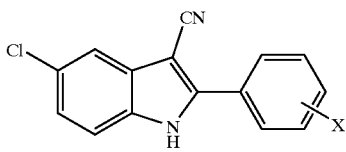

A mixture of 1.3 g (4.53 mmol) 5-chloro-3-cyano-2-(3-fluorophenyl)-1-hydroxy-1H-indole and 15 ml trimethyl phophite was heated for 4 h at 100° C. It was concentrated under reduced pressure, and the title indole was obtained from the residue by chromatography on silica gel with hexane/ethyl acetate 4:1. It was recrystallized by stirring with ethyl acetate to give 455 mg (37%) of a crystalline solid; MS 270 (M+).

The following 2-phenylindoles (Preparations 37–39) were prepared essentially in the same manner as decribed above for Preparation 36:

Preparation 37

5-Chloro-3-cyano-2-(3-trifluoromethylphenyl)-1H-indole (X=3-CF$_3$)

yield: 73%; crystallization by stirring with ethanol; MS 320 (M+).

Preparation 38

5-Chloro-3-cyano-2-(3-iodophenyl)-1H-indole (X=3-I)

The compound was isolated by crystallization from ethanol without further chromatographic purification.

yield: 51%; MS 378 (M+).

Preparation 39

5-Chloro-3-cyano-2-(4-iodophenyl)-1H-indole (X=4-I)

The compound was isolated in the same manner as the before mentioned 3-iodo isomer.

yield: 75%.

Preparation 40

Step A: 5-Chlorobenzofuran-2-boronic acid

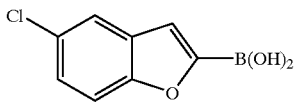

5-Chlorobenzofuran was prepared by heating 4-chlorophenoxyacetaldehyde dimethylacetal in polyphosphoric acid; yield: 73%.

To a solution of 8.8 g (57.7 mmol) 5-chlorobenzofuran in 250 ml dry ether were added 7.32 g (63.0 mmol) tetramethylethylenediamine (TMEDA). The solution was kept below −60° C. under argon, while 37.5 ml of a 1.6M solution of butyllithium in hexane was added dropwise. It was warmed to −10° C. during 45 min and stirred at this temperature for another 30 min. The mixture was cooled again below −60° C. followed by dropwise addition of 35.7 g (190 mmol) triisopropyl borate. After warming to room temperature the mixture was quenched with 70 ml 2N hydrochloric acid and stirred for 1 h. The organic layer was washed three times with 30 ml 2N hydrochloric acid, twice with water, and extracted with 2N sodium hydroxide solution, successively. The alkaline aqueous layer was brought to pH5 and extracted with tert.-butylmethylether. All organic layers were combined, dried over sodium sulfate, and concentrated in vacuo to give the pale yellow crystalline boronic acid which was used for the next step without further purification.

yield: 9.4 g (83%); MS 196 (M+).

Step B: 5-Chloro-2-(4-methoxyphenyl)benzofuran (X=4-OCH$_3$)

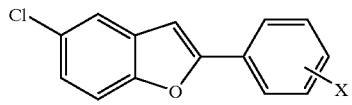

A mixture of 1.4 g (7.13 mmol) 5-chlorobenzofuranboronic acid, 1.24 g (5.30 mmol) 4-iodoanisole, 150 mg Pd(PPh$_3$)$_4$, 7.1 ml 1M aqueous sodium carbonate solution, and 25 ml 1,2-dimethoxyethane were heated in a sealed tube at 100° C. under argon overnight. It was cooled to room temperature and extracted with ethyl acetate. The organic layer was dried over sodium sulfate and concentrated under reduced pressure. 600 mg of the title benzofuran were obtained by crystallization from ethyl acetate and another 250 mg were obtained from the mother liquid after chromatography on silica gel with hexane.

total yield: 850 mg (62%)

The following compounds or Preparations 41–44 were prepared essentially in the same manner by Suzuki coupling reaction with the corresponding iodobenzenes:

Preparation 41

5-Chloro-2-(2-chlorophenyl)benzofuran (X=2-Cl)

yield: 600 mg (15.5%) from 3.5 g (14.7 mmol) 1-chloro-2-iodobenzene; colorless crystals, MS 262 (M+).

Preparation 42

5-Chloro-2-(3-chlorophenyl)benzofuran (X=3-Cl)

yield: 370 mg (27%).

Preparation 43

5-Chloro-2-(4-chlorophenyl)benzofuran (X=4-Cl)

yield: 1.06 g (76%).

Preparation 44

5-Chloro-2-(3-methylphenyl)benzofuran (X=3-CH$_3$)

yield: 850 mg (66%).

Preparation 45

Step A: 2-(4-Chlorophenylthio)-1-(4-methylphenyl)ethanone (X=Cl)

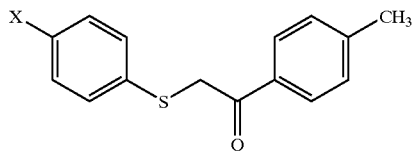

A mixture of 10.0 g (47 mmol) 4-methylphenacyl bromide, 6.8 g (47 mmol) 4-chlorothiophenol, and 6.5 g (47 mmol) anhydrous potassium carbonate in 100 ml dry DMF was stirred for 3 h at 80° C. It was filtered and the filtrate was concentrated under reduced pressure. The concentrate was stirred in water, and the resulting solid was filtered off, washed with water, and recrystallized from ethanol to give 10.7 g (82%) of the crude title compound.

Step B: 5-Chloro-2-(4-methylphenyl)benzo[b]thiophene (X=Cl)

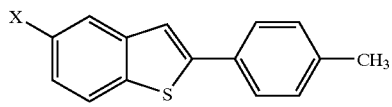

A mixture of 9.7 g (35 mmol) 2-(4-chlorophenylthio)-1-(4-methylphenyl)ethanone and 125 ml polyphosphoric acid were heated at 120° C. for 24 h. It was cooled and quenched with 125 g ice. After 30 min stirring 100 ml ethyl acetate were added, and it was stirred again vigorously. The formed precipitate was filtered with suction, washed with water and ethyl acetate, successively, and dried in vacuo to give 2.6 g (29%) of the title benzothiophene.

Preparation 46

2-(4-Fluorophenylthio)-1-(4-methylphenyl)ethanone (X=F)

The compound was prepared in a manner essentially similar to that described in Preparation 45, Step A, from 4-fluorothiophenol.

yield: 7.8 g (64%).

Preparation 47

5-Fluoro-2-(4-methylphenyl)benzo[b]thiophene (X=F)

The benzothiophene was prepared in a manner similar to that described in Preparation 45, Step B, from 7.8 g (30 mmol) 2-(4-fluorophenylthio)-1-(4-methylphenyl)ethanone. During the work-up procedure the organic layer was washed with saturated aqueous sodium bicarbonate solution, dried over sodium sulfate, and concentrated under reduced pressure. The title compound was recrystallized from ethyl acetate.

yield: 0.95 g (13%).

Preparation 48

Step A: 2-Bromo-5-chlorobenzo[b]thiophene (X=Cl)

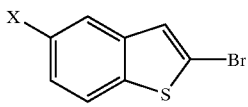

5-Chlorobenzothiophene was prepared by procedures known in the art (J. Heterocyclic Chem. 1988, 25, 1271). 1.68 g (9.96 mmol) of the compound were dissolved in 20 ml dry ether, and the solution was kept under argon at room temperature, while 6.25 ml (10 mmol) of a 1.6 M solution of butyl lithium in hexane was added dropwise. It was stirred for 30 min, cooled to −30° C. followed by slow addition of 1.60 g (10.0 mmol) bromine. After 30 min stirring at this temperature cooling was stopped, and the mixture was washed with aqueous sodium thiosulfate solution. The organic layer was dried over sodium sulfate and concentrated under reduced pressure, and the title benzothiophene was obtained after chromatography on silica gel with hexane to give 1.65 g (67%) of a colorless oil, which slowly solidified.

Step B: 5-Chloro-2-(2-chlorophenyl)benzo[b]thiophene (X=Cl, Y=2-Cl)

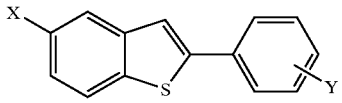

To a solution of 1.03 g (4.16 mmol) 2-bromo-5-chlorobenzothiophene in 12 ml DME under argon were added 1.0 g (6.4 mmol) 2-chlorobenzeneboronic acid, 88 mg Pd(PPh₃)₄, and 6.4 ml 1M aqueous sodium carbonate solution, and the mixture was heated overnight at 100° C. in a sealed tube. After cooling 20 ml water and 20 ml ethyl acetate were added followed by vigorous stirring. The organic layer was dried over sodium sulfate and concentrated in vacuo, and the title compound was purified by chromatography on silica gel with hexane/ethyl acetate 97:3 to give 1.1 g (95%) of a colorless oil, which slowly solidified; MS 278 (M⁺).

Preparation 49

2-Bromo-5-fluorobenzo[b]thiophene (X=F)

The compound was prepared in a manner essentially similar to that described in Preparation 48, Step A, from 9.12 g (59.9 mmol) 5-fluorobenzothiophene which was prepared by known methods (J. Heterocyclic Chem. 1993, 30, 1085).

yield: 5.35 g (39%); colorless oil, which slowly solidified

Preparation 50

2-(2-Chlorophenyl)-5-fluorobenzo[b]thiophene (X=F, Y=2-Cl)

The title compound was prepared in a manner similar to that described in Preparation 48, Step B, from 0.97 g (4.2 mmol) 2-bromo-5-fluorobenzothiophene.

yield: 0.59 g (53.5%); colorless crystalline solid; MS 262 (M⁺).

Preparation 51

5-Chloro-2-(4-methylphenyl)benzo[b]thiophene
(X=Cl, Y=4-CH$_3$)

The compound was prepared in the same manner as described in Preparation 48, Step B, from 2.06 g (8.32 mmol) 2-bromo-5-chlorobenzothiophene and 2.44 g (17.95 mmol) 4-methylbenzeneboronic acid and isolated by crystallization from ethyl acetate.

yield: 1.7 g (79%).

Preparation 52

Step A: 2-Chloro-3-(4-chlorophenoxy)propene
(A=O, X=Cl)

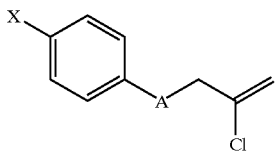

A mixture of 12.86 g (100 mmol) 4-chlorophenol, 11.1 g (100 mmol) 2,3-dichloropropene, and 16.6 g (120 mmol) anhydrous potassium carbonate in 50 ml acetone were heated with reflux overnight. Solids were removed by filtration and the filtrate was concentrated under reduced pressure. The residue was dissolved in 200 ml tert.-butylmethylether and washed twice with 100 ml 5% NaOH and with water, successively. The organic layer was dried over sodium sulfate and concentrated to give 13.4 g (66%) of the title allylether as a yellow oil.

Step B 5-Chloro-2-methylbenzofuran (A=O, X=Cl)

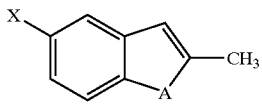

A mixture of 13.4 g (66.0 mmol) 2-chloro-3-(4-chlorophenoxy)propene and 75 ml N,N-diethylaniline were heated at 210° C. overnight. After cooling it was diluted with 400 ml tert.-butylmethylether and extracted three times with 250 ml 10% hydrochloric acid. The organic layer was dried over sodium sulfate and concentrated in vacuo to leave a brown oil, which was heated for 8 h at 85° C. with 65 ml concentrated hydrochloric acid. The mixture was diluted with 100 ml water and 200 ml tert.-butylether, brought to pH10 with 30% NaOH and stirred vigorously. The organic layer was dried over sodium sulfate, concentrated, and the residue chromatographed on silica gel with hexane to give 5.5 g (50%) of the title benzofuran as a colorless oil.

The following compounds, Preparations 53–55, were prepared essentially in the same manner as described for Preparation 52, Step A:

Preparation 53

2-Chloro-3-(4-fluorophenoxy)propene (A=O, X=F)

yield: 25.6 g (59%) from 26.0 g (232 mmol) 4-fluorophenol.

Preparation 54

2-Chloro-3-(4-chlorophenylthio)propene (A=S, X=Cl)

yield: 20.5 g (93%) from 14.6 g (100 mmol) 4-chlorothiophenol; yellow oil.

Preparation 55

2-Chloro-3-(4-fluorophenylthio)propene (A=S, X=F)

yield: 19.8 g (98%) from 12.8 g (100 mmol) 4-fluorothiophenol.

Except as noted, the following intermediates, Preparations 56–58 were prepared in essentially the same manner as described in Preparation 52, Step B:

Preparation 56

5-Fluoro-2-methylbenzofuran (A=O, X=F) from 25.6 g (137 mmol) 2-chloro-3-(4-fluorophenoxy)propene yield: 11.1 g (54%); colorless oil.

Preparation 57

5-Chloro-2-methylbenzo[b]thiophene (A=S, X=Cl) from 20.5 g (93.6 mmol) 2-chloro-3-(4-chlorophenylthio)propene with the modification that heating in hydrochloric acid was not required.

yield: 11.0 g (64%); colorless crystals

Preparation 58

5-Fluoro-2-methylbenzo]thiophene (A=S, X=F) from 19.8 g (97.7 mmol) 2-chloro-3-(4-fluorophenylthio)propene without heating in hydrochloric acid yield: 9.9 g (61%); colorless crystals

Preparation 59

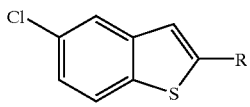

Step A: 2-Bromomethyl-5-chlorobenzo[b]thiophene (R=CH$_2$Br)

A solution of 2.73 g (14.95 mmol) 5-chloro-2-methylbenzothiophene and 2.67 g (15.0 mmol) NBS in 100 ml carbon tetrachloride was heated to 70° C. and a catalytic amount of dibenzoyl peroxide was added. After 30 min reflux solids were removed by filtration. The solvent was removed in vacuo and the residue was suspended in 100 ml hot hexane and filtered. The filtrate was evaporated to dryness to give 3.8 g (97%) of the title compound as a colorless solid.

Step B: [(5-Chlorobenzo[b]thiophen-2-yl)methyl] triphenylphosphonium Bromide (R=CH$_2$P(C$_6$H$_5$)$_3$Br)

A mixture of 2.50 g (9.56 mmol) 2-bromomethyl-5-chlorobenzo[b]thiophene and 2.51 g (9.57 mmol) triphenylphosphine in 50 ml xylene was heated at 140° C. After 3 h the reaction mixture was cooled to room temperature, and the phosphonium salt was filtered off, washed with xylene and tert.-butylmethylether, successively, and dried in vacuo.

yield: 2.7 g (54%)

Step C: 5-Chloro-2-(hepten-1-yl)benzo[b]thiophene
(R=—CH=CHC$_5$H$_{11}$)

To 20 ml 1,2-epoxybutane containing a small amount of potassium tert.-butoxide were added under argon 1.0 g (1.9 mmol) of the phosphonium salt and 0.19 g (1.9 mmol) of hexanal, and the mixture was stirred at 70° C. for 4 h. It was cooled to room temperature, evaporated, and the residue dissolved in diisopropylether. After filtration the filtrate was concentrated under reduced pressure. The concentrate was eluted through a column of silica gel with hexane and the eluant was concentrated to give 0.36 g (72%) of the title benzothiophene as a colorless foam; MS 264 (M$^+$).

Step D: 5-Chloro-2-heptylbenzo[b]thiophene
(=n-C$_7$H$_{15}$)

To a solution of 0.36 g (1.36 mmol) of 5-chloro-2-(hepten-1-yl)benzo[b]thiophene in 50 ml methanol were added 5 g (15 mmol) of borohydride exchange resin and 375 mg (1.51 mmol) Ni(II)acetate tetrahydrate, and the mixture was refluxed for 1 h. It was cooled to room temperature and the resin removed by filtration. The resin was heated twice with 50 ml methanol, and the combined filtrates were concentrated under reduced pressure. The residue was eluted through a column of silica gel with hexane, and the eluant was evaporated to give 175 mg (48%) of the title compound as a colorless resinous oil; MS 266 (M$^+$).

Preparation 60

Ethyl 5-Chloro-2-(4-methoxyphenyl)benzofuran-3-dithiocarboxylate (A=O, X=Cl, R=4-methoxyphenyl)

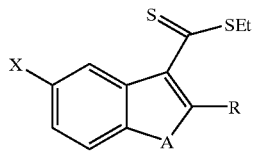

A suspension of 0.88 g (6.6 mmol) anhydrous AlCl$_3$ in 20 ml CS$_2$ was kept below 5° C., while 0.72 g (6.6 mmol) ethyl chloroformate was added. After 15 min at this temperature 0.85 g (3.3 mmol) 5-chloro-2-(4-methoxyphenyl) benzofuran in 10 ml CS$_2$ was added, and the mixture was stirred at room temperature for 5 h. It was quenched with crushed ice and extracted with ethyl acetate. The combined organic layers were dried over sodium sulfate and concentrated under reduced pressure. The title compound was obtained after chromatography on silica gel with hexane/ ethyl acetate 95:5 as a red oil which solidified slowly upon standing.

yield: 0.43 g (36%); MS 362 (M$^+$).

The following dithiocarboxylate intermediates, Preparations 61–73 were prepared essentially in the same manner as described for Preparation 60, from the corresponding benzofurans or benzothiophenes:

Preparation 61

Ethyl 5-Chloro-2-(2-chlorophenyl)benzofuran-3-dithiocarboxylate (A=O, X=Cl, R=2-chlorophenyl)

yield: 67%; orange oil.

Preparation 62

Ethyl 5-Chloro-2-(3-chlorophenyl)benzofuran-3-dithiocarboxylate (A=O, X=Cl, R=3-chlorophenyl)

yield: 70%; red oil which solidified upon standing; MS 366 (M$^+$).

Preparation 63

Ethyl 5-Chloro-2-(4-chlorophenyl)benzofuran-3-dithiocarboxylate (A=O, X=Cl, R=4-chlorophenyl)

yield: 15%; red oil; MS 366 (M$^+$).

Preparation 64

Ethyl 5-Chloro-2-(3-methylphenyl)benzofuran-3-dithiocarboxylate (A=O, X=Cl, R=3-methylphenyl)

yield: 72%; red oil; MS 346 (M$^+$).

Preparation 65

Ethyl 5-Chloro-2-methylbenzofuran-3-dithiocarboxylate (A=O, X=Cl, R=CH$_3$)

yield: 33%; red crystalline solid; MS 270 (M$^+$).

Preparation 66

Ethyl 5-Fluoro-2-methylbenzofuran-3-dithiocarboxylate (A=O, X=F, R=CH$_3$)

yield: 24%; red oil.

Preparation 67

Ethyl 5-Chloro-2-methylbenzo[b]thiophen-3-dithiocarboxylate (A=S, X=Cl, R=CH$_3$)

yield: 35%; red oil; MS 286 (M$^+$).

Preparation 68

Ethyl 5-Fluoro-2-methylbenzo[b]thiophen-3-dithiocarboxylate (A=S, X=F, R=CH$_3$)

yield: 32%; red oil; MS 270 (M$^+$).

Preparation 69

Ethyl 5-Chloro-2-(4-methylphenyl)benzo[b]thiophen-3-dithiocarboxylate (A=S, X=Cl, R=4-methylphenyl)

yield: 29%; red oil; MS 362 (M$^+$).

Preparation 70

Ethyl 5-Fluoro-2-(4-methylphenyl)benzo[b]thiophen-3-dithiocarboxylate (A=S, X=F, R=4-methylphenyl)

yield: 23%; red oil; MS 346 (M$^+$).

Preparation 71

Ethyl 5-Chloro-2-(2-chlorophenyl)benzo[b]thiophen-3-dithiocarboxylate (A=S, X=Cl, R=2-chlorophenyl)

yield: 6%; red oil; MS 347 (M$^{30}$ −Cl)

Preparation 72

Ethyl 2-(2-Chlorophenyl)-5-fluorobenzo[b]thiophen-3-dithiocarboxylate (A=S, X=F, R=2-chlorophenyl)

yield: 32%; red oil; MS 331 (M$^+$−Cl).

Preparation 73

Ethyl 5-Chloro-2-heptylbenzo[b]thiophen-3-dithiocarboxylate (A=S, X=Cl, R=n-C$_7$H$_{15}$)

yield: 66%; red oil.

Preparation 74

5-Chloro-1-(2-chlorobenzyl)-indole

The compound was prepared in essentially the same manner as described in Example 89, Step 1. Yield 61%, yellow oil. M.S. 276.

Preparation 75

5-Chloro-1-(3-chlorobenzyl)-indole

The compound was prepared in essentially the same manner as described in Example 89, Step 1. Yield 54%, yellow oil. M.S. 276.

Preparation 76

5-Chloro-1-(4-chlorobenzyl)indole

The compound was prepared in essentially the same manner as described in Example 89, Step 1. Yield 55%, yellow oil. M.S. 276.

Preparation 77

5-Chloro-2-(2-chlorobenzyl)-indole

The compound was prepared in essentially the same manner as described in Example 89, Step 2. Yield 48%, yellow oil. M.S. 276.

Preparation 78

5-Chloro-2-(3-chlorobenzyl)-indole

The compound was prepared in essentially the same manner as described in Example 89, Step 2. Yield 38%, yellow oil. M.S. 276.

Preparation 79

5-Chloro-2-(4-chlorobenzyl)-indole

The compound was prepared in essentially the same manner as described in Example 89, Step 2. Yield 44%, yellow oil. M.S. 276.

Preparation 80

5-Chloro-2-methyl-1-(2-chlorobenzyl)indole

The compound was prepared in essentially the same manner as described in Example 90, Step 1. Yield 28%, m.p. 83–84° C., M.S. 289.

Preparation 81

5-Chloro-2-methyl-1-(3-chlorobenzyl)indole

The compound was prepared in essentially the same manner as described in Example 90, Step 1. Yield 24%, m.p. 86–87° C., M.S. 289.

Preparation 82

5-Chloro-2-methyl-1-(4-chlorobenzyl)indole

The compound was prepared in essentially the same manner as described in Example 90, Step 1. Yield 28%, m.p. 93–94° C., M.S. 289.

Preparation 83

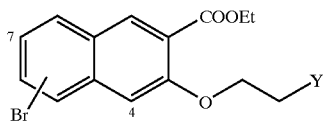

Ethyl 7-Bromo-3-(3-(tert.-butoxycarbonylamino)propoxy)naphthalen-2-carboxylate (Y=CH$_2$NHBoc)

A mixture of 3.8 g (12.88 mmol) ethyl 7-bromo-3-hydroxynaphthalen-2-carboxylate, 3.0 g (15.5 mmol) 1-(tert.-butoxycarbonylamino)-3-chloropropane (prepared according to Helv. Chim. Acta 76 (1993), 1644), 2.0 g (14.5 mmol) potassium carbonate, and a catalytic amount of potassium iodide in 20 ml dry DMF was stirred at 90° C. for 6 h. It was poured into water, extracted three times with ethyl acetate, and the combined organic layers were washed three times with water, dried over sodium sulfate, and concentrated in vacuo. The intermediate was purified by chromatography on silica gel with toluene/acetone 9:1 to give 5.8 g (100%) of a yellow oil, which solidified rapidly upon standing.

The following intermediates were prepared in substantially the same manner:

Ethyl 7-Bromo-3-(2-methylthioethoxy)naphthalen-2-carboxylate (Y=SCH$_3$) from ethyl 7-bromo-3-hydroxynaphthalen-2-carboxylate and 1-chloro-2-methylthioethane yield: 91%; MS 369 and 371 (M$^+$+1)

Ethyl 7-Bromo-3-(2-dimethylaminoethoxy)naphthalen-2-carboxylate (Y=N(CH$_3$)$_2$) from ethyl 7-bromo-3-hydroxynaphthalen-2-carboxylate and 1-chloro-2-dimethylaminoethane hydrochloride yield: 49%; MS 366 and 368 (M$^+$+1)

Ethyl 4-Bromo-3-(2-methylthioethoxy)naphthalen-2-carboxylate (Y=SCH$_3$) from ethyl 4-bromo-3-hydroxynaphthalen-2-carboxylate and 1-chloro-2-methylthioethane yield: 21%; MS 369 and 371 (M$^+$+1)

Ethyl 4-Bromo-3-propoxynaphthalen-2-carboxylate (Y=CH$_3$) from ethyl 4-bromo-3-hydroxynaphthalen-2-carboxylate and propyl iodide yield: 61%

Ethyl 4-Bromo-3-butoxynaphthalen-2-carboxylate (Y=CH$_2$CH$_3$)

The intermediate was prepared from ethyl 4-bromo-3-hydroxynaphthalen-2-carboxylate and butyl iodide in almost quantitative yield and used for the next step without further purification.

Preparation 84

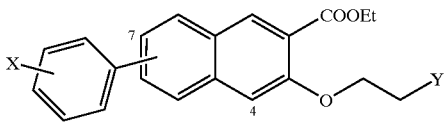

Ethyl 3-(3-(tert.-Butoxycarbonylamino)propoxy)-7-(4-methylphenyl)naphthalen-2-carboxylate
($X=4-CH_3$, $Y=CH_2NHBoc$)

To a solution of 6.6 g (14.6 mmol) of the bromonaphthalene in 100 ml dioxane were added under argon 22 ml 2M aqueous sodium carbonate solution and 2.0 g $Pd(PPh_3)_4$, successively. The mixture was stirred for 30 min at room temperature followed by addition of 3.0 g (22.0 mmol) 4-methylbenzeneboronic acid. After 6 h stirring at 80° C. the solvent was removed in vacuo, and the title intermediate was purified by chromatography on silica gel with toluene/acetone 97:3 to give 4.5 g (66.5%) of a yellow oil, which rapidly solidified upon standing.

The following intermediates were prepared in substantially the same manner:

Ethyl 7-(4-Fluorophenyl)-3-(2-methylthioethoxy)naphthalen-2-carboxylate ($X=4-F$, $Y=SCH_3$)

yield: 61%; pale yellow oil; MS 384 ($M^+$)

Ethyl 3-(2-Dimethylaminoethoxy)-7-(4-methylphenyl)naphthalen-2-carboxylate
($X=4-CH_3$, $Y=N(CH_3)_2$)

The compound crystallized by stirring of the residue with a small amount of ether and was used for the next step without further chromatographic purification; MS 378 ($M^++1$).

Ethyl 4-(2,4-Dichlorophenyl)-3-(2-methylthioethoxy)naphthalen-2-carboxylate
($X=2,4-C_2$, $Y=SCH_3$)

yield: 47.5%; MS 435 ($M^++1$)

Ethyl 4-(4-Chlorophenyl)-3-propoxynaphthalen-2-carboxylate ($X=4-Cl$, $Y=CH_3$)

yield: 77%

Ethyl 3-Butoxy-4-(4-chlorophenyl)naphthalen-2-carboxylate ($X=4Cl$, $Y=CH_2CH_3$)

yield: 95%; MS 383 ($M^++1$)

EXAMPLE 1

2-{2-[1-(2,4-Dichlorobenzyl)-1H-indol-3-yl]-ethyl}4,5-dihydro-1H-imidazole

To a solution of 3-(1H-indol-3-yl)-propionic acid ethyl ester (1.6 g, 7.3 mmol) in dry acetonitrile (25 ml) was added successively cesium carbonate (2.35 g, 7.3 mMol) and 2,4-dichlorobenzyl chloride (1.0 ml, 7.3 mMol). The mixture was heated to 70° C. for 15 hours and, after cooling, poured into water (250 ml) and extracted with methylene chloride. The combined organic solutions were dried over sodium sulphate and evaporated. The remaining brown oil was used in the next step without further purification.

A 2M solution of trimethyl aluminium in toluene (3.32 ml) was diluted with dry toluene (30 ml), cooled to 0° C. and 1,2-diaminoethane (0.43 ml) was added. The mixture was brought to ambient temperature and a solution of 2.5 g of 3-[1-(2,4-Dichlorobenzyl)-1H-indol-3-yl]-propionic acid ethyl ester in dry toluene (20 ml) was added slowly. The reaction mixture was refluxed for 15 hours, cooled and carefully hydrolysed with water (20 ml). The organic phase was separated, dried over sodium sulphate and evaporated. The crude product was purified by column chromatography using successively methylene chloride/ethanol/aqueous ammonium hydroxide 50:49:1 and 50:43:7 respectively to yield the titled product.

EXAMPLE 2

For clarification, as described in the following embodiments of Example 2, the variables 'X' and 'Y' are intended as illustrated:

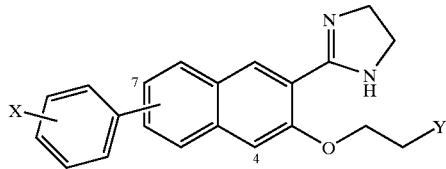

tert.-Butyl [3-(2-(4,5-Dihydro-1H-imidazol-2-yl)-7-(4methylphenyl)naphthalen-3-yloxy)propyl] carbamate ($X=4-CH_3$, $Y=CH_2NHBoc$)

A mixture of 2.4 g (5.18 mmol) of the ethyl naphthalen-2-carboxylate and 25 ml ethylenediamine was heated at 90° C. overnight. The excess of diamine was removed by distillation in vacuo, and the remaining crude 2-aminoethylamide was stirred with ethyl acetate, collected by filtration, and dried in vacuo to give 2.0 g (81%) of colorless crystals. 1.6 g (3.35 mmol) of the amide was heated with 6 ml HMDS under argon at 130° C. overnight. After cooling the mixture was diluted with ethanol and concentrated in vacuo. The title imidazoline crystallized from ethyl acetate to give 470 mg of pale yellow crystals along with 170 mg of a yellow resinous material, which was obtained after chromatography (dichloromethane/ethanol 7:3) from the mother liquid. total yield: 640 mg (42%), m.p. 106–109° C.; MS 459 ($M^+$)

The following imidazolines were prepared in substantially the same or a substantially similar manner:

EXAMPLE 2a

2-[7-(4-Fluorophenyl)-3-(2-methylthioethoxy)naphthalen-2-yl]-4,5-dihydro-1H-imidazole
($X=4-F$, $Y=SCH_3$)

The intermediate 2-aminoethylamide was obtained in 91% yield as a pale yellow crystalline solid (MS 399 ($M^++1$)) and cyclized by heating in HMDS.

yield: 14%; yellow crystalline solid, m.p. 136° C.; MS 381 or ($M^++1$)

EXAMPLE 2b

2-[3-(2-Dimethylaminoethoxy)-7-(4-methylphenyl)naphthalen-2-yl]-4,5-dihydro-1H-imidazole Dihydrochloride ($X=4-CH_3$, $Y=4-N(CH_3)_2$)

The intermediate 2-aminoethylamide crystallized by stirring with ether; yield: 46%; MS 392 ($M^++1$).

The title imidazoline was prepared by cyclization with HMDS followed by treatment of HCl in ether. It crystallized after dilution with ether.

yield: 3%; pale yellow crystals, m.p. 148° C.; MS 374 ($M^+$+1)

EXAMPLE 2c

2-[4-(2,4-Dichlorophenyl)-3-(2-methylthioethoxy) naphthalen-2-yl]-4,5-dihydro-1H-imidazole Hydrochloride (X=2,4-$Cl_2$, Y=$SCH_3$)

The intermediate 2-aminoethylamide was obtained in 67% yield; MS 449 ($M^+$+1).

The title hydrochloride was formed by stirring with HCl in ether/ethanol and crystallized after further addition of ether.

yield: 6.5%; yellow crystalline solid, m.p.182° C.; MS 431 ($M^+$+1)

EXAMPLE 2d

2-[4-(4-Chlorophenyl)-3-propoxynaphthalen-2-yl]-4, 5-dihydro-1H-imidazole (X=4-Cl, Y=$CH_3$)

The intermediate 2-aminoethylamide was obtained in quantitative yield after chromatographic purification with dichloromethane/ethanolic ammonia gradient 99:1 to 95:5, and the cyclization was achieved by stirring of a dichloromethane solution at room temperature for 14 days in the presence of TMS iodide and diethylaminomethyl polystyrene. The title compound was purified via column chromatography on silica gel with dichloromethane/ethanolic ammonia gradient 99:1 to 92:8.

yield: 29%; beige oil

EXAMPLE 2e

2-[3-Butoxy-4-(4-chlorophenyl)naphthalen-2-yl]-4, 5-dihydro-1H-imidazole (X=4-Cl, Y=$CH_2CH_3$)

The intermediate 2-aminoethylamide was obtained after chromatographic purification with dichloromethane/ ethanolic ammonia gradient 99:1 to 90:10 in 88% yield; MS 397 ($M^+$+1). The conversion to the imidazoline was achieved with TMS iodide and diethylaminomethyl polystyrene in the same manner as described herein by Example 2d. The title compound was purified by chromatography with dichloromethane followed by dichloromethane/ ethanolic ammonia 95:5.

yield: 39%; pale yellow oil; MS 379 ($M^+$+1)

EXAMPLE 2f

3-[2-(4,5-Dihydro-1H-imidazol-2-yl)-7-(4-methylphenyl)naphthalen-3-yloxy]propylamine Bistrifluoroacetate (X=4-$CH_3$, Y=$CH_2NH_2$)

A solution of 0.2 g (0.435 mmol) of the carbamate from the previous step in 2 ml dichloromethane and 1 ml trifluoroacetic acid was stirred overnight at room temperature. The solvent was removed in vacuo, and the title imidazoline crystallized from ethanol to give 110 mg of colorless crystals. Another crop of 100 mg of pale yellow crystals was obtained from the mother liquid with ethanol/ethyl acetate.

total yield: 210 mg (82%), m.p. 204–5° C. (dec.); MS 359 ($M^+$)

EXAMPLE 3

2-[7-(4-Fluorophenyl)-3-(2-methylsulfonylethoxy) naphthalen-2-yl]-4,5-dihydro-1H-imidazole (X=4-F, Y=$SO_2CH_3$)

As used herein, the variables "X" and "Y" refer to the structure illustrated in Example 2, above.

A solution of 100 mg (0.263 mmol) of 2-[7-(4-fluorophenyl)-3-(2-methylthioethoxy)naphthalen-2-yl]-4,5-dihydro-1H-imidazole in 3.5 ml methanol was cooled to 0° C., while 500 mg oxone in 2.7 ml water were added dropwise. It was stirred at room temperature for 3 h, concentrated under reduced pressure, diluted with water, and after adjusting to pH 7–8 with sodium bicarbonate solution extracted with dichloromethane. The organic layer was washed with brine and with water, successively, dried over sodium sulfate, and concentrated to leave the title sulfone as an oil, which crystallized by stirring with a small amount of ether.

yield: 13 mg (12%); yellow crystals, m.p. 127° C.; MS 413 ($M^+$+1)

EXAMPLE 4

2-(4-Methyl-3-propoxynaphthalen-2-yl)-4,5-dihydro-1H-imidazole

Step A: Methyl 4-Methyl-3-propoxynaphthalene-2-carboxylate

3-Hydroxy-4-methyl-2-naphthoic acid was prepared according to a literature procedure (Izv. Vyssh. Uchebn. Zaved., Khim. Khim. Tekhnol. 2 (1979), 786; Farmaco, Ed. Sci. 33 (1978), 822) and esterified with methanol using standard conditions to give methyl 3-hydroxy-4-methyl-2-naphthoate. A suspension of 300 mg (1.39 mmol) of this ester, 263 mg (1.55 mmol) propyl iodide, and 215 mg (1.55 mmol) of dry potassium carbonate in 60 ml of absolute butanone was stirred at 60° C. for 5 days. After addition of the same amounts of propyl iodide and potassium carbonate stirring was continued at 60° C. for another 2 days. The inorganic salts were filtered off, washed with acetone, and together with a small amount of silica gel the filtrate was evaporated to dryness. The remaining powder was applied to column chromatography on silica gel using hexane followed by a hexane/tert.-butylmethylether gradient up to 9:1.

yield: 280 mg (78%)

Step B: 2-(4-Methyl-3propoxynaphthalen-2-yl)-4,5-dihydro-1H-imidazole

A mixture of 280 mg (1.08 mmol) methyl 4-methyl-3-propoxynaphthalene-2-carboxylate and 2 ml ethylenediamine was heated at 80° C. overnight. The excess diamine was removed under reduced pressure and the intermediate 2-aminoethylamide purified by chromatography on silica gel with dichloromethane followed by dichloromethane/ ethanolic ammonia gradient up to 9:1.

yield: 270 mg (87%)

A mixture of 60 mg (0.21 mmol) of the amide, 200 mg (0.6 mmol) diethylaminomethyl polystyrene resin and 86 μl (0.6 mmol) TMS iodide in 2 ml dichloromethane was stirred at room temperature for 5 days. After addition of another 100 mg of the resin and 43 μl of the iodide stirring was continued for 7 days. The resin was removed by filtration, washed with dichloromethane and ethanol, successively, and the filtrate was concentrated under reduced pressure. The title compound was obtained after chromatography on silica gel with dichloromethane/ethanolic ammonia 9:1.

yield: 23 mg (41%); beige crystalline solid

EXAMPLE 5

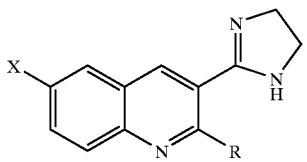

3-(4,5-Dihydro-1H-imidazol-2-yl)-2-phenylquinoline (X=H, R=phenyl)

As used herein, the variables "X" and "R" refer to the structure illustrated above herein in Example 5.

Step 1: 2-Phenylquinoline-3-carbaldehyde

A solution of 960 mg (5 mmol) of 2-chloroquinolin-3-carbaldehyde, 570 mg (0.5 mmol) of Pd(PPh$_3$)$_4$, and 1.2 g of benzeneboronic acid in a mixture of 7.5 ml of 2M aqueous sodium carbonate solution and 20 ml of dioxane was heated for 40 h to 95° C. It was extracted with ethyl acetate, and the organic layer was dried and evaporated. The residue was chromatographed on silica gel with a hexane/ethyl acetate gradient 98:2 to 90:10 to give 1.05 g (90%) of the title aldehyde.

Step 2: 3-(4,5-Dihydro-1H-imidazol-2-yl)-2-phenylquinoline

A solution of 100 mg (0.366 mmol) of the aldehyde from the previous step and 0.25 ml of ethylenediamine in 3 ml of nitrobenzene was heated for 60 h at 150° C. The solvent was removed by flash chromatography on silica gel using hexane as the eluent. After evaporation the residue was purified via column chromatography on silica gel with dichloromethane/ethanolic ammonia gradient 99:1 to 90:10.

yield: 9 mg (7%); brown oil

The following two examples were prepared in substantially the same manner by Suzuki coupling reaction with 2-chloroquinoline-3-carbaldehyde followed by formation of the imidazoline:

EXAMPLE 5a 3-(4,5-Dihydro-1H-imidazol-2-yl)-2-(4-methylphenyl)quinoline (X=H, R=4-methylphenyl)
beige amorphous solid

EXAMPLE 5b 2-(Benzofuran-2-yl)-3-(4,5-dihydro-1H-imidazol-2-yl)quinoline (X=H, R=benzofuran-2-yl)
beige amorphous solid In addition to the corresponding imidazolines the following imidazoles have been isolated from the reaction mixture after chromatographic separation:

EXAMPLE 5c

3(1H-Imidazol-2-yl)-2-phenylquinoline
brown amorphous solid

EXAMPLE 5d 2-(Benzofuran-2-yl)-3(1H-imidazol-2-yl)quinoline
brown oil

EXAMPLE 6

5-Chloro-2-methyl-3-(4,5-dihydro-1-H-imidazol-2-yl)-1H-indole

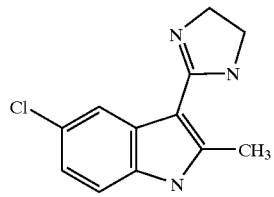

A mixture of 5-chloro-2-methylindole (30.1 g; 0.18 mole) and 1-acetyl-imidazolidine-2-one (24 g; 0.18 mole) was added to phosphorous oxychloride (178 ml) and heated to 50° C. After 5 hours, phosphorous oxychloride was evaporated. The residue was treated with ethanol (250 ml) cautiously and maintained at reflux for 3.5 hours. The mixture was concentrated under reduced pressure to half of the orignal volume to obtain a precipitate, which was collected on a filter. The crystalline residue was treated with water, washed with ethylacetate, treated with 2N sodium hydroxide to pH 11 and stirred overnight. The precipitate was filtered, washed with water and t-butylmethylether and dried to give product (10.9 g, 26%), m.p. 213° C.

$^1$H-NMR(DMSO): d 2.5 (s, 3H, CH$_{-31}$), 3.55 (s, 4H, 2×CH$_{-2}$), 6.30 (b, 1H, imidazolin), 7.04 (d, 1H 8.00 (s, 1H, H-4), 11.57 (b, 1H, NH-indol); MS (Ei 70 eV) m/Z 233M+.

The following examples were prepared in substantial accordance with Example 6 and the procedures and methods disclosed herein.

| Ex. # | MolStructure | | yield | mp. | MS |
|---|---|---|---|---|---|
| 6a | | 2-Methyl-3-(4,5-dihydro-1H-imidazol-2-yl)-1H-indole Hydrochloride | 50% | 301–303° C. | 199 M+ |

-continued

| Ex. # | MolStructure | | yield | mp. | MS |
|---|---|---|---|---|---|
| 6b | | 3-(4,5-dihydro-1H-imidazol-2-yl)-2,5-dimethyl-1H-indole Hydrochloride | 51.30% | >290° C. | 278 M+ |
| 6c | | 5-Methoxy-3-(4,5-dihydro-1H-imidazol-2-yl)-1H-indole | 14.60% | 214° C. | 229 M+ |
| 6d | | 3-(4,5-Dihydro-1H-imidazol-2-yl)-5-fluoro-2-methyl-1H-indole Hydrochloride | 46% | amorph | 217 M+ |
| 6e | | 2-Phenyl-3-(4,5-dihydro-1H-imidazol-2-yl)-1H-indole Hydrochloride | 63.90% | >300° C. | 261 M+ |
| 6f | | 5-Nitro-3-(4,5-dihydro-1H-imidazol-2-yl)-2-methyl-1H-indole Hydrochloride | 23% | >350° C. | 244 M+ |
| 6g | | 3-(4,5-Dihydro-1H-imidazol-2-yl)-2-methyl-5-trifluoromethyl-1H-indole Hydrochloride | 25% | 350° C. | 267 M+ |

-continued

| Ex. # | MolStructure | | yield | mp. | MS |
|---|---|---|---|---|---|
| 6h | | 5-Bromo-3-(4,5-dihydro-1H-imidazol-2-yl)-2-methyl-1H-indole Hydrochloride | 80% | >350° C. | 277 M+ |
| 6i | | 5-Chloro-3-(4,5-dihydro-1H-imidazol-2-yl)-1,2-dimethyl-1H-indole | 9.60% | 189° C. | 247 M+ |
| 6j | | 5-Chloro-3-(4,5-dihydro-1H-imidazol-2-yl)-2-phenyl-1H-indole Hydrochloride | 60.20% | >300° C. | 294 M+ |
| 6k | | 4-Chloro-3-(4,5-dihydro-1H-imidazol-2-yl)-2-methyl-1H-indole Hydrochloride | 66.00% | >250° C. | 233 M+ |
| 6l | | 6-Chloro-3-(4,5-dihydro-1H-imidazol-2-yl)-2-methyl-1H-indole Hydrochloride | 60% | >300° C. | 233 M+ |
| 6m | | 3-(4,5-Dihydro-1H-imidazol-2-yl)-5-iodo-2-methyl-1H-indole Hydrochloride | 63% | >300° C. | 325 M+ |

-continued

| Ex. # | MolStructure | | yield | mp. | MS |
|---|---|---|---|---|---|
| 6n | 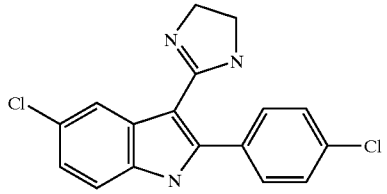 | 5-Chloro-2-(4-chlorophenyl)-3-(4,5-dihydro-1H-imidazol-2-yl)-1H-indole Hydrochloride | 40.90% | >320° C. | 330 M+ |
| 6o | 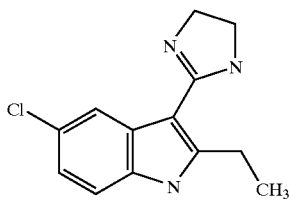 | 5-Chloro-3-(4,5-dihydro-1H-imidazol-2-yl)-2-ethyl-1H-indole | 7.10% | 176° C. | 247 M+ |
| 6p | 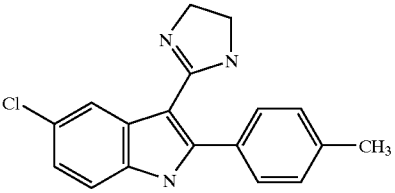 | 5-Chloro-3-(4,5-dihydro-1H-imidazol-2-yl)-2-(4-methylphenyl)-1H-indole Hydrochloride | 17.40% | >300° C. | 308 M+ |
| 6q | 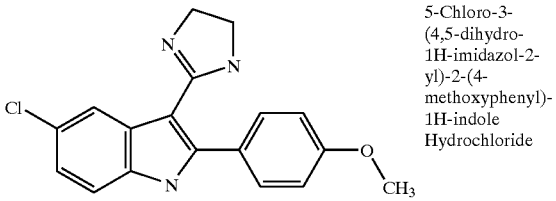 | 5-Chloro-3-(4,5-dihydro-1H-imidazol-2-yl)-2-(4-methoxyphenyl)-1H-indole Hydrochloride | 64.80% | 347° C. | 326 [M + H]+ |
| 6r | 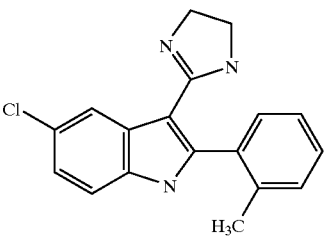 | 5-Chloro-3-(4,5-dihydro-1H-imidazol-2-yl)-2-(2-methylphenyl)-1H-indole | 15.80% | 245° C. | 309 M+ |
| 6s | 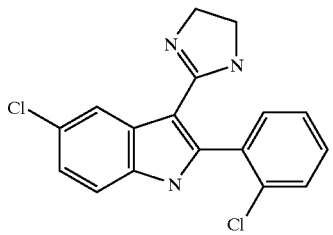 | 5-Chloro-2-(2-chlorophenyl)-3-(4,5-dihydro-1H-imidazol-2-yl)-1H-indole | 6% | 257° C. | 330 M+ |

| Ex. # | MolStructure | | yield | mp. | MS |
|---|---|---|---|---|---|
| 6t | | 3-(4,5-Dihydro-1H-imidazol-2-yl)-5-fluoro-2-(4-methylphenyl)-1H-indole Hydrochloride | 19% | >310° C. | 293 M+ |
| 6u | | 5,7-Dichloro-3-(4,5-dihydro-1H-imidazol-2-yl)-2-phenyl-1H-indole Hydrochloride | 12% | >330° C. | 330 M+ |
| 6v | | 5-Chloro-3-(4,5-dihydro-1H-imidazol-2-yl)-2-(5-methylfuran-2-yl)-1H-indole Hydrochloride | 16.50% | >310° C. | 299 M+ |
| 6w | | 5-Chloro-3-(4,5-dihydro-1H-imidazol-2-yl)-2-(2-thienyl)-1H-indole Hydrochloride | 62.80% | >310° C. | 301 M+ |
| 6x | | 2-(2-Bromophenyl)-5-chloro-3-(4,5-dihydro-1H-imidazol-2-yl)-1H-indole | 2.30% | 201–202° C. | 374 M+ |

| Ex. # | MolStructure | | yield | mp. | MS |
|---|---|---|---|---|---|
| 6y | | 5-Chloro-3-(4,5-dihydro-1H-imidazol-2-yl)-2-(3-methyl-2-thienyl)-1H-indole | 34.30% | 251° C. | 314 M+ |

| Structure and E.g. # | Name | yield % | MS M+ | mp ° C. |
|---|---|---|---|---|
| 6z | 3-(4,5-Dihydro-1H-imidazol-2-yl)-7-bromo-2-methyl-1H-indole Hydrochloride | 40% | 278 | >320 |
| 6aa | 3-(4,5-Dihydro-1H-imidazol-2-yl)-5-chloro-2-(4-Chlorphenyl)-1H-indole Hydrochloride | 56% | 330 | >310 |
| 6ab | 3-(4,5-Dihydro-1H-imidazol-2-yl)-5-cyano-2-methyl-1H-indole Hydrochloride | 36% | 224 | >300 |
| 6ac | 3-(4,5-Dihydro-1H-imidazol-2-yl)-5-chloro-2-(4-methylphenyl)-1H-indole Hydrochloride | 56% | 310 | >300 |

-continued

| Structure and E.g. # | Name | yield % | MS M+ | mp °C. |
|---|---|---|---|---|
| 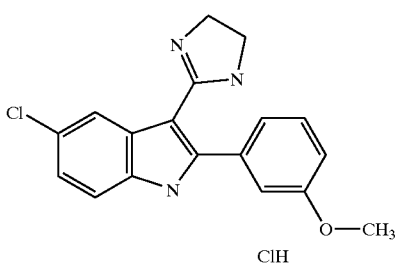 6ad | 3-(4,5-Dihydro-1H-imidazol-2-yl)-5-chloro-2-(3-methoxyphenyl)-1H-indole Hydrochloride | 54% | 326 | 317 |
| 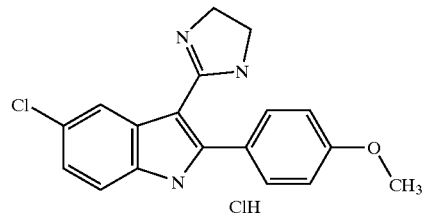 6ae | 3-(4,5-Dihydro-1H-imidazol-2-yl)-5-chloro-2-(4-methoxyphenyl)-1H-indole Hydrochloride | 45% | 326 | 347 |
| 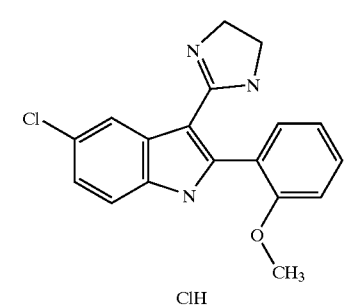 6af | 3-(4,5-Dihydro-1H-imidazol-2-yl)-5-chloro-2-(2-methoxyphenyl)-1H-indole Hydrochloride | 48% | 326 | 242 |
| 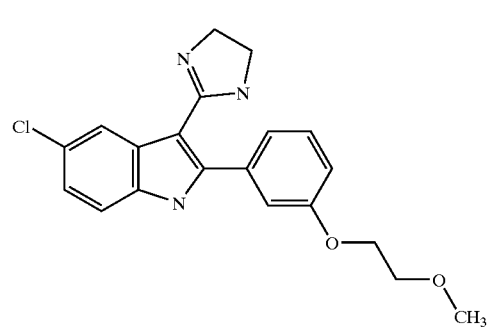 6ag | 3-(4,5-Dihydro-1H-imidazol-2-yl)-5-chloro-2-(3-methoxyethoxyphenyl)-1H-indole | 56% | 370 | 178 |
| 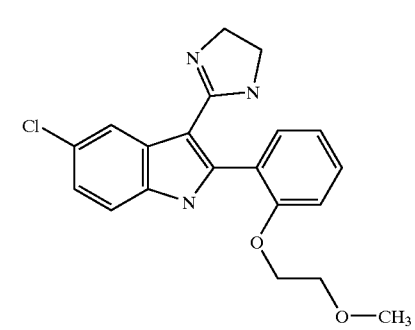 6ah | 3-(4,5-Dihydro-1H-imidazol-2-yl)-5-chloro-2-(2-methoxyethoxyphenyl)-1H-indole | 48% | 333 | >242 |

-continued

| Structure and E.g. # | Name | yield % | MS M+ | mp °C. |
|---|---|---|---|---|
| 6ai | 3-(4,5-Dihydro-1H-imidazol-2-yl)-5-chloro-2-(4-ethoxyphenyl)-1H-indole Hydrochloride | 54% | 340 | >300 |
| 6aj | 3-(4,5-Dihydro-1H-imidazol-2-yl)-5-chloro-2-(2-methylphenyl)-1H-indole | 73% | 310 | 245 |
| 6ak | 3-(4,5-Dihydro-1H-imidazol-2-yl)-5-chloro-2-(3-methylphenyl)-1H-indole Hydrochloride | 68% | 310 | >320 |
| 6al | 3-(4,5-Dihydro-1H-imidazol-2-yl)-5-chloro-2-(4-methoxyethoxyphenyl)-1H-indole Hydrochloride | 62% | 370 | 335 |
| 6am | 3-(4,5-Dihydro-1H-imidazol-2-yl)-5-chloro-2-(2-chlorophenyl)-1H-indole | 56% | 330 | 257 |

-continued

| Structure and E.g. # | Name | yield % | MS M+ | mp °C. |
|---|---|---|---|---|
| 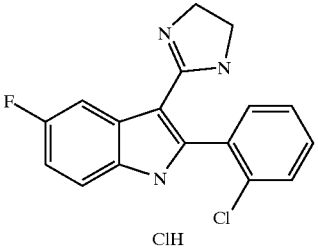 6an | 3-(4,5-Dihydro-1H-imidazol-2-yl)-5-fluoro-2-(2-chlorophenyl)-1H-indole Hydrochloride | 55% | 314 | 257 (Z) |
| 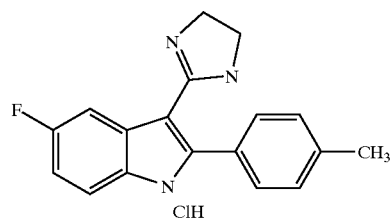 6ao | 3-(4,5-Dihydro-1H-imidazol-2-yl)-5-fluoro-2-(2-chlorophenyl)-1H-indole Hydrochloride | 58% | 293 | >310 |
| 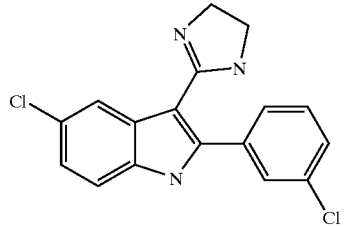 6ap | 3-(4,5-Dihydro-1H-imidazol-2-yl)-5-chloro-2-(3-chlorophenyl)-1H-indole | 58% | 330 | 258 |
| 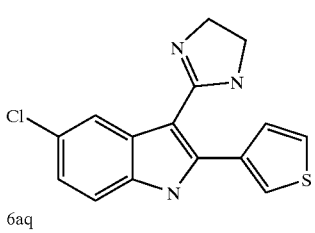 6aq | 3-(4,5-Dihydro-1H-imidazol-2-yl)-5-chloro-2-(3-thienyl)-1H-indole | 32% | 302 | 216 |
| 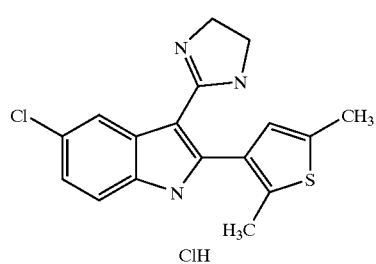 6ar | 3-(4,5-Dihydro-1H-imidazol-2-yl)-5-chloro-2-(2,5-dimethyl-thien-3-yl)-1H-indole Hydrochloride | 34% | 330 | 265–266 |

-continued

| Structure and E.g. # | Name | yield % | MS M+ | mp ° C. |
|---|---|---|---|---|
| 6as | 3-(4,5-Dihydro-1H-imidazol-2-yl)-5-chloro-2-(cyclohexen-2-yl)-1H-indole Hydrochloride | 45% | 300 | >310 |
| 6at | 3-(4,5-Dihydro-1H-imidazol-2-yl)-5-chloro-2-(2,5-dichloro-thien-3-yl)-1H-indole Hydrochloride | 34% | 371 | >310 |
| 6au | 3-(4,5-Dihydro-1H-imidazol-2-yl)-5-chloro-2-(2-chlorophenyl)-1H-indole Hydrochloride | 66% | 330 | >310 |
| 6av | 3-(4,5-Dihydro-1H-imidazol-2-yl)-5-chloro-2-(cyclohexan)-1H-indole Hydrochloride | 44% | 302 | >310 |
| 6aw | 3-(4,5-Dihydro-1H-imidazol-2-yl)-5-chloro-2-(2-fluorophenyl)-1H-indole Hydrochloride | 58% | 314 | >300 |

-continued
| Structure and E.g. # | Name | yield % | MS M+ | mp ° C. |
|---|---|---|---|---|
| 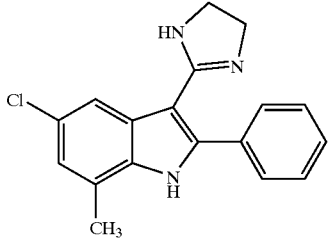 6ax | 3-(4,5-Dihydro-1H-imidazol-2-yl)-5-chloro-7-methyl-2-phenyl-1H-indole | 44% | 310 | 254–256 |
| 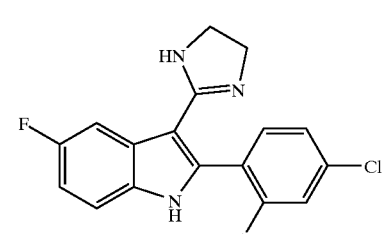 6ay | 3-(4,5-Dihydro-1H-imidazol-2-yl)-5-fluoro-2-(2,4-dichlorophenyl)-1H-indole | 56% | 348 | >340 |
| 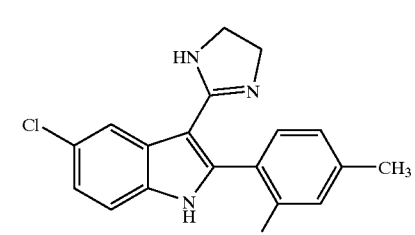 6az | 3-(4,5-Dihydro-1H-imidazol-2-yl)-5-chloro-2-(2,4-dimethylphenyl)-1H-indole | 46% | 324 | 277–279 |
| 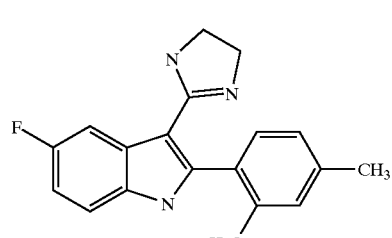 6ba | 3-(4,5-Dihydro-1H-imidazol-2-yl)-5-fluoro-2-(2,4-dimethylphenyl)-1H-indole | 55% | 307 | 229 (Z) |
| 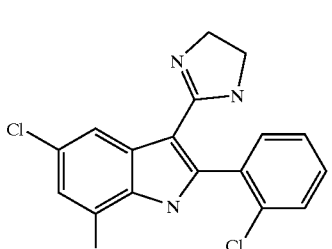 6bb | 3-(4,5-Dihydro-1H-imidazol-2-yl)-5-chloro-7-methyl-2-(2-chlorophenyl)-1H-indole Hydrochloride | 45% | 344 | 302 |

-continued

| Structure and E.g. # | Name | yield % | MS M+ | mp °C. |
|---|---|---|---|---|
| 6bc | 3-(4,5-Dihydro-1H-imidazol-2-yl)-5-chloro-2-(3-methyl-4-chlorophenyl)-1H-indole Hydrochloride | 65% | 344 | >300 |
| 6bd | 3-(4,5-Dihydro-1H-imidazol-2-yl)-5-chloro-2-(2-trifluoromethylphenyl)-1H-indole Hydrochloride | 46% | 364 | >320 |
| 6be | 3-(4,5-Dihydro-1H-imidazol-2-yl)-5-chloro-2-(2,5-dimethylphenyl)-1H-indole Hydrochloride | 54% | 324 | 160 |
| 6bf | 3-(4,5-Dihydro-1H-imidazol-2-yl)-5-methyl-2-(2,4-dichlorophenyl)-1H-indole Hydrochloride | 56% | 344 | >310 |
| 6bg | 3-(4,5-Dihydro-1H-imidazol-2-yl)-5-methyl-2-(2,5-dimethylphenyl)-1H-indole Hydrochloride | 38% | 303 | 309–312 |

-continued

| Structure and E.g. # | Name | yield % | MS M+ | mp ° C. |
|---|---|---|---|---|
| 6bh | 3-(4,5-Dihydro-1H-imidazol-2-yl)-5-chloro-2-(2,5-dichlorophenyl)-1H-indole Hydrochloride | 48% | 365 | 178–180 |
| 6bi | 3-(4,5-Dihydro-1H-imidazol-2-yl)-5,7-dichloro-2-(3-methylphenyl)-1H-indole Hydrochloride | 44% | 344 | 290–295 |
| 6bj | 3-(4,5-Dihydro-1H-imidazol-2-yl)-5,7-dichloro-2-(4-methoxyphenyl)-1H-indole Hydrochloride | 45% | 360 | >300 |
| 6bk | 3-(4,5-Dihydro-1H-imidazol-2-yl)-5,7-dichloro-2-(4-chlorophenyl)-1H-indole Hydrochloride | 43% | 365 | >300 |
| 6bl | 3-(4,5-Dihydro-1H-imidazol-2-yl)-5,7-dichloro-2-methyl-1H-indole | 45% | 268 | 264 |

3-(4,5Dihydro-1H-imidazol-2-yl)-2-methyl-5-pentafluoroethyl-1H-indole Hydrochloride
was prepared using substantially the methods described herein yielding a product which was colorless crystals, m.p. >280° C. (dec.); MS 318 (M++1).

For reasons of purification the base was transformed in a number of cases to the HCl-salt in a known manner.

EXAMPLE 7

2-(2,5-Dimethylindol-3-yl)methyl-4,5-dihydroimidazole hydrochloride (X=CH$_3$, n=1)

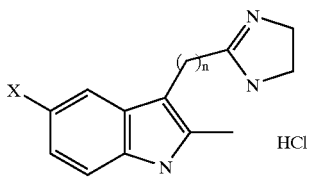

A mixture of 1.18 g (4.8 mmol) of ethyl (2,5-dimethylindol-3-yl)acetate and 7.5 mL of ethylenediamine was heated at 115° C. overnight. The excess ethylenediamine was removed under reduced pressure and the residue was chromatographed with 1:1 CH$_2$Cl$_2$-(EtOH+10% ethanolic NH$_3$). The pure fraction of N-(2-aminoethyl)-(2,5-dimethylindol-3-yl)acetamide obtained (1.2 g) was treated with 15 mL of hexamethyldisilazine HDS) at gentle reflux (130° C.) overnight. The mixture was concentrated to dryness, dissolved in EtOH and treated with etheric HCl to acidic. Addition of ether in 3 portions induced light brown crystals. Yield: 39%; m.p. 245–7° C.; $^1$H NMR (DMSO-d$_6$) d 11.02 (br. s, 1H), 9.94 (br. s, 2H), 7.23 (s, 1H ), 7.16 (d, J=8.0 Hz, 1H), 6.85 (d, J=8.0 Hz, 1H), 3.90 (s, 2H), 3.79 (s, 4H), 2.36 (s, 6H).

Except as noted, the compounds of the following Examples 7a to 7d were prepared in a manner substantially similar to that of Example 7.

EXAMPLE 7a

2-[(2-Methylindol-3-yl)methyl]-4,5-dihydroimidazole Hydrochloride (X=H, n=1)

The imidazoline was obtained in 9.3% yield, as a beige crystalline solid, m.p. 265–266° C., using POCl$_3$ instead of HMDS $^1$H NMR (DMSO-d$_6$) d 11.18 (br s, 1H), 9.60 (very br s, 2H), 7.46 (d, J=7.5 Hz, 1H), 7.28 (d, J=8 Hz, 1H), 7.03 (t, J 7.5 Hz, 1H), 6.97 (t, J=7.5 Hz, 1H), 3.94 (s, 2H), 3.78 (s, 4H), 2.39 (s, 3H); MS 213 (M$_B$+)

EXAMPLE 7b

2-[(2-Methyl-5-methoxyindol-3-yl)methyl]-4,5-dihydroimidazole Hydrochloride (X=OCH$_3$, n=1)

Yield: 11%; beige crystalline solid, m.p. 215–216° C.; $^1$H NMR (MSO-d$_6$) d 10.98 (br s, 1H), 10.00 (br s, 2H), 7.16 (d, J=7.5 Hz, 1H), 7.01 (s, 1H), 6.67 (dd, J=8.5 Hz, J=2 Hz, 1H), 3.90 (s, 2H), 3.79 (s, 3H), 3.76 (s, 4H), 2.36 (s, 3H); MS 243 (M$_B$+).

EXAMPLE 7c

2-[2-(2-Methylindol-3-yl)ethyl]-4,5-dihydroimidazole Hydrochloride (X=H, n=2)

The compound was prepared in 33% yield by heating in HS with addition of one drop of TMS chloride. m.p. 259–261° C.

$^1$H NMR (DMSO-d$_6$) d 10.87 br s, 1H), 10.26 (br s, 2H), 7.50 (d, J=7.5 Hz, 1H), 7.24 (d, J=8 Hz, 1H), 6.99 (t, J=7.5 Hz, 1H), 6.94 (t, J=7.5 Hz, 1H), 3.76 (s, 4H), 3.01 (t, J=7.5 Hz, 2H), 2.69 (t, J=7.5 Hz, 2H), 2.35 (s, 3H); MS 227 (M$_B$+).

EXAMPLE 7d

2-[2-(2-Methyl-5-methoxyindol-3-yl)ethyl]-4,5-dihydroimidazole Hydrochloride (X=OCH$_3$, n=2)

The compound was prepared by heating in HMDS with addition of one drop of TMS chloride. Yield 55%; beige crystalline solid, m.p. 274–276° C.

$^1$H NMR (DMSO-d$_6$) d 10.70 (br s, 1H), 10.36 (br s, 2H), 7.11 (d, J=8.5 Hz, 1H), 7.06 (s, 1H), 6.63 (dd, J=8.5, J=2.5 Hz, 1H), 3.77 (s, 7H), 2.99 (t, J=7.5 Hz, 2H), 2.69 (t, J=7.5 Hz, 2H) 2.32 (s, 3H); MS 257 (M$_B$+)

The following examples 8–10 were performed substantially in accordance with Example 7. As used in these examples, the variables "X" and/or "n" refer to the structure illustrated in Example 7.

EXAMPLE 8

2-(5-Fluoro-2-methylindol-3-yl)methyl4,5-dihydroimidazole hydrochloride (X=F; n=1)

Yield: 21%, m.p. 274–5° C.

EXAMPLE 9

2-(5-Chloro-2-methylindole-3-yl)methyl-4,5-dihydroimidazole hydrochloride (X=Cl; n=1)

Yield: 4.8%, m.p. 279–281° C.

EXAMPLE 10

2-(5-Bromo-2-methylindol-3-yl)methyl-4,5-dihydroimidazole hydrochloride (X=Br; n=1)

Yield: 23%, m.p. 287–9° C.

The following examples 11–15 were performed substantially in accordance with Example 7 with the exception that 1 drop of TMSCl was added to HMDS and heated at 120° C. in the imidazoline formation reaction. As used in these examples, the variables "X" and/or "n" refer to the structure illustrated in Example 7.

EXAMPLE 11

2-[2-(2,5-Dimethylindol-3-yl)ethyl]-4,5-dihydroimidazole hydrochloride (X=CH$_3$, n=2)

Yield: 46%, m.p. 292–4° C.; $^1$H NMR(DMSO-d$_6$) d 10.73 (br. s, 1H), 10.30 (br. s, 2H), 7.24 (s, 1H), 7.11 (d, J=8.0 Hz, 1H), 6.81 (d, J=8.0 Hz, 1H), 3.77 (s, 4H), 2.99 (t, J=7.5 Hz, 2H), 2.68 (t, J=7.5 Hz, 2H), 2.36 (s, 3H), 2.32 (s, 3H).

EXAMPLE 12

2-[2-(5-Fluoro-2-methylindol-3-yl)ethyl]-4,5-dihydroimidazole hydrochloride (X=F, n=2)

Yield: 48%; m.p. 323–5° C.

EXAMPLE 13

2-[2-(5-Chloro-2-methylindol-3-yl)ethyl]-4,5-dihydroimidazole hydrochloride (X=Cl, n=2)

Yield: 69%; m.p. >330° C.

EXAMPLE 14

2-[2-(5-Bromo-2-methylindol-3-yl)ethyl]-4,5-dihydroimidazole hydrochloride (X=Br, n=2)

Yield: 37%; m.p. >325° C.

EXAMPLE 15

2-[2-(5-Trifluoromethyl-2-methylindol-3-yl)ethyl]-4,5-dihydroimidazole hydrochloride (X=CF$_3$, n=2)

Yield: 9.0%; m.p. >310° C.

EXAMPLE 16

2-(7-Bromo-3-[2-methoxyethoxy]-naphthalen-2-yl)-4,5-dihydro-1H-imidazole

Ethyl-7-bromo-3-hydroxy-2-naphthoate

A solution of 81 g (0.3 mol) of 7-bromo-3-hydroxy-2-naphthoic acid in 600 ml dried EtOH and 60 ml conc. sulfuric acid was heated at reflux for 16 hours. The mixture was cooled to room temperature and treated with water (4000 ml) and neutralised with NaHCO$_3$. The solid was separated by filtration and dried in a drying chamber afforded 75.3 g (85%) of the titled compound.

Ethyl-7-bromo-3-[2-methoxyethoxy]-2-naphthoate

To a solution of 59 g (0.2 mol) of the above-mentioned compound in 400 ml dimethylformamide was added 27.6 g (0.2 mol) potassium carbonate and 34.8 g (0.25 mol) 2-methoxyethoxybromide. The mixture was heated for 6 hours at 60° C. under stirring. After cooling to room temperature, the mixture was added to water (2000 ml). The solid was separated and dried. Yield: 67.7 g (95%)

{2-Aminoethyl}-7-bromo-3-[2-methoxyethoxy]-2-naphthoamide

A mixture of 67.7 g (0.19 mol) of the above-mentioned compound and 114.2 g (0.19 mol) ethylenediamine was heated for 6 hours at 100° C. After cooling to room temperature, water (1500 ml) was added. The induced solid was separated, washed with water and dried. Yield: 59.9 g (85%).

2-(7-Bromo-3-[2-methoxyethoxy]-naphthalen-2-yl)-4,5-dihydro-1H-imidazole

To 48 g (0.13 mol) of the above-mentioned compound was added cautiously phosphorousoxy-trichloride. The mixture was heated for 4 hours at 80–90° C. After evaporation, the mixture was added to ice-water and was made basic with 5 N NaOH and extracted with dichloromethane. The extract was washed with water, dried and evaporated in vacuo and chromatographed with ethylacetate/isopropanole/methanole/ammonia 10% in ethanole 45/45/5/5 on silica gel. Yield: 30 g (66%).

EXAMPLE 17

2-(7-(4-Methyl-phenyl)-2-[2methoxyethoxy]-naphthalen-2-yl)-4,5-dihydro-1-H-imidazole To a solution of 1.4 g (4 mmol) of 2-(7-Bromo-3-[2-methoxyethoxy]-naphthalen-2-yl)-4,5-dihydro-1H-imidazole in 80 ml 1,4-dioxane was added under argon 0.46 g (0.4 mmol) of Pd(PPh$_3$)$_4$ and 8 ml of 2M Na$_2$CO$_3$. After stirring at room temperature for 20 minutes 0.816 g 4-methylbenzeneboronic acid was added and the mixture was heated for 20 hours at 80° C. The mixture was cooled to room temperature and filtered to remove the solid. The solution was acidified with 2N HCl and chromatographed on silica gel with dichloromethane/methanole 90/10 and gave 0.52 g (32%) of an amorphus product.

MS(Ei 70 eV) m/Z M+360.

$^1$H-NMR(DMSO): d 2.43 (s, 3H, CH$_3$), 3.39 (s, 3H, OCH$_3$) 3.83 (bs, 2H, CH$_2$), 4.05 (s, 4H, 2×CH$_2$), 4.36 (bs, 2H, CH$_2$), 7.56 (d, 2H, Ar—H), 7.71 (d, 2H, Ar—H), 7.73 (s, 1H, Ar—H), 7.96 (s, 1H, Ar—H), 8.20 (s, 1H, Ar—H), 8.50 (s, 1H, Ar—H), 10.18 (bs, 2H, NH.HCl).

The following examples were prepared in substantial accordance with Examples 16, 17, and the procedures and methods disclose herein. As used in the following Table, the phrase "amorph" means amorphous.

| MolStructure | Ex. # | Name | yield | mp. | MS(M$^+$) |
|---|---|---|---|---|---|
| (structure shown) | 17a | 2-[3-Methoxyethoxy)-7-(4-methylphenyl)-naphtalen-2-yl]-4,5-dihydro-1H-imidazole Hydrochloride | 33% | amorph | 360 |

-continued

| MolStructure | Ex. # | Name | yield | mp. | MS(M+) |
|---|---|---|---|---|---|
| | 17b | 2-[3-(2-Methoxyethoxy)-7-(4-methoxyphenyl)-naphthalen-2-yl]-4,5-dihydro-1H-imidazole Hydrochloride | 41% | amorph | 376 |
| | 17c | 2-[7-(4-Fluorophenyl)-3-(2-methoxyethoxy)naphthalen-2-yl]-4,5-dihydro-1H-imidazole Hydrochloride | 27% | amorph | 364 |
| | 17d | 2-[3-(2-Methoxyethoxy)-7-(3-trifluoromethylphenylnaphthalen-2-yl]-4,5-dihydro-1H-imidazole Hydrochloride | 46% | amorph | 414 |
| | 17e | 2-[3-(2-Methoxyethoxy)-7-(2-thienyl)naphthalen-2-yl]-4,5-dihydro-1H-imidazole Hydrochloride | 30.70% | amorph | 352 |

| MolStructure | Ex. # | Name | yield | mp. | MS(M⁺) |
|---|---|---|---|---|---|
| | 17f | 2-[3-(2-Methoxyethoxy)-7-(2-methoxyphenyl)-naphthalen-2-yl]4,5-dihydro-1H-imidazole Hydrochloride | 40% | amorph | 376 |
| | 17g | 2-[3-(2-Methoxyethoxy)-7-(3-thienyl)naphthalen-2-yl]4,5-dihydro-1H-imidazole Hydrochloride | 26.90% | amorph | 352 |
| | 17h | 2-[7-(3-Fluorophenyl)-3-(2-methoxyethoxy)-naphthalen-2-yl]4,5-dihydro-1H-imidazole Hydrochloride | 37% | 240–242° C. | 364 |
| | 17I | 2-[3-(2-Ethoxyethoxy)-7-(4-methylphenyl)naphthalen-2-yl]-4,5-dihydro-1H-imidazole Hydrochloride | 42% | 230–232° C. | 374 |

EXAMPLE 18

2-(4-Bromo-3-[2-methoxyethoxy]-naphthalen-2-yl)-4,5-dihydro-1H-imidazole

Ethyl-4-bromo-3-hydroxy-2-naphthoate

A solution of 41.5 g (0.156 mol) 4-bromo-3-hydroxy-naphthoic acid in 300 ml ethanol and 15 ml conc. Sulfuric acid was heated as reflux for 24 hours. The mixture was cooled to room temperature. The formed crystals were filtered off, washed with ethanol and dried. Yield: 38.05 g (83%).

Ethyl-4-bromo-3-[2-methoxyethoxy]-2-naphthoate

To a solution of 35.14 g (0.119 mol) of the above-mentioned compound in 200 ml dimethylformamide was added 16.46 g (0.119 mol) potassium carbonate and 24.9 g (0.179 g) 2-methoxyethoxybromide. The mixture was heated for 8 hours at 80° C. After cooling to room temperature, the mixture was given in water (300 ml) and extracted with ethylacetate. The extract was washed with water, dried and evaporated in vacuo giving a brown oil. Yield: 36.27 g (86.2%).

{2-Aminoethyl}-4-bromo-3-[2-methoxyethoxy]-2-naphthoamide

A mixture of 50.73 g, (0.144 mol) of the above-mentioned compound and 96 ml (0.144 mol) ethylenediamine was heated for 8 hours at 80° C. After cooling to room temperature, the mixture was evaporated in vacuo and without further purification used for the next step. Yield: 52.56 g (99.6%).

2-(4-Bromo-3-[2-methoxyethoxy]-naphthalen-2-yl)-4,5-dihydro-1H-imidazole

To 52.56 g (0.143 mol) of the above-mentioned compound was added cautiously 127 ml phosphorousoxytrichloride. The mixture was heated for 8 hours at 80° C. After evaporation, the mixture was added to ice-water, extracted with dichloromethane, dried and evaporated in vacuo. Addition of isopropanol induced hygroscopic crystals. Yield: 23.1 g (41.9%)

EXAMPLE 19

2-(4-(2,4-Dichloro-phenyl)-3-[2-methoxyethoxy]-naphthalen-2-yl)-4,5-dihydro-1H-imidazole To a solution of 25 g (0.0065 mol) of the above-mentioned compound in 100 ml 1,4-dioxan was added under argon 1.4 g (0.0012 mol) of $Pd(PPh_3)_4$ and 15 ml 2M $Na_2CO_3$. After addition of 2.47 g of 2,4-dichlorobenzeneboronic acid the mixture was heated to 18 hours at 80° C. After cooling to room temperature, the solid was filtered off, the solution was acidified with 2N HCl and after evaporation in vacuo chromatographed on silica gel with dichloromethane/ethanol 90/10 giving 860 mg (29.3%) of a crystalline product.

MS(Ei 70 eV) m/Z 414 M+, m.p. 153° C.

$^1$H-NMR(DMSO) d 3.31 (s, 3H, Ome), 3.37 (bs, 2H, $CH_2$), 3.72 (bs, 2H, $CH_2$), 4.05 (s, 4H, 2×$CH_2$), 7.25 (bs, 1H, Ar—H), 7.50 (bs, 1H, Ar—H), 7.66 (bs, 3H, Ar—H), 7.90 (s, 1H, Ar—H), 8.12 (bs, 1H, Ar—H), 8.54 (s, 1H, Ar—H).

The following examples were prepared in substantial accordance with Examples 18, 19, and the procedures and methods disclose herein.

| MolStructure | BL | Name | yield | mp | MS (M+) |
| --- | --- | --- | --- | --- | --- |
| | 19a | 2-[3-(2-Methoxyethoxy)-4-(4-methylphenyl)-naphthalen-2-yl]-4,5-dihydro-1H-imidazole | 4.16% | 147° C. | 361 |
| | 19b | 2-[4-(5-Chloro-2-thienyl)-3-(2-methoxyethoxy)-naphthalen-2-yl]-4,5-dihydro-1H-imidazole Hydrochloride | 13.60% | 180° C. | 386 |

-continued

| MolStructure | BL | Name | yield | mp | MS (M+) |
|---|---|---|---|---|---|
| | 19c | 2-[4-(2,4-Dichlorophenyl)-3-(2-methoxyethoxy)-naphthalen-2-yl]-4,5-dihydro-1H-imidazole Hydrochloride | 21.95% | 153–155° C. | 414 |
| | 19d | 2-[3-(2-Methoxyethoxy)-4-(3-thienyl)naphthalen-2-yl]-4,5-dihydro-1H-imidazole Hydrochloride | 18.50% | 209–211° C. | 352 |
| | 19e | 2-[3-(2-Methoxyethoxy-4-(4-chlorophenyl)-naphthalen-2-yl]-4,5-dihydro-1H-imidazole Hydrochlorid | 5.80% | 184–186° C. | 380 |
| | 19f | 2-[3-(2-Methoxyethoxy)-4-(3-methoxyphenyl)naphtahlen-2-yl]-4,5-dihydro-1H-imidazole Hydrochloride | 18.73% | 81° C. | 376 |
| | 19g | 2-[4-(2-Fluorophenyl)-3-(2-methoxyethoxy)naphthalen-2-yl]-4,5-dihydro-1H-imidazole Hydrochloride | 49.60% | 126° C. | 364 |

| MolStructure | BL | Name | yield | mp | MS (M+) |
|---|---|---|---|---|---|
| | 19h | 2-[3-(2-Methoxyethoxy)-4-(4-methylphenyl)naphthalen-2-yl]-4,5-dihydro-1H-imidazole Hydrochloride | 24.29% | 176–178° C. | 360 |

EXAMPLE 20

2-(2-Phenylindol-3-yl)methyl-4,5-dihydroimidazole Hydrochloride (X, Y=H, n=1)

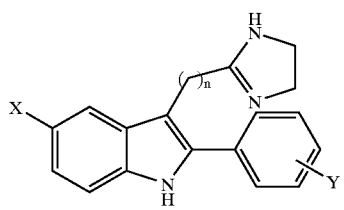

A mixture of 1.6 g (5.7 mmol) of ethyl (2-phenylindol-3-yl)acetate and 15 ml of ethylenediamine was heated at reflux overnight. The excess diamine and the formed water were removed by distillation at 90° C. in vacuo, and the crude product was chromatographed with dichloromethane/ethanol 1:1 to afford 1.35 g (80%) of N-(2-aminoethyl)-(2-phenylindol-3-yl)acetamide as a yellow crystalline solid. The amide and 20 ml of HMDS were heated at reflux under argon overnight. The crystals formed upon cooling were collected by filtration, dissolved in ethanol, and traces of HMS were stripped off along with ethanol. The title imidazoline was purified by chromatography with dichloromethane/ethanol 7:3, dissolved in ethanol and treated with ethanolic HCl to form a hydrochloride salt which was recrystallized from EtOH/EtOAc to yield 0.45 g (31%) of colorless crystals along with 0.32 g of the product salt from the mother liquid (54% overall yield).

m.p. >270° C. (dec.); $^1$H NMR (DMSO-$d_6$) d 11.67 (s, 1H), 9.94 (br s, 2H), 7.61–7.44 (m, 7H), 7.18 (t, J=7.5 Hz, 1H), 7.08 (t, J=7.5 Hz, 1H), 4.12 (s, 2H), 3.75 (s, 4H); MS 275 ($M_B^+$)

EXAMPLE 21

2-[2-(2-Chlorophenyl)indol-3-yl]methyl-4,5-dihydroimidazole Hydrochloride (X=H, Y=2-Cl, n=1)

A mixture of 0.75 g (2.4 mmol) of ethyl (2-(2-chlorophenyl)indol-3-yl)acetate and 5 ml of ethylenediamine was heated at 120+ C. for 4 h. The excess amine and the formed water were removed by distillation in vacuo. The crude amide was purified by chromatography with isopropanol/ethyl acetate/125% NH$_4$OH 4:5:0.1 to yield 400 mg (51%) as a yellow oil. The amide, 5 ml of HMDS, and 1 drop of TMS chloride were heated at reflux under argon overnight. The crude precipitate formed upon cooling was filtered, washed with ethanol, and chromatographed using the same eluent used in Example 20, above. The hydrochloride salt was formed by treatment with ethanolic HCl and recrystallized from acetone to afford 40 mg (9.5%) of beige crystals of the title compound.

m.p. >157° C. (dec.); $^1$H NMR (DMSO-$d_6$) d 11.61 (s, 1H), 9.82 (br s, 2H), 7.66 (d, J=7.5 Hz, 1H), 7.54 (m, 4H), 7.43 (d, J=8 Hz, 1H), 7.20 (t, J=7.5 Hz, 1H), 7.11 (t, J=7.5 Hz, 1H), 3.88 (s, 2H), 3.68 (s, 4H); MS 309 ($M_B^+$).

The following compounds were prepared, except as noted, essentially in the same manner as described for Examples 20 and 21:

EXAMPLE 22

2-[2-(2-Trifluoromethylphenyl)indol-3-yl]methyl-4,5-dihydroimidazole Hydrochloride (X=H, Y=2-CF$_3$, n=1)

without chromatographic purification of the 2-aminoethylamide; yield: 64%; beige crystals, m.p. 180–4° C.;

$^1$H NMR (DMSO-$d_6$) d 11.61 (s, 1H), 9.84 (br s, 2H), 7.83 (d, J=7.5 Hz, 1H), 7.82 (d, J=7.5 Hz, 1H), 7.77 (d, J=7.5 Hz, 1H), 7.71 (d, J=7.5 Hz, 1H), 7.55 (d, J=7.5 Hz, 1H), 7.41 (d, J=8 Hz, 1H), 7.20 (t, J=7.5 Hz, 1H), 7.11 (t, J=7.5 Hz, 1H), 3.71 (s, 6H); MS 343 ($M_B^+$).

EXAMPLE 23

2-[2-(2,4-Dichlorophenyl)indol-3-yl]methyl-4,5-dihydroimidazole Hydrochloride (X=H, Y=2, 4-Cl$_2$, n=1)

2-aminoethylamide: 31% yield, yellow oil imidazoline: 43% yield; beige crystals, m.p. 243–5° C.; MS 343 ($M_B^+$).

EXAMPLE 24

2-[2-(2-Chlorophenyl)-5-fluoroindol-3-yl]methyl-4,5-dihydroimidazole Hydrochloride (X=F, Y=2-Cl, n=1)

without chromatographic purification of the 2-aminoethylamide; yield: 4.8%; beige crystals, m.p. 191–3° C.; MS 327 ($M_B^+$).

EXAMPLE 25

2-[5-Chloro-2-(2-chlorophenyl)indol-3-yl]methyl-4,
5-dihydroimidazole Hydrochloride
(X=Cl, Y=2-Cl, n=1)

2-aminoethylamide: 60% yield, yellow oil which solidified upon standing imidazoline: 53% yield; beige crystals, m.p. 195–7° C.; MS 343 ($M_B^+$).

EXAMPLE 26

2-[2-(2-Phenylindol-3-yl)ethyl]-4,5-
dihydroimidazole Hydrochloride (X, Y=H, n=2)
without chromatographic purification of the 2-aminoethylamide; yield: 21%; beige crystals, m.p. 239–41° C.;

$^1$H NMR (DMSO-$d_6$) d 11.37 (s, 1H), 10.22 (br s, 2H), 7.72 (d, J=8 Hz, 1H), 7.66 (d, J=7.5 Hz, 2H), 7.54 (t, J=7.5 Hz, 2H), 7.42 (d, J=7.5 Hz, 1H), 7.39 (d, J=8 Hz, 1H), 7.14 (t, J=7.5 Hz, 1H), 7.05 (t, J=7 Hz, 1H), 3.71 (s, 4H), 3.23 (t, J=8 Hz, 2H), 2.79 (t, J=8 Hz, 2H); MS 289 ($M_B^+$).

EXAMPLE 27

2-[2-(2-(2-Fluorophenyl)indol-3-yl)ethyl]-4,5-
dihydroimidazole Hydrochloride
(X=H, Y=2-F, n=2)

The 2-aminoethylamide was obtained as a yellow oil in 69% yield and converted to the imidazoline by heating in HMDS without addition of TMS chloride. The title imidazoline was recrystallized from isopropanol after chromatographic purification with dichloromethane/ethanol 7:3 and obtained in 39% yield of pure hydrochloride salt along with 52% of the crude salt from the mother liquid.

beige crystals, m.p. >135° C. (dec.); $^1$H NMR (DMSO-$d_6$) d 11.36 (s, 1H), 10.17 (s, 2H), 7.73 (d, J=7.5 Hz, 1H), 7.59 (t, J=7 Hz, 1H), 7.52 (d, J=5.5 Hz, 1H), 7.39 (m, 3H), 7.16 (t, J=7 Hz, 1H), 7.07 (t, J=7 Hz, 1H), 3.69 (s, 4H), 3.07 (t, J=7 Hz, 2H), 2.74 (t, J=7 Hz, 2H); MS 307 ($M_B^+$).

EXAMPLE 28

2-[-2-(2-(2-Chlorophenyl)indol-3-yl)ethyl]-4,5-
dihydroimidazole Hydrochloride (X=H, Y=2-Cl, n=2)

The 2-aminoethylamide was obtained as a pale yellow foam in 83% yield. The imidazoline was formed from the amide by heating in HMDS with addition of two drops of TMS chloride, purified by chromatography with dichloromethane/ethanol 3:2, and recrystallized from isopropanol to give the pure hydrochloride salt in 30% along with 43% yield of the crude salt from the mother liquid.

yellow crystalline solid, m.p. >173° C. (dec.); 1H NMR (DMSO-$d_6$) d 11.29 (s, 1H), 9.89 (s, 2H), 7.70 (d, J=8 Hz, 1H), 7.65 (d, J=7 Hz, 1H), 7.54–7.50 (m, 3H), 7.36 (d, J=8 Hz, 1H), 7.14 (t, J=7.5 Hz, 1H), 7.07 (t, J=7.5 Hz, 1H), 3.66 (s, 4H), 3.00 (t, J=7.5 Hz, 2H), 2.72 (t, J=7.5 Hz, 2H); MS 323 ($M_B^+$).

EXAMPLE 29

2-[-2-(2-Trifluoromethylphenyl)indol-3-yl)ethyl]-4,
5-dihydroimidazole Hydrochloride
(X=H, Y=2-CF$_3$, n=2)

2-aminoethylamide: 45% yield, yellow oil imidazoline: 48% yield; pale yellow crystals after crystallization from acetone, m.p. 288–91° C.;

$^1$HNMR(DMSO-$d_6$) d 11.26 (s, 1H), 10.16 (s, 2H), 7.92 (d, J=8 Hz, 1H), 7.80 (d, J=7 Hz, 1H), 7.74 (t, J=7.5 Hz, 1H), 7.71 (t, J=8 Hz, 1H), 7.60 (d, J=7.5 Hz, 1H), 7.35 (d, J=8 Hz, 1H), 7.15 (t, J=7.5 Hz, 1H ), 7.07 (t, J=7.5 Hz, 1H), 4.03 (br s, 4H), 2.87 (t, J=7 Hz, 2H), 2.66 (distort. t, J=7 Hz, 2H); MS 357 ($M_B^+$).

EXAMPLE 30

2-[2-(2-(2,4-Dichlorophenyl)indol-3-yl)ethyl]-4,5-
dihydroimidazole Hydrochloride
(X=H, Y=2,4-C$_{12}$, n=2)

2-aminoethylamide: 98% yield, pale yellow crystalline solid after stirring with ethanol imidazoline: 26% yield; beige crystals after crystallization from acetone, m.p. 247–9° C.; MS 357 ($M_B^+$)

EXAMPLE 31

2-(3-Chlorobenzo[b]thiophen-2-yl)-4,5-dihydro-1H-
imidazole (X=Cl, Y=H)

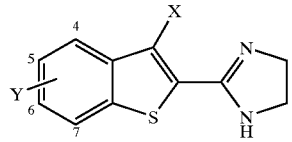

Step A: 2-(2-Phenylethen-1yl)-4,5-dihydro-1H-
imidazole

A solution of 5.3 g (50 mmol) of benzaldehyde and 4.2 g (50 mmol) of 2-methyl-4,5-dihydro-1H imidazole in 50 ml toluene was refluxed in a Dean-Stark apparatus. Within 8 h 0.9 ml of water had been separated and the reaction was almost complete as detected by TLC. After cooling the crystalline precipitate was filtered off, treated with cold tert.-butylmethylether, and dried in vacuo.

yield: 2.6 g (23%)

Step B: 2-(3-Chlorobenzo[b]thiophen-2-yl)-4,5-
dihydro-1H-imidazole 0.34 g (2 mmol) of the imidazoline described in the previous step was mixed with 0.17 ml of thionyl chloride and 20 µl pyridine under argon. After heating to 140° C. another 0.34 ml of thionyl chloride was slowly added and heating was continued for another 2 h. It was cooled and an an excess of ethanol was carefully added. All volatiles were removed in vacuo, and the title compound was obtained from the residue via column chromatography on silica gel with dichloromethane/ethanolic ammonia gradient.

yield: 0.1 g (21%); brown crystalline solid.

EXAMPLE 32

2-(Benzo[b]thiophen-2-yl)-4,5-dihydro-1H-
imidazole (X=Y=H)

The title compound was prepared in the essentially the same manner, from 0.34 g (2 mmol) of 2-(2-phenylethen-1-yl)-4,5-dihydro-1H-imidazole and thionyl bromide, as described in Example 31.

yield: 40 mg (9.5%); brown amorphous solid

EXAMPLE 33

2-(3-Phenylbenzo[b]thiophen-2-yl)-4,5-dihydro-1H-
imidazole (X=phenyl, Y=H)

A solution of 70 mg (0.3 mmol) of 2-(3-chlorobenzotblthiophen-2-yl)-4,5-dihydro-1H-imidazole, 61 mg (0.5 mmol) of benzeneboronic acid, and 35 mg (0.03 mmol) of tetrakis(triphenylphosphine)palladium(0) in a mixture of 5 ml dioxane and 1 ml 2M aqueous sodium carbonate solution was heated at 95° C. for 5 d. It was cooled and evaporated to dryness. The title compound was obtained from the residue after repeated column chromatography on silica gel with dichloromethane/ethanolic ammonia gradient.

yield: 10 mg (12%); brown resin

EXAMPLE 34

2-(3-(4-Methylthiophenyl)benzo[b]thiophen-2-yl)-4,5-dihydro-1H-imidazole (X=4-methylthiophenyl, Y=H)

The title compound was prepared by a Suzuki coupling reaction between 4-methylthiobenzeneboronic acid and 2-(3-chlorobenzo[b]thiophen-2-yl)-4,5-dihydro-1H-imidazole as described in Example 33.

EXAMPLE 35

2-(3-Butoxybenzo[b]thiophen-2-yl)-4,5-dihydro-1H-imidazole (X=OC$_4$H$_9$, Y=H)

A solution of 0.1 g (0.42 mmol) of 2-(3-chlorobenzo[b]thiophen-2-yl)-4,5-dihydro-1H-imidazole and 56 mg (0.5 mmol) of potassium tert.-butoxide in 2 ml of absolute n-butanol was heated for 3 d. After cooling the mixture was filtered, the filter rinsed with dichloromethane, and the filtrate concentrated under reduced pressure. The title compound was obtained from the residue after column chromatography on silica gel with dichloromethane/ethanolic ammonia gradient.

yield: 10 mg (8.7%); brown resin

EXAMPLE 36

2-(6-Bromo-3-chlorobenzo[b]thiophen-2-yl)-4,5-dihydro-1H-imidazole (X=Cl, Y=6-Br)

Step A: Ethyl 6-Bromo-3-chlorobenzo[b]thiophen-2-carboxylate 3.4 g (15 mmol) of 4-bromocinnamic acid were mixed with 4 g (33 mmol) of thionyl chloride and 150 μl pyridine under argon. The mixture was stirred at 145° C. followed by slow addition of another 8 g (66 mmol) of thionyl chloride. After 6 h it was cooled and 20 ml of absolute ethanol was added carefully. All volatiles were removed in vacuo, and the title compound was isolated from the residue via column chromatography on silica gel with dichloromethane/ethanolic ammonia gradient.

yield: 4.1 g (85%).

Step B: 2-(6-Bromo-3-chlorobenzo[b]thiophen-2-yl)-4,5-dihydro-1H-imidazole

A mixture of 4 g (12.5 mmol) ethyl 6-bromo-3-chlorobenzo[b]thiophen-2-carboxylate and 7.5 g (125 mmol) ethylendiamine were heated at 80° C. overnight. It was concentrated in vacuo, and the crude 2-ethylaminoamide was dissolved in 70 ml dry dichloromethane followed by addition of 10.5 ml triethylamine and 15 g (75 mmol) TMS iodide. After five days stirring at room temperature the reaction was almost complete as detected by TLC. It was extracted with water, dried over sodium sulfate, and concentrated under reduced pressure. The title imidazoline was isolated from the residue by column chromatography on silica gel with dichloromethane/ethanolic ammonia gradient.

yield: 2.46 g (62%); beige crystalline powder.

The following examples were prepared essentially in the same manner starting from the corresponding cinnamic acids:

EXAMPLE 37

2-(7-Bromo-3-chloro-4-methoxybenzo[b]thiophen-2-yl)-4,5-dihydro-1H-imidazole
(X=Cl, Y=7-Br-4-OCH$_3$)

brown crystalline solid.

EXAMPLE 38

2-(3,4-Dichlorobenzo[b]thiophen-2-yl)-4,5-dihydro-1H-imidazole Hydroiodide (X=Cl, Y=4-Cl)

pale yellow crystals.

EXAMPLE 39

2-(3-Chloro-4-methoxybenzo[b]thiophen-2-yl)-4,5-dihydro-1H-imidazole Hydroiodide
(X=Cl, Y=4-OCH$_3$)

grey powder.

EXAMPLE 40

2-(3-Chloro-4-trifluoromethylbenzo[b]thiophen-2-yl)-4,5-dihydro-1H-imidazole Hydroiodide
(X=Cl, Y=4-CF$_3$)

colorless crystals.

EXAMPLE 41

2-(3-Chloro-6-trifluoromethylbenzo[b]thiophen-2-yl)-4,5-dihydro-1H-imidazole Hydroiodide
(X=Cl, Y=6-CF$_3$)

beige crystalline solid.

EXAMPLE 42

2-(3-Chloro-6-methylbenzo[b]thiophen-2-yl)-4,5-dihydro-1H-imidazole Hydroiodide
(X=Cl, Y=6-CH$_3$)

grey crystalline solid.

EXAMPLE 43

2-(4-Bromo-3-chlorobenzo[b]thiophen-2-yl)-4,5-dihydro-1H-imidazole Hydroiodide (X=Cl, Y=4-Br)

colorless crystals.

EXAMPLE 44

2-(7-Bromo-3-chlorobenzo[b]thiophen-2-yl)-4,5-dihydro-1H-imidazole Hydroiodide (X=Cl, Y=7-Br)

beige crystalline solid.

EXAMPLE 45

2-(3-Chloro-6-(naphthalen-1-yl)benzo[b]thiophen-2-yl)-4,5-dihydro-1H-imidazole (X=Cl, Y=6-(naphthalen-1-yl))

A solution of 60 mg (0.19 mmol) of 2-(6-bromo-3-chlorobenzo[b]thiophen-2-yl)-4,5dihydro-1H-imidazole, 69 mg (0.4 mmol) of naphthalene-1-boronic acid, and 23 mg (0.02 mmol) of Pd(PPh$_3$)$_4$ in a mixture of 2.5 ml dioxane and 0.4 ml 2M aqueous sodium carbonate solution was heated at 95° C. for 24 h. After cooling it was concentrated to dryness under reduced pressure, and the title compound was obtained from the residue by column chromatography on silica gel with dichloromethane/ethanolic ammonia gradient.

yield: 20 mg (29%); brown amorphous solid

EXAMPLE 46

2-(3-Chloro-6-(2-thienyl)benzo[b]thiophen-2-yl)-4,5-dihydro-1H-imidazole (X=Cl, Y=6-(2-thienyl))

The compound was prepared in manner similar to that of Example 45 from 2-(6-bromo-3-chlorobenzo[b]thiophen-2-yl)-4,5-dihydro-1H-imidazole and thiophen-2-boronic acid.

EXAMPLE 47

(2-(4,5-Dihydro-1H-imidazol-2-yl)benzo[b]thiophen-3-yl)-(4-methoxyphenyl)methanol (R=4-methoxyphenyl)

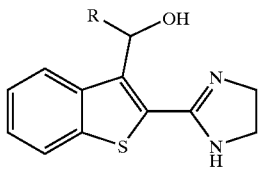

A stirred solution of 120 mg (0.5 mmol) of 2-(3-chlorobenzo[b]thiophen-2-yl)-4,5-dihydro-1H-imidazole in 5 ml of absolute THF was cooled to −78° C. and 0.625 ml of a 1.6 M solution of butyllithium in hexane (1 mmol) was added dropwise. After stirring for 1 h at −40° C. another 0.15 ml of 1.6 M butyllithium in hexane was added and stirring at −40° C. was continued for 15 min. It was added dropwise via a syringe a solution of 152 µl (1.25 mmol) of 4-methoxybenzaldehyde in 1 ml of absolute THF, and the mixture was slowly warmed to room temperature overnight After careful quenching with water it was extracted with ether. The combined organic layers were dried over sodium sulfate and evaporated in vacuo, and the residue was purified via column chromatography on silica gel with dichloromethane/ethanolic ammonia gradient.

yield: 50 mg (30%); beige crystalline solid.

The following Examples 48–54 were prepared in a similar manner to that of Example 47 by lithiation of 2-(3-chlorobenzo[b]thiophen-2-yl)-4,5-dihydro-1H-imidazole employing the following modification of the above described procedure:

A stirred solution of 100 mg (0.42 mmol) of 2-(3-chlorobenzo[b]thiophen-2-yl)-4,5-dihydro-1H-imidazole in 4 ml of absolute THF was cooled to −50° C. and 0.563 ml of 1.6 M butyllithium in hexane (0.9 mmol) was added dropwise. It was warmed to 0° C. within 4 h under stirring followed by dropwise addition via a syringe of a solution of 1 mmol of the aldehyde in 1 ml of dry THF. The mixture was slowly warmed to room temperature, and after stirring for 2 d the mixture was carefully quenched with 0.5 ml of ethanol followed by addition of 2 g of Amberlyst 15. The slurry was stirred for 20 min, and the the ion exchange resin was removed by filtration and rinsed with ethanol, dichloromethane/ethanolic ammonia 95:5, dichloromethane/ethanolic ammonia 1:1, and ethanolic ammonia (each 3×4 ml), successively. The fractions were checked by TLC, and those containing the title imidazoline were combined and concentrated under reduced pressure. The residue was purified via column chromatography on silica gel with dichloromethane/ethanolic ammonia gradient.

EXAMPLE 48

(2-(4,5-Dihydro-1H-imidazol-2-yl)benzo[b]thiophen-3-yl)-(3,4-methylendioxyphenyl)methanol (R=3,4-methylendioxyphenyl)

brown amorphous solid.

EXAMPLE 49

(2-(4,5-Dihydro-1H-imidazol-2-yl)benzo[b]thiophen-3-yl)-(pyridin-3-yl)methanol (R=pyridin-3-yl)

brown resin.

EXAMPLE 50

(2-(4,5-Dihydro-1H-imidazol-2-yl)benzo[b]thiophen-3-yl)-(2-thienyl)methanol (R=2-thienyl)

brown resin.

EXAMPLE 51

(2-(4,5-Dihydro-1H-imidazol-2-yl)benzo[b]thiophen-3-yl)-(2-fluorophenyl)methanol (R=2-fluorophenyl)

beige amorphous solid.

EXAMPLE 52

(2-(4,5-Dihydro-1H-imidazol-2-yl)benzo[b]thiophen-3-yl)-(naphthalen-1-yl)methanol (R=1-naphthyl)

beige amorphous solid.

EXAMPLE 53

(4-tert.-Butylphenyl)-(2-(4,5-dihydro-1H-imidazol-2-yl)benzo[b]thiophen-3-yl)methanol (R=4-tert.-butylphenyl)

brown amorphous solid.

EXAMPLE 54

2,4-Dichlorophenyl)-(2-(4,5-dihydro-1H-imidazol-2-yl)benzo[b]thiophen-3-yl)methanol (R=2,4-dichlorophenyl)

brown amorphous solid.

EXAMPLE 55

5-Chloro-3-(4,5-dihydro-1H-imidazol-2-yl)-2-(3-fluorophenyl)-1H-indole (X=3-F)

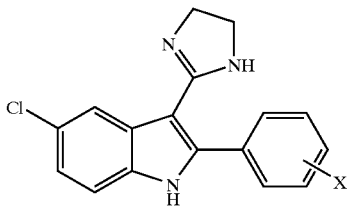

Ethylendiamine tosylate (929 mg, 4.0 mmol) and 5-chloro-3-cyano-2-(3-fluorophenyl)-1H-indole (0.27 g, 1.0 mmol) were thoroughly mixed in a mortar and heated with melting at 320° C. for 10 min. After cooling it was stirred with a small amount of water, and the mixture was brought to pH9 with 2N sodium hydroxide. The precipitate was collected by filtration, washed with water, and dried in vacuo. The title imidazoline was isolated by chromatography on silica gel with dichloromethane/10% ethanolic ammonia 9:1 and recrystallized from methanol.

yield: 40 mg (13%); beige crystalline solid, m.p. 248–250 IC; MS 312 ($M^+$−1).

The following Examples 56–58 were prepared in essentially thes ame manner as described in Example 55:

EXAMPLE 56

5-Chloro-3-(4,5-dihydro-1H-imidazol-2-yl)-2-(3-trifluoromethylphenyl)-1H-indole (X=3-$CF_3$)

yield: 28%; beige crystalline solid, m.p. 258–260° C.; MS 362 ($M^+$−1).

EXAMPLE 57

5-Chloro-3-(4,5-dihydro-1H-imidazol-2-yl)-2-(3-iodophenyl)-1H-indole (X=3-I)

yield: 13%; beige crystalline solid after chromatography and recrystallization from ethyl acetate,
m.p. 242–244° C.; MS 422 ($M^+$+1).

EXAMPLE 58

5-Chloro-3-(4,5-dihydro-1H-imidazol-2-yl)-2-(4-iodophenyl)-1H-indole (X=4-I)

yield: 29%; colorless crystals after chromatography and recrystallization from ethanol, m.p. 246–248° C.; MS 422 ($M^+$+1).

EXAMPLE 59

5-Chloro-3-(4,5-dihydro-1H-imidazol-2-yl)-1H-indole

Step A: 5-Chloro-1H-indole-3-carboxylic Acid

A solution of 5.0 g (33.0 mmol) of commercially available 5-chloro-1H-indole in 50 ml dry DMF was kept at 0° C., while 7.35 g (35.0 mmol) trifluoroacetanhydride was added dropwise. After 3 h stirring at room temperature the mixture was poured into 200 ml water, and the precipitate was filtered with suction and heated with reflux overnight in 200 ml 20% NaOH. It was extracted twice with dichloromethane, and the aqueous layer was acidified with hydrochloric acid. The crystalline title compound was collected by filtration and dried in vacuo.

yield: 6.0 g (93%)

Step B: Ethyl 5-Chloro-1H-indole-3-carboxylate

To a suspension of 5.23 g (26.74 mmol) 5-chloro-1H-indole-3-carboxylic acid in 140 ml dry ethanol were added 10 ml concentrated sulfuric acid, and the mixture was heated with reflux for 16 h. It was concentrated under reduced pressure, and the residue was tretaed with ethanol/hexane to give the crystalline title ester, which was filtered and dried in vacuo.

yield: 3.84 g (64%); MS 224 ($M^+$+1)

The ethyl ester may also be prepared according to procedures known in the art (Japanese Patent 62 153271 (CA 108 (1988), 150791)) from ethyl acrylate and 2-bromo-5-chloroaniline in two Pd catalyzed steps in 9% overall yield.

Step C: 5-Chloro-3-(4,5-dihydro-1H-imidazol-2-yl)-1H-indole

A mixture of 1.34 g (6.0 mmol) ethyl 5-chloro-1H-indole-3-carboxylate and 10 ml ethylenediamine were heated at 120° C. for 4 days. The excess of diamine was removed in vacuo, and the residue was stirred with a small amount of ether to give the pale yellow crystalline 2-aminoethylamide.

yield: 0.77 g (54%); MS 238 ($M^+$+1) The crude amide was heated at 120° C. overnight with 7.5 ml HMDS containing several drops of TMS iodide. The mixture was concentrated to dryness under reduced pressure, and the title imidazoline was obtained by chromatography on silica gel with dichloromethane/ethanol 1:1.

yield: 0.32 g (45%); beige crystalline solid; m.p. >300° C.; MS 220 ($M^+$+1).

EXAMPLE 60

2-[5-Chloro-2-(4-methoxyphenyl)benzofuran-3-yl]-4,5-dihydro-1H-imidazole (X=Cl, R=H, Y=4-methoxyphenyl)

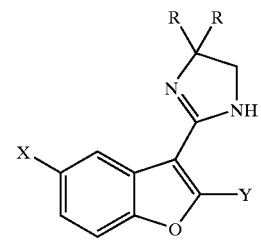

A mixture of 0.41 g (1.13 mmol) ethyl 5-chloro-2-(4-methoxyphenyl)benzofuran-3-dithiocarboxylate, 0.4 g (6.65 mmol) ethylenediamine, and one drop of $CS_2$ in 20 ml ethanol was heated at reflux for 4 h. The solvent was removed in vacuo, and the residue was treated with water and brought to pH5 with 2N hydrochloric acid. Solids were removed by filtration, and the filtrate was brought to pH10 with 30% aqueous sodium hydroxide and extracted with ethyl acetate. The organic layer was dried over sodium sulfate and concentrated under reduced pressure, and the title imidazoline was obtained after chromatography on silica gel with dichloromethane/10% ethanolic ammonia 98:2.

yield: 60 mg (16%); pale yellow crystals, m.p. 175–177° C.; MS 366 ($M^+$+1)

The following benzofurans, Examples 61–68, were prepared, except as noted, in the same manner as described in Example 60, with 1,2-diaminoethane or 1,2-diamino-2-methylpropane from the corresponding dithiocarboxylates:

EXAMPLE 61

2-[5-Chloro-2-(2-chlorophenyl)benzofuran-3-yl]-4,5-dihydro-1H-imidazole Hydrochloride (X=Cl, R=H, Y=2-chlorophenyl)

The imidazoline was isolated by extraction of the aqueous mixture with ethyl acetate. The hydrochloride salt was prepared from the residue with a mixture of ether and ethanol containing HCl and recrystallized from ethanol.

yield: 44%; colorless crystalline solid, m.p. 275–277° C.

EXAMPLE 62

2-[5-Chloro-2-(3-chlorophenyl)benzofuran-3-yl]-4,5-dihydro-1H-imidazole (X=Cl, R=H, Y=3-chlorophenyl)

yield: 22%; pale yellow crystalline solid, m.p. 181–83° C.; MS 331 ($M^+$+1)

EXAMPLE 63

2-[5-Chloro-2-(4-chlorophenyl)benzofuran-3-yl]-4,5-dihydro-1H-imidazole (X=Cl, R=H, Y=4chlorophenyl)

yield: 23%; colorless crystals, m.p. 215–217° C.; MS 331 ($M^+$+1).

EXAMPLE 64

2-[5-Chloro-2-(3-methylphenyl)benzofuran-3-yl]-4,5-dihydro-1H-imidazole (X=Cl, R=H, Y=3-methylphenyl)

yield: 14%; colorless crystals, m.p. 169–171° C.; MS 311 ($M^+$+1).

EXAMPLE 65

2-(5-Chloro-2-methylbenzofuran-3-yl)-4,5-dihydro-1H-imidazole (X=Cl, R=H, Y=$CH_3$)

yield: 33%; pale yellow crystalline solid, m.p. 187–190° C.; MS 234 ($M^+$).

EXAMPLE 66

2-(5-Fluoro-2-methylbenzofuran-3-yl)-4,5-dihydro-1H-imidazole (X=F, R=H, Y=$CH_3$)

After chromatography the compound was recrystallized from toluene/hexane for further purification.

yield: 25%; colorless crystals, m.p. 159–162° C.; MS 218 ($M^+$).

EXAMPLE 67

2-(5-Chloro-2-methylbenzofuran-3-yl)-4,5-dihydro-4,4-dimethyl-1H-imidazole (X=Cl, R=Y=$CH_3$)

yield: 6%; pale yellow crystals, m.p. 140–142° C.; MS 262 ($M^+$).

EXAMPLE 68

2-(5-Fluoro-2-methylbenzofuran-3-yl)-4,5-dihydro-4,4-dimethyl-1-imidazole (X=F, R=Y=$CH_3$)

The compound was obtained as a resinous oil after chromatography and crystallized from cyclohexane.

yield: 25%; beige crystalline solid, m.p. 117–120° C.; MS 246 ($M^+$).

EXAMPLE 69

2-(5-Chloro-2-methylbenzo[b]thiophen-3-yl)-4,5-dihydro-1H-imidazole (X=Cl, R=H, Y=$CH_3$)

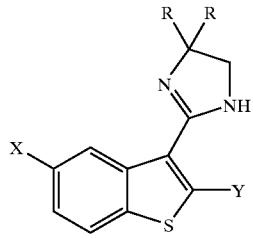

A mixture of 0.7 g (2.44 mmol) ethyl 5-chloro-2-methylbenzo[b]thiophen-3-dithiocarboxylate and 10 ml ethylenediamine was heated for 2 h at 120° C. It was poured into 150 ml water, stirred for 10 min and extracted with ethyl acetate. The organic layer was dried over sodium sulfate and concentrated under reduced pressure to leave the title compound which was purified by crystallization from acetonitrile.

yield: 0.51 g (83%); colorless crystals, m.p. 190–192° C.; MS 250 ($M^+$).

The following benzo[b]thiophenes, Examples 70–81, were prepared, except as noted, in essentially the same manner as described in Example 69, with 1,2-diaminoethane or 1,2-diamino-2-methylpropane from the corresponding dithiocarboxylates:

EXAMPLE 70

2-(5-Fluoro-2-methylbenzo[b]thiophen-3-yl)-4,5-dihydro-1H-imidazole (X=F, R=H, Y=$CH_3$)

yield: 50%; colorless crystalline solid, m.p. 161–163° C.; MS 234 ($M^+$).

EXAMPLE 71

2-[5-Chloro-2-(2-chlorophenyl)benzo[b]thiophen-3-yl]-4,5-dihydro-1H-imidazole (X=Cl, R=H, Y=2-chlorophenyl)

The compound was purified by chromatography with dichloromethane/10% ethanolic ammonia 98:2.

yield: 37%; pale yellow crystalline solid, m.p. 122–125° C.; MS 345 ($M^+$–1), 311 ($M^+$–Cl).

EXAMPLE 72

2-[2-(2-Chlorophenyl)-5-fluorobenzo[b]thiophen-3-yl]-4,5-dihydro-1H-imidazole (X=F, R=H, Y=2-chlorophenyl)

The compound was purified by chromatography with dichloromethane/10% ethanolic ammonia 98:2.

yield: 44%; pale yellow crystals, m.p. 177–179° C.; MS 329 ($M^+$–1), 295 ($M^+$–Cl).

EXAMPLE 73

2-[5-Chloro-2-(4-methylphenyl)benzo[b]thiophen-3-yl]-4,5-dihydro-1H-imidazole (X=Cl, R=H, Y=4-methylphenyl)

The imidazoline was purified by chromatography with toluene/ethanol 3:2.

yield: 56%; colorless crystalline solid, m.p. 217–220° C.; MS 325 (M$^+$–1).

EXAMPLE 74

2-[5-Fluoro-2-(4-methylphenyl)benzo[b]thiophen-3-yl]-4,5-dihydro-1H-imidazole (X=F, R=H, Y=4-methylphenyl)

yield: 45%; pale yellow crystals, m.p. 187–189° C.; MS 309 (M$^+$–1).

EXAMPLE 75

2-(5-Chloro-2-heptylbenzo[b]thiophen-3-yl)-4,5-dihydro-1H-imidazole (X=Cl, R=H, Y=n-C$_7$H$_{15}$)

The title compound was purified by chromatography with dichloromethane/10% ethanolic ammonia 95:5.

yield: 71%; colorless crystalline solid, m.p. 126–128° C.; MS 334 (M$^+$).

EXAMPLE 76

2-(5-Chloro-2-methylbenzo[b]thiophen-3-yl)-4,5-dihydro-4,4-dimethyl-1H-imidazole (X=Cl, R=Y=CH$_3$)

The title imidazoline was purified by chromatography with dichloromethane/10% ethanolic ammonia 97:3 followed by crystallization from acetonitrile.

yield: 47%; colorless crystalline powder, m.p. 158–160° C.; MS 278 (M$^+$).

EXAMPLE 77

2-(5-Fluoro-2-methylbenzo[b]thiophen-3-yl)-4,5-dihydro-4,4-dimethyl-1H-imidazole (X=F, R=Y=CH$_3$)

It was purified by chromatography with dichloromethane/10% ethanolic ammonia 97:3, and the title compound crystallized by stirring with acetonitrile.

yield: 61%; pale yellow foam, m.p. 112–115° C.; MS 262 (M$^+$).

EXAMPLE 78

2-[5-Chloro-2-(4-methylphenyl)benzo[b]thiophen-3-yl]-4,5-dihydro-4,4-dimethyl-1H-imidazole (X=Cl, R=CH$_3$, Y=4-methylphenyl)

The imidazoline was purified by chromatography with toluene/ethanol 7:3.

yield: 50%; colorless oil which slowly crystallized, m.p. 128–130° C.; MS 353 (M$^+$–1).

EXAMPLE 79

2-[5-Fluoro-2-(4-methylphenyl)benzo[b]thiophen-3-yl]-4,5-dihydro-4,4-dimethyl-1H-imidazole (X=F, R=CH$_3$, Y=4-methylphenyl)

The imidazoline was purified by chromatography with toluene ethanol 4:1.

yield: 61%; colorless crystalline solid, m.p. 213–215° C.; MS 337 (M$^+$–1).

EXAMPLE 80

2-(5-Chloro-2-heptylbenzo[b]thiophen-3-yl)-4,5-dihydro-4,4-dimethyl-1H-imidazole (X=Cl, R=CH$_3$, Y=n-C$_7$H$_{15}$)

The title imidazoline was purified by chromatography with dichloromethane/10% ethanolic ammonia 95:5.

yield: 59%; beige foam; MS 362 (M$^+$).

EXAMPLE 81

2-(5-Chloro-2-methylbenzo[b]thiophen-3-yl)-4,5-dihydro-1H-oxazole

The oxazoline was prepared by heating of 0.3 g (1.05 mmol) ethyl 5-chloro-2-methylbenzo[b]thiophene-3-dithiocarboxylate in 2 ml 2-aminoethanol as described above, and it was isolated by chromatography on silica gel with hexane/ethyl acetate 9:1.

yield: 60 mg (23%); colorless crystalline solid, m.p. 100–102° C.; MS 251 (M$^+$).

EXAMPLE 82

3-(4,5-Dihydro-1H-imidazol-2-yl)-2-mercaptoquinoline-2-thiol

A mixture of 1.81 g (10 mmol) of 2-chloroquinoline-3-carbaldehyde, 320 mg of elemental sulfur, and 2.4 g (400 mmol) of ethylenediamine in 20 ml isobutanol was heated to 115° C. for 6 h. After cooling the mixture was filtered and evaporated. The residue was purified via column chromatography (dichloromethane/ethanol 10:3).

yield: 570 mg (25%); brown crystals, m.p. 61–63° C.

EXAMPLE 83

5-Chloro-3-(4,5-dihydro-1H-imidazol-2-yl)-2-(pyridin-3-yl)-1H-indole (X=Cl, R=3-pyridyl)

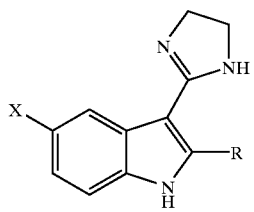

Step A: Ethyl (E/Z)-2-(5-Chloro-2-nitrophenyl)-3-(pyridin-3-yl)propenoate

To a solution of 700 mg (3 mmol) of ethyl 5-chloro-2-nitrophenylacetate (prepared according to Synthesis 1988, 1007), 321 mg (281 µl, 3 mmol) of pyridine-3-carbaldehyde, and 1.5 ml of 2N ethanolic KOH in 10 ml of absolute ethanol was added approx. 1 g of mol sieves (0.4 nm), and it was stirred for 16 h at ambient temperature. The mixture was filtered and the filtrate evaporated. The residue was chromatographed on silica gel with a hexane/acetone gradient (0 to 20% acetone).

yield: 360 mg (36%)

Step B: Ethyl 5-Chloro-2-(pyridin-3-yl)-1H-indole-3-carboxylate

A solution of 350 mg (1.05 mmol) of the compound from Step A, in 6 ml of neat triethyl phosphite was stirred at 140° C. for 3 h. Excess triethyl phosphite was removed in vacuo, and the residue was dissolved in a small amount of ethanol together with approx. 500 mg of silica gel. The slurry was evaporated to dryness, and the remaining powder loaded onto a column containing silica gel. The title compound was obtained by chromatography with a hexane/acetone gradient (0 to 50% acetone).

yield: 100 mg (33%).

Step C: 5-Chloro-3-(4,5-dihydro-1H-imidazol-2-yl)-2-(pyridin-3-yl)-1H-indole A solution of 100 mg (0.3 mml) of the ester obtained in Step B, in 2 ml of ethylenediamine and 50 μl of water was stirred for 14 d at 100° C. The mixture was evaporated to dryness, triturated with a minimum of dichloromethane/ethanol, and the precipitate was collected by filtration and dried in vacuo. The mother liquid was purified via silica gel chromatography using a dichloromethane/ethanolic ammonia gradient (98:2 to 80:20). The precipitate and the chromatographed material was collected to give 65 mg (65%) of the 2-aminoethylamide.

To a solution of 65 mg (0.2 mmol) of the 2-aminoethylamide in 4 ml of dichloromethane 200 mg of diethylaminomethyl polystyrene and 86 μl of TMS iodide were added. After stirring for 3 d at ambient temperature another 57 μl of TMS iodide and 130 mg of the resin were added. Stirring was continued for another 4 d followed by repeated additon of an equal amount of TMS iodide and resin. After another 5 d of stirring the resin was removed by filtration, the filtrate was evaporated, and the residue purified via column chromatography on silica gel.

yield: 10 mg (16%); brown amorphous solid.

EXAMPLE 84

5-Chloro-3-(4,5-dihydro-1H-imidazol-2-yl)-2-(pyridin-4-yl)-1H-indole (X=Cl, R=4-pyridyl)

This compound was prepared in the essentially the same manner as described in Example 85, and obtained as a yellow amorphous solid.

EXAMPLE 85

3-(4,5-Dihydroimidazol-2-yl)-2-(4-methylphenyl)-5-trifluoromethoxy-1H-indole Hydrochloride (X=OCF$_3$, R=4-methylphenyl)

Step A: 2-(4-Methylphenyl)-5-trifluoromethoxy-1H-indole

To a stirred solution of 5.3 g (30 mmol) of 4-trifluoromethoxyaniline in 8 ml of N,N-diethylaniline was added dropwise at 165° C. a solution of 4.3 g of 4-methylphenacyl bromide in 7.5 ml of xylene. It was heated at 165° C. for 3 h. The mixture was cooled followed by addition of 50 ml of ethyl acetate. It was washed with 2N hydrochloric acid, and the aqueous layer was extracted with ethyl acetate. The combined organic layers were dried over sodium sulfate and concentrated under reduced pressure. The residue was purified via repeated column chromatography on silica gel using a hexane dichloromethane gradient (100:0 to 50:50). The title compound thus obtained was recrystallized from hexane.

yield: 400 mg (5%).

Step B: 3-(4,5-Dihydroimidazol-2-yl)-244-methylphenyl)-5-trifluoromethoxy-1H-indole Hydrochloride 380 mg (1.3 mmol) of the indole from Step A was heated with 210 mg (1.6 mmol) of N-acetyl-2-imidazolinone in 1.3 ml of neat phosphoryl chloride at 60° C. for 20 h. The excess of phosphoryl chloride was removed under reduced pressure, and the residue was dissolved in 2 ml of absolute ethanol and heated at 60° C. for 5 h. The mixture was cooled, and the crystalline precipitate collected by filtration, washed with ethanol, and dried in vacuo.

yield: 370 mg (70%); pale yellow crystals, m.p. >250° C.

EXAMPLE 86

2-(2-Chlorophenyl)-3-(4,5-dihydroimidazol-2-yl)-5-trifluoromethoxy-1H-indole (X=OCF$_3$, R=2-chlorophenyl)

The compound was prepared in essentially the same manner as described in Example 85, and obtained as a beige amorphous solid.

EXAMPLE 87

3-(4,5-Dihydroimidazol-2-yl)-2-(4-methylphenyl)-5-trifluoromethylthio-1H-indole Hydrochloride (X=SCF$_3$, R=4-methylphenyl)

The imidazoline was prepared in essentially the same manner as described in Example 85, starting from 4-(trifluoromethylthio)aniline and obtained as a colorless crystalline solid.

EXAMPLE 88

2-(6-Aryl-naphthalene-2-yl)-4,5-dihydro-1H-imidazoles

The compounds of Examples 88a to 88g, shown in Table I below, were prepared from methyl-6-bromo-2-naphthoate as described in Scheme X, above. The general conditions for the Suzuki reaction were as follows:

To a solution of immol of the bromo compound in 20 ml 1,4-dioxane is added under argon 0.1 mmol Pd(PPh$_3$)$_4$ and 2 ml 2M Na$_2$CO$_3$. After stirring at room temperature for 20 minutes, 1.5 mmol of the aryl boronic acid is added and the mixture is heated for 20 ours at 80° C. The mixture is cooled to room temperature and filtered to remove the solid. The solution is acidified with 2N HCl and chromatographed on silica gel.

TABLE I

| E.g. # | Structure | Name | Yield | mp. | MS |
|---|---|---|---|---|---|
| 88a | 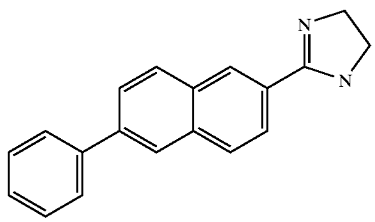 | 6-(Phenyl)-naphthalene-2-yl)-4,5-dihydro-1H-imidazole | 55% | amorphous | 272 M+ |
| 88b | 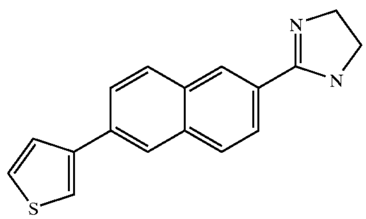 | 6-(3-Thienyl)-naphthalene-2-yl)-4,5-dihydro-1H-imidazole | 68% | amorphous | 278 M+ |
| 88c | 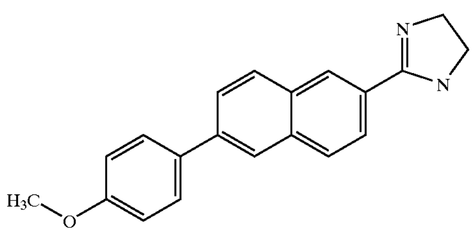 | 6-(4-Methoxyphenyl)-naphthalene-2-yl)4,5-dihydro-1H-imidazole | 50% | amorphous | 302 M+ |
| 88d | 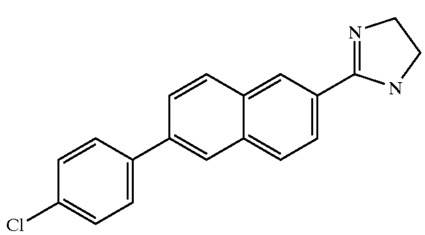 | 6-(4-Chlorophenyl)-naphthalene-2-yl)4,5-dihydro-1H-imidazole | 60% | amorphous | 306 M+ |
| 88e | 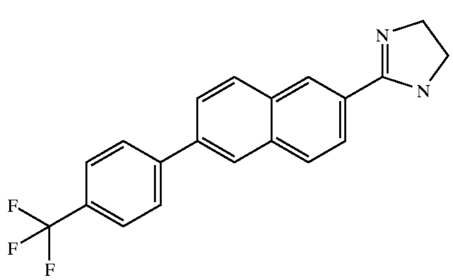 | 2-[6-(4-Trifluoromethylphenyl)-naphthalene-2-yl]-4,5-dihydro-1H-imidazole | 50% | amorphous | 340 M+ |
| 88f | 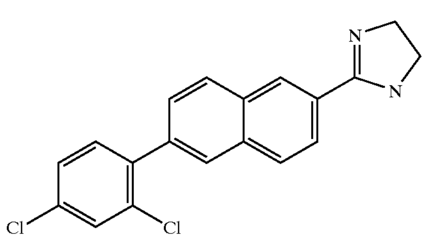 | 2-[6-(2,4-Dichlorophenyl)-naphthalene-2-yl]-4,5-dihydro-1H-imidazole | 61% | amorphous | 341 M+ |

TABLE I-continued

| E.g. # | Structure | | Yield | mp. | MS |
|---|---|---|---|---|---|
| 88g | 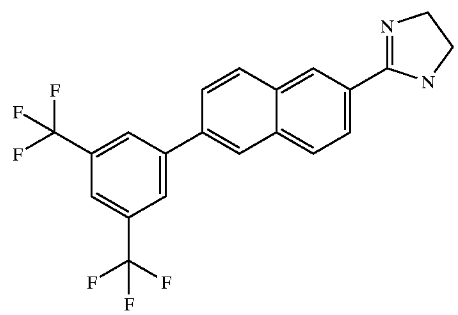 | 2-[6-(3,5-Bis(trifluoromethyl)-phenyl)naphthalen-2-yl]-4,5-dihydro-1H-imidazole | 53% | amorphous | 408 M+ |

EXAMPLE 89

5-Chloro-2-benzyl-3-(4,5-dihydroimidazol-2-yl)-1H-indole

Step 1: 3.85 g (30 mmol) 5-chloroindole was treated with 6.84 g (40 mmol) benzylbromide, 1.97 g (30 mmol) potassium hydroxide (85% powdered in mortar) and 0.25 g (1 mmol) 18-crown-6 as described in Synthesis 1979 p. 618, giving 4.35 g (60%) 5-chloro-1-benzyl-1H-indole, yellow oil, MS (Ei 70 eV) m/Z M+241.

Step 2: 2.42 g (10 mmol) 5-chloro-1-benzylindole was heated at 140° with PPA as described in Synth. Commun. 27 (1997) p. 2036 giving 2.0 g (83%) 5-chloro-2-benzyl-1H-indole, yellow oil, MS (Ei 70 eV) m/Z M+241.

Step 3: A mixture of 2.42 g (10 mmol) 5-chloro-2-benzylindole and 1.28 g (10 mmol) 1-acetyl-imidazolidine-2-one (0.1 mol) is added to phosphorus oxychloride (10 ml) and heated to 60° C. for 5 hours. After evaporation of phosphorus oxychloride the residue is treated with ethanol (14 ml) and heated to reflux for 3.5 hours. Ethanol is evaporated. The residue is purified by chromatography to obtain the hydrochloride. The base is obtainable by treatment with 2N sodium hydroxide to pH 11. The solid is filtered off and dried in vacuo. Hydrochloride, m.p. 299–300° C., M.S. (Ei 70 ev) m/Z M=309.

The compounds of Table II, Examples 89a to 89c, were prepared essentially as described in Example 89.

TABLE II

| E.g. # | Structure | | Yield | mp. | MS |
|---|---|---|---|---|---|
| 89a | 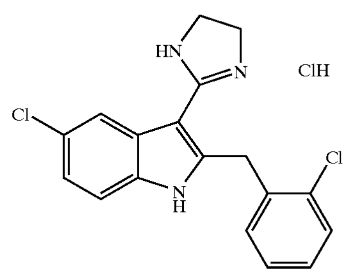 | 3-(4,5-Dihydro-1H-imidazol-2-yl)-5-chloro-2-(2-chlorbenzyl)-1H-indole Hydrochloride | 29% | >300° C. | 344 |
| 89b | 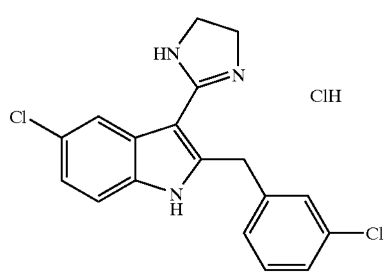 | 3-(4,5-Dihydro-1H-imidazol-2-yl)-5-chloro-2-(3-chlorbenzyl)-1H-indole Hydrochloride | 10% | 270–271° (Z) | 344 |

TABLE II-continued

| E.g. # | Structure | | Yield | mp. | MS |
|---|---|---|---|---|---|
| 89c | *[structure: 5-chloro-2-(4-chlorobenzyl)-3-(4,5-dihydro-1H-imidazol-2-yl)-1H-indole]* | 3-(4,5-Dihydro-1H-imidazol-2-yl)-5-chloro-2-(4-chlorbenzyl)-1H-indole Hydrochloride | 26% | >300° C. | 344 |

EXAMPLE 90

5-Chloro-2-methyl-1-benzyl-3-(4,5-dihydroimidazol-2-yl)-1H-indole

Step 1: 4.97 g (30 mmol) 5-chloro-2-methylindole was treated with 6.84 g (40 mmol) benzyl bromide, 1.97 g (30 mmol) potassium hydroxide (85% powdered in mortar) and 0.25 g (1 mmol) 18-crown-6 as described in Synthesis 1979, p. 618 to give 3.22 g (42%) 5-chloro-2-methyl-1-benzyl-1H-indole, mp: 75–76°, MS (Ei 70 eV) m/Z M+255.

Step 2: 2.56 g (10 mmol) 5-chloro-2-methyl-1-benzylindole was treated with 1.28 g (10 mmol) 1-acetyl-imidazolidin-2-one and 10 ml phosphorous oxychloride as described in Example 89, Step 1 to give 0.65 g (18%) 3-(4,5-dihydro-1H-imidazol-2-yl)-5-chloro-2-methyl-1-benzyl-1H-indole Hydrochloride, mp: 273–275°, MS (Ei 70 eV) m/Z M+323.

The compounds of Table III, Examples 90a to 90c, were prepared essentially as described in Example 90.

TABLE III

| E.g. # | Structure | | Yield | mp. | MS |
|---|---|---|---|---|---|
| 90a | *[structure]* | 3-(4,5-Dihydro-1H-imidazol-2-yl)-5-chloro-2-methyl-1-(2-chlorobenzyl)-1H-indole Hydrochloride | 17% | 299–300° | 358 |
| 90b | *[structure]* | 3-(4,5-Dihydro-1H-imidazol-2-yl)-5-chloro-2-methyl-1-(3-chlorobenzyl)-1H-indole Hydrochloride | 40% | amorphous | 358 |

TABLE III-continued

| E.g. # | Structure | | Yield | mp. | MS |
|---|---|---|---|---|---|
| 90c | (structure) | 3-(4,5-Dihydro-1H-imidazol-2-yl)-5-chloro-2-methyl-1-(4-chlorobenzyl)-1H-indole Hydrochloride | 24% | amorphous | 358 |

EXAMPLE 91

Optionally substituted aryl and heteroaryl 2-(4,5-dihydro-1H-imidazol-2-yl)benzofurans The compounds of Table IV, Examples 91a–91aj were prepared as follows:

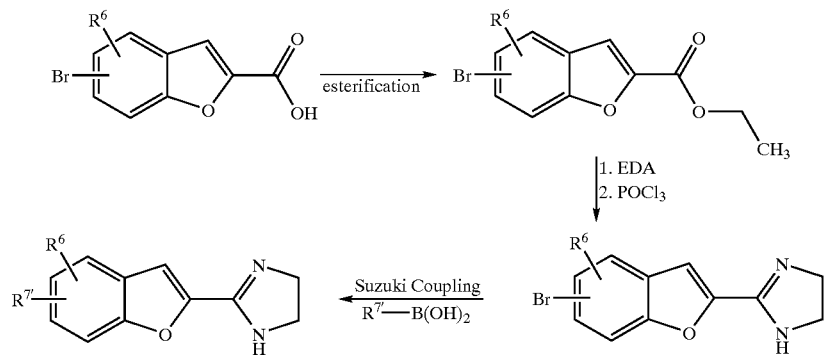

As illustrated herein, by the above scheme, $R^6$ is as defined by Formula I and $R^{7'}$ is an aryl or heteroaryl.

Bromobenzofurancarboxylic acids were prepared according to procedures known in the art, for example, as described in Helv. Chim. Acta 1954, p. 436, followed by the esterifications of the acids. The esters were converted into the imidazolines according to the procedure as described, for example, in Example 16, followed by applying the Suzuki-reaction as described, for example, in Example 88.

TABLE IV

| E.g. # | Structure | | Yield | mp. | MS |
|---|---|---|---|---|---|
| 91a | (structure) | 2-(4-(5-Chloro-2-thienyl)-2-benzofuranyl)-4,5-dihydro-1H-imidazole Hydrochloride | 56% | 158–160° C. | 302 |

TABLE IV-continued

| E.g. # | Structure | | Yield | mp. | MS |
|---|---|---|---|---|---|
| 91b | 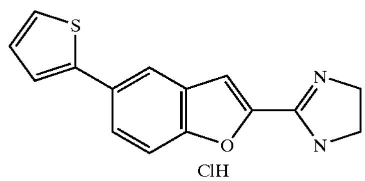 | 2-(5-(2-Thienyl)-2-benzofuranyl)-4,5-dihydro-1H-imidazole Hydrochloride | 41% | 284–286° C. | 268 |
| 91c | 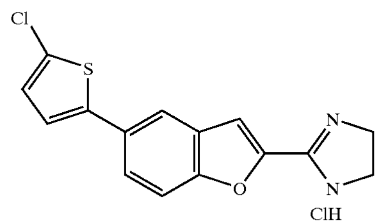 | 2-(5-(5-Chloro-2-thienyl)-2-benzofuranyl)-4,5-dihydro-1H-imidazole Hydrochloride | 15% | amorphous | 302 |
| 91d | 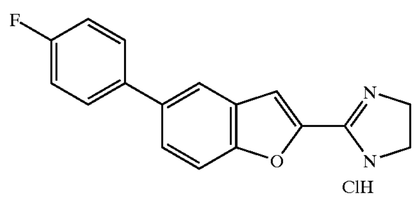 | 2-(5-(4-Fluorophenyl)-2-benzofuranyl)-4,5-dihydro-1H-imidazole Hydrochloride | 22% | amorphous | 280 |
| 91e | 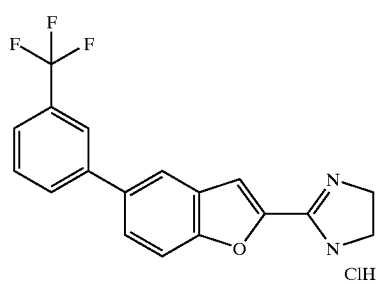 | 2-(5-(3-Trifluoromethylphenyl)-2-benzofuranyl)-4,5-dihydro-1H-imidazole Hydrochloride | 19% | amorphous | 330 |
| 91f | 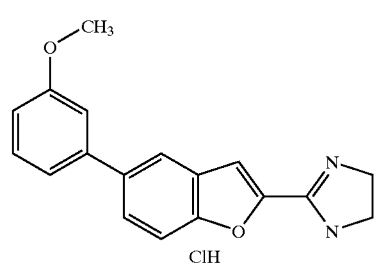 | 2-(5-(3-Methoxyphenyl)-2-benzofuranyl)-4,5-dihydro-1H-imidazole Hydrochloride | 44% | 246–248° C. | 292 |
| 91g | 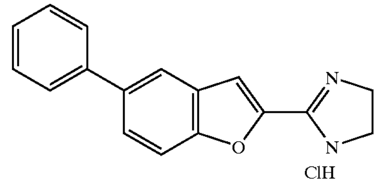 | 2-(5-Phenyl-2-benzofuranyl)-4,5-dihydro-1H-imidiazole Hydrochloride | 20% | 252–254° C. | 262 |

TABLE IV-continued

| E.g. # | Structure | | Yield | mp. | MS |
|---|---|---|---|---|---|
| 91h | 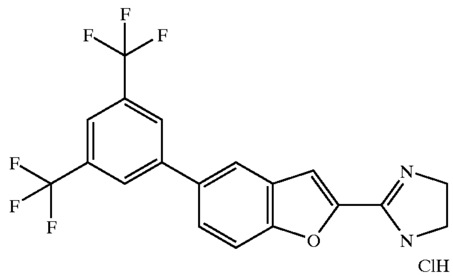 | 2-(5-(3,5-Bistrifluoromethyl-phenyl)-2-benzofuranyl)-4,5-dihydro-1H-imidazole Hydrochloride | 25% | amorphous | 398 |
| 91I | 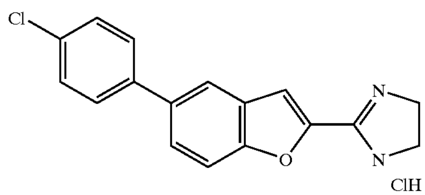 | 2-(5-(4-Chlorophenyl)-2-benzofuranyl)-4,5-dihydro-1H-imidazole Hydrochloride | 20% | amorphous | 296 |
| 91j | 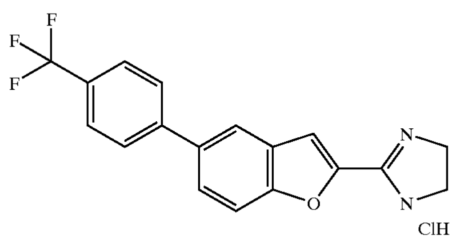 | 2-(5-(4-Trifluoromethyl-phenyl)-2-benzofuranyl)-4,5-dihydro-1H-imidazole Hydrochloride | 27% | amorphous | 330 |
| 91k | 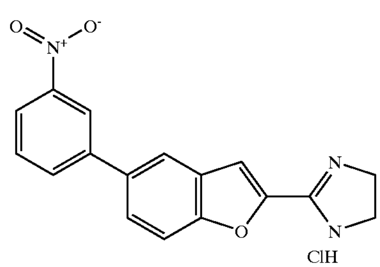 | 2-(5-(3-Nitrophenyl)-2-benzofuranyl)-4,5-dihydro-1H-imidazole Hydrochloride | 32% | amorphous | 307 |
| 91l | 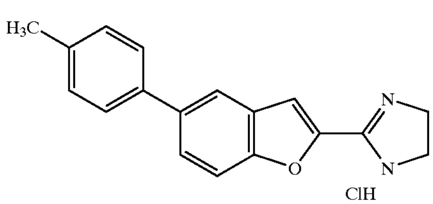 | 2-(5-(4-Methylphenyl)-2-benzofuranyl)-4,5-dihydro-1H-imidazole Hydrochloride | 20% | amorphous | 276 |
| 91m | 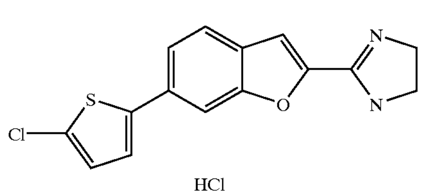 | 2-(6-(5-Chloro-2-thienyl)-2-benzofuranyl)-4,5-dihydro-1H-imidazole Hydrochloride | 67% | 292–294° C. | 302 |

TABLE IV-continued

| E.g. # | Structure | | Yield | mp. | MS |
|---|---|---|---|---|---|
| 91n | 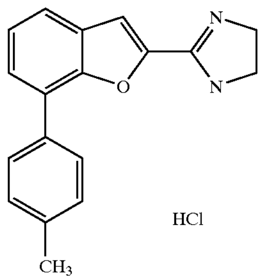 | 2-(7-(4-Methylphenyl)-2-benzofuranyl)-4,5-dihydro-1H-imidazole Hydrochloride | 41% | 294–296° C. | 276 |
| 91o | 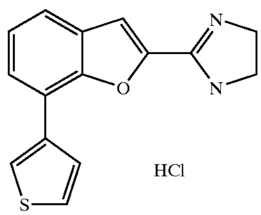 | 2-(7-(3-Thienyl)-2-benzofuranyl)-4,5-dihydro-1H-imidazole Hydrochloride | 56% | amorphous | 268 |
| 91p | 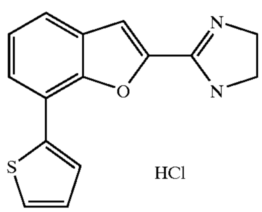 | 2-(7-(2-Thienyl)-2-benzofuranyl)-4,5-dihydro-1H-imidazole Hydrochloride | 43% | 246–248° C. | 268 |
| 91q | 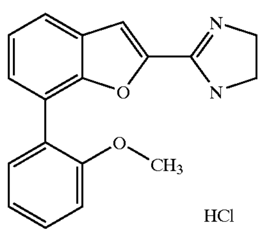 | 2-(7-(2-Methoxyphenyl)-2-benzofuranyl)-4,5-dihydro-1H-imidazole Hydrochloride | 64% | 266–268° C. | 292 |
| 91r | 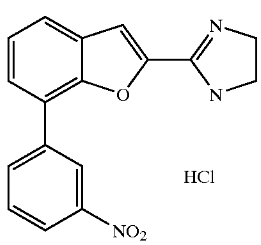 | 2-(7-3-Nitrophenyl)-2-benzofuranyl)-4,5-dihydro-1H-imidazole Hydrochloride | 44% | 298–300° C. | 307 |
| 91s | 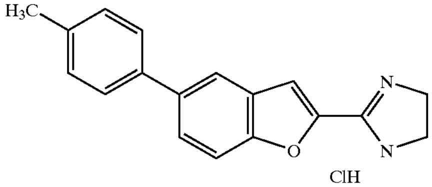 | 2-(5-(4-methylphenyl)-2-benzofuranyl)-4,5-dihydro-1H-imidazole Hydrochloride | 24% | amorphous | 276 |

TABLE IV-continued

| E.g. # | Structure | | Yield | mp. | MS |
|---|---|---|---|---|---|
| 91t | (structure) | 2-(5-(4-methoxyphenyl)-2-benzofuranyl)-4,5-dihydro-1H-imidazole Hydrochloride | 32% | amorphous | 292 |
| 91u | (structure) | 2-(5-(3-trifluoromethylphenyl)-2-benzofuranyl)-4,5-dihydro-1H-imidazole Hydrochloride | 36% | amorphous | 330 |
| 91v | (structure) | 2-(5-(4-fluorolphenyl)-2-benzofuranyl)-4,5-dihydro-1H-imidazole Hydrochloride | 35% | amorphous | 280 |
| 91w | (structure) | 2-(5-(4-methylthiophenyl)-2-benzofuranyl)-4,5-dihydro-1H-imidazole Hydrochloride | 28% | amorphous | 308 |
| 91x | (structure) | 2-(5-(3-fluorophenyl)-2-benzofuranyl)-4,5-dihydro-1H-imidazole Hydrochloride | 39% | amorphous | 316 |
| 91y | (structure) | 2-(5-(2-methoxyphenyl)-2-benzofuranyl)-4,5-dihydro-1H-imidazole Hydrochloride | 37% | amorphous | 328 |

TABLE IV-continued

| E.g. # | Structure | | Yield | mp. | MS |
|---|---|---|---|---|---|
| 91z | 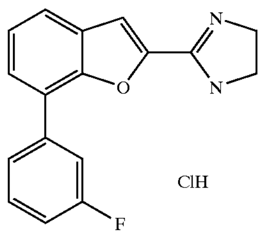 | 2-(7-(3-fluorophenyl)-2-benzofuranyl)-4,5-dihydro-1H-imidazole Hydrochloride | 28% | 247° C. | 316 |
| 91aa | 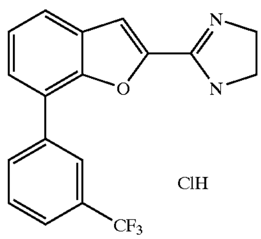 | 2-(7-(3-trifluoromethylphenyl)-2-benzofuranyl)-4,5-dihydro-1H-imidazole Hydrochloride | 40% | >300° C. | 366 |
| 91ab | 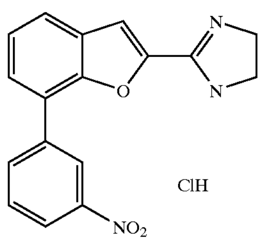 | 2-(7-(3-nitrophenyl)-2-benzofuranyl)-4,5-dihydro-1H-imidazole Hydrochloride | 42% | >300° C. | 343 |
| 91ac | 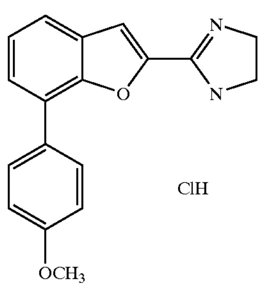 | 2-(7-(4-methoxyphenyl)-2-benzofuranyl)-4,5-dihydro-1H-imidazole Hydrochloride | 45% | >300° C. | 328 |
| 91ad | 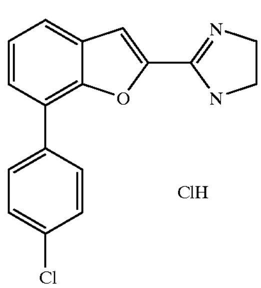 | 2-(7-(4-chlorophenyl)-2-benzofuranyl)-4,5-dihydro-1H-imidazole Hydrochloride | 44% | >300° C | 333 |
| 91ae | 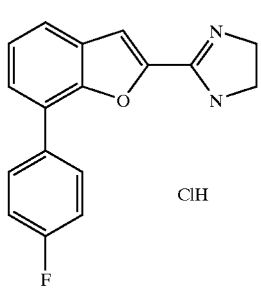 | 2-(7-(4-fluorophenyl)-2-benzofuranyl)-4,5-dihydro-1H-imidazole Hydrochloride | 39% | >300° C. | 316 |

TABLE IV-continued

| E.g. # | Structure | | Yield | mp. | MS |
|---|---|---|---|---|---|
| 91af | (structure) | 2-(4-(2-thienyl)-2-benzofuranyl)-4,5-dihydro-1H-imidazole Hydrochloride | 25% | 156° C. | 304 |
| 91ag | (structure) | 2-(4-(3-thienyl)-2-benzofuranyl)-4,5-dihydro-1H-imidazole Hydrochloride | 28% | 181° C. | 304 |
| 91ah | (structure) | 2-(4-(2-(5-chloro)-thienyl)-2-benzofuranyl)-4,5-dihydro-1H-imidazole Hydrochloride | 30% | 156° C. | 339 |
| 91ai | (structure) | 2-(4-(3-nitrophenyl)-2-benzofuranyl)-4,5-dihydro-1H-imidazole Hydrochloride | 32% | 160° C. | 343 |
| 91aj | (structure) | 2-(4-(3-fluorophenyl)-2-benzofuranyl)-4,5-dihydro-1H-imidazole Hydrochloride | 33% | 135° C. | 316 |

EXAMPLE 92

5-optionally substituted aryl- and optionally substituted heteroaryl 2-methyl-3-(4,5-dihydro-1H-imidazolin-2-yl)-1H-indoles The compounds of Table V, Examples 92a to 92s, were prepared by Suzuki coupling, for example, as described by Examples 91.

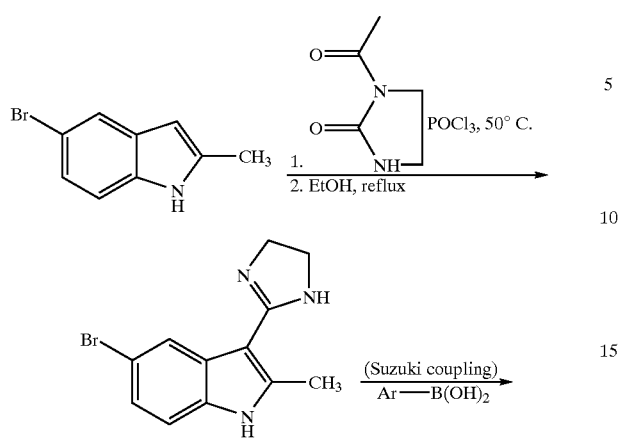

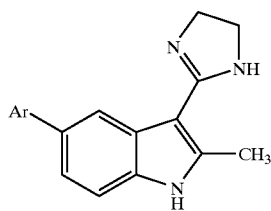

TABLE V

| E.g. # | Structure | | Yield | mp. | MS |
|---|---|---|---|---|---|
| 92a | (structure) | 5-Phenyl-3-(4,5-dihydro-1H-imidazol-2-yl)-2-methyl-1H-indole Hydrochloride | 38% | <300° C. | 275 |
| 92b | (structure) | 5-(2-Thienyl)-3-(4,5-dihydro-1H-imidazol-2-yl)-2-methyl-1H-indole Hydrochloride | 63% | amorphous | 281 |
| 92c | (structure) | 5-(4-Chlorophenyl)-3-(4,5-dihydro-1H-imidazol-2-yl)-2-methyl-1H-indole Hydrochloride | 35% | amorphous | 309 |
| 92d | (structure) | 5-(3-Trifluoromethyl-phenyl)-3-(4,5-dihydro-1H-imidazol-2-yl)-2-methyl-1H-indole Hydrochloride | 34% | amorphous | 343 |

TABLE V-continued

| E.g. # | Structure | | Yield | mp. | MS |
|---|---|---|---|---|---|
| 92e | 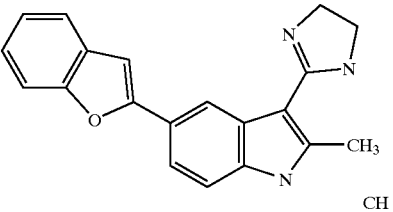 | 5-(2-Benzofuranyl)-3-(4,5-dihydro-1H-imidazol-2-yl)-2-methyl-1H-indole Hydrochloride | 51% | amorphous | 315 |
| 92f | 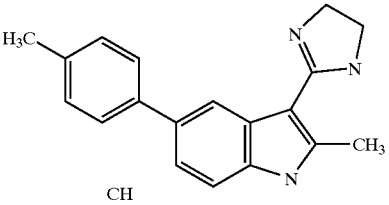 | 5-(4-Methylphenyl)-3-(4,5-dihydro-1H-imidazol-2-yl)-2-methyl-1H-indole Hydrochloride | 22% | amorphous | 289 |
| 92g | 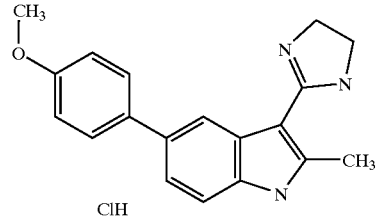 | 5-(4-Methoxyphenyl)-3-(4,5-dihydro-1H-imidazol-2-yl)-2-methyl-1H-indole Hydrochloride | 24% | amorphous | 305 |
| 92h | 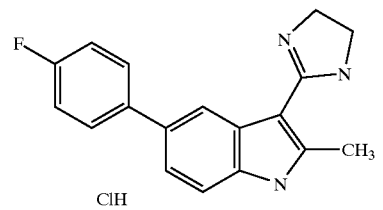 | 5-(4-Fluorophenyl)-3-(4,5-dihydro-1H-imidazol-2-yl)-2-methyl-1H-indole Hydrochloride | 21% | amorphous | 293 |
| 92i | 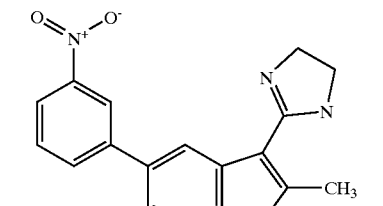 | 5-(3-Nitrophenyl)-3-(4,5-dihydro-1H-imidazol-2-yl)-2-methyl-1H-indole Hydrochloride | 19% | amorphous | 320 |
| 92j | 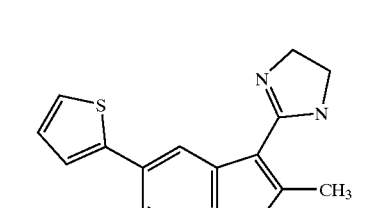 | 5-(2-Thienyl)-3-(4,5-dihydro-1H-imidazol-2-yl)-2-methyl-1H-indole Hydrochloride | 26% | amorphous | 281 |

TABLE V-continued

| E.g. # | Structure | | Yield | mp. | MS |
|---|---|---|---|---|---|
| 92k | 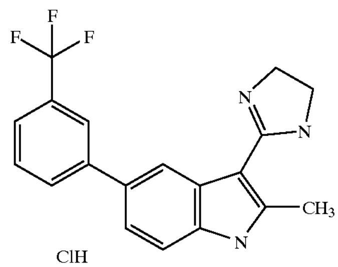 | 5-(3-Trifluoromethylphenyl)-3-(4,5-dihydro-1H-imidazol-2-yl)-2-methyl-1H-indole Hydrochloride | 28% | amorphous | 343 |
| 92l | 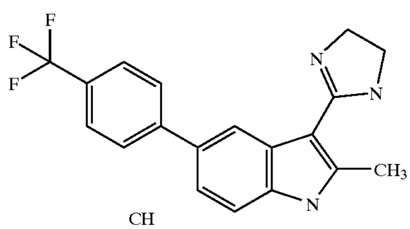 | 5-(4-Trifluoromethylphenyl)-3-(4,5-dihydro-1H-imidazol-2-yl)-2-methyl-1H-indole Hydrochloride | 16% | amorphous | 343 |
| 92m | 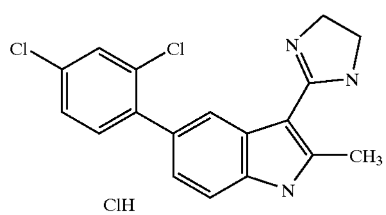 | 5-(2,4-Dichlorophenyl)-3-(4,5-dihydro-1H-imidazol-2-yl)-2-methyl-1H-indole Hydrochloride | 31% | amorphous | 344 |
| 92n | 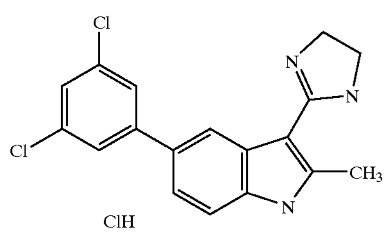 | 5-(3,5-Dichlorophenyl)-3-(4,5-dihydro-1H-imidazol-2-yl)-2-methyl-1H-indole Hydrochloride | 28% | amorphous | 344 |
| 92o | 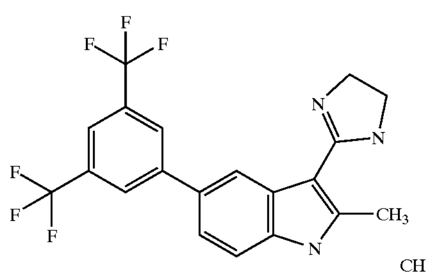 | 5-(3,5-Bistrifluoromethyl-phenyl)-3-(4,5-dihydro-1H-imidazol-2-yl)-2-methyl-1H-indole Hydrochloride | 16% | amorphous | 411 |
| 92p | 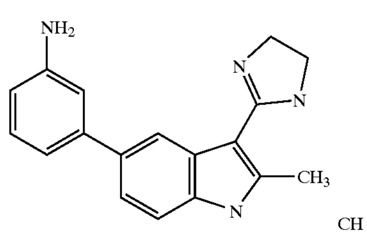 | 5-(3-Amino-phenyl)-3-(4,5-dihydro-1H-imidazol-2-yl)-2-methyl-1H-indole Hydrochloride | 18% | amorphous | 290 |

TABLE V-continued

| E.g. # | Structure | | Yield | mp. | MS |
|---|---|---|---|---|---|
| 92q | [5-(1-Naphthyl) indole with imidazoline and 2-methyl, CH salt] | 5-(1-Napthyl)-3-(4,5-dihydro-1H-imidazol-2-yl)-2-methyl-1H-indole Hydrochloride | 22% | amorphous | 325 |
| 92r | [5-(5-Chloro-2-thienyl) indole structure, ClH salt] | 5-(5-Chloro-2-thienyl)-3-(4,5-dihydro-1H-imidazol-2-yl)-2-methyl-1H-indole Hydrochloride | 18% | amorphous | 316 |
| 92s | [5-(4-Bromophenyl) indole structure, ClH salt] | 5-(4-Bromophenyl)-3-(4,5-dihydro-1H-imidazol-2-yl-2-methyl-1H-indole Hydrochloride | 18% | amorphous | 354 |

EXAMPLE 93

5-Chloro-2-phenylthio-3-(4,5-dihydro-1H-imidazol-2-yl)-1H-indole

5-Chloro-3-phenylthio-1H-indole was prepared according to the procedure as described in Synthesis, June 1988, 480–481. 5-Chloro-1H-indole (0.021 mol, 3.19 g) gave 5-chloro-3-(phenylthio)-1H-indole (4 g): MS:259MH+; m.p.109° C.; yield (74.6%).

Isomerisation of the 3-phenylthio-1H-indole to 2-phenylthio-1H-indole is described in J.Org.Chem. 1992, 57, 2694–2699. 5-Chloro-3-(phenythio)-1H-indole (0.015 mol, 4 g) gave 5-chloro-2-(phenylthio)-1H-indole (2.3 g): MS:259MH−; m.p.58° C.; yield (57.5%).

Treatment of 5-chloro-2-(phenylthio)-1H-indole (3.8 mmol, 1 g) with N-acetyl-4,5-dihydro-1H-imidazol-2-one as described in Example 89, Step 3 gave 5-chloro-2-phenylthio-3-(4,5-dihydro-1H-imidazol-2-yl)-1H-indole (0.19 g): MS:327M−; m.p.178° C.; yield (13,4%).

EXAMPLE 94

4-Optionally substituted aryl- and heteroaryl-2-(4,5-dihydro-1H-imidazolin-2-yl) napthalenes The compounds of Table VI, Examples 94a to 94ai, are prepared by methods known in the art, or by the procedures as described herein, for example in Scheme IV.

TABLE VI

| Structure and E.g. # | | Name | Yield % | MS (M+) | M.P. ° C. |
|---|---|---|---|---|---|
| 94a | [naphthalene with imidazoline, 2-methoxyethoxy group, and 4-fluorophenyl, ClH salt] | 2-[4-(4-Fluorophenyl)-3-(2-methoxyethoxy)naphthalen-2-yl]-4,5-1H-imidazole Hydrochloride | 27 | 364 | amorphous |

TABLE VI-continued

| Structure and E.g. # | | Name | Yield % | MS (M+) | M.P. °C. |
|---|---|---|---|---|---|
| 94b | 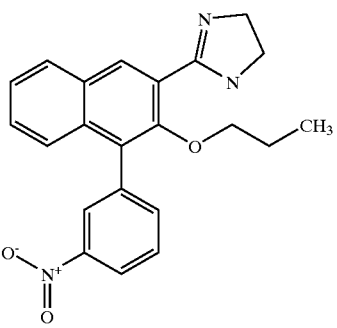 | 2-[4-(3-Nitrophenyl)-3-propoxynaphthalen-2-yl]-4,5-1H-imidazol | 29 | 375 | amorphous |
| 94c | 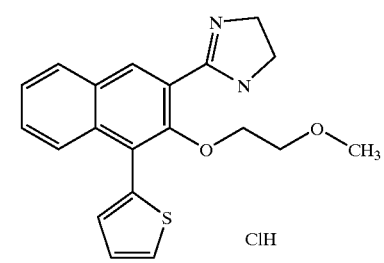 | 2-[3-(2-Methoxyethoxy)-4-(2-thienyl)naphthalen-2-yl]-4,5-1H-imidazole Hydrochloride | 31 | 389 | amorphous |
| 94d | 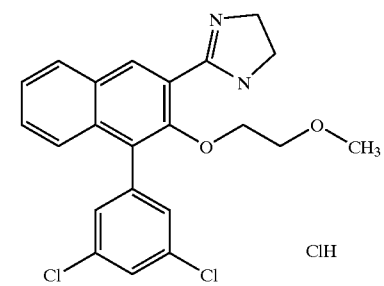 | 2-[4-(3,5-Dichlorophenyl)-3-(2-methoxyethoxy)naphthalen-2-yl]-4,5-dihydro-1H-imidazole Hydrochloride | 33 | 415 | 178 |
| 94e | 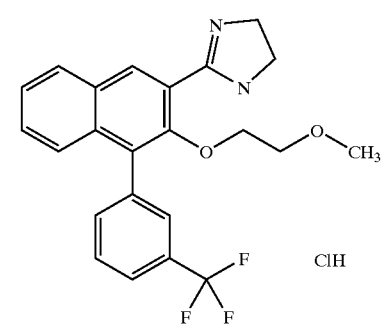 | 2-[3-(2-Methoxyethoxy)-4-(3-trifluoromethylphenyl)naphthalen-2-yl]-4,5-dihydro-1H-imidazole Hydrochloride | 25 | 414 | 124 |
| 94f | 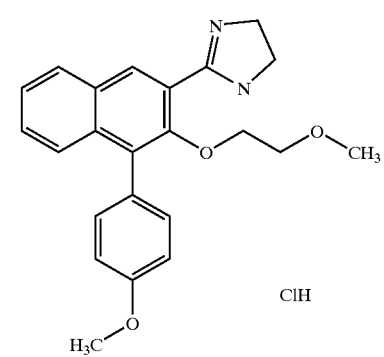 | 2-[3-(2-Methoxyethoxy)-4-(4-methoxyphenyl)naphthalen-2-yl]-4,5-dihydro-1H-imidazole Hydrochloride | 37 | 377 | 227 |

TABLE VI-continued

| Structure and E.g. # | | Name | Yield % | MS (M+) | M.P. °C. |
|---|---|---|---|---|---|
| 94g | 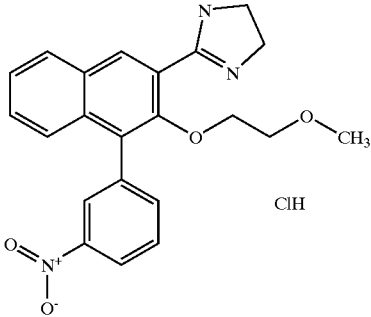 | 2-[3-(2-Methoxyethoxy)-4-(3-nitrophenyl)naphthalen-2-yl]-4,5-dihydro-1H-imidazole Hydrochloride | 28 | 391 | 195 |
| 94h | 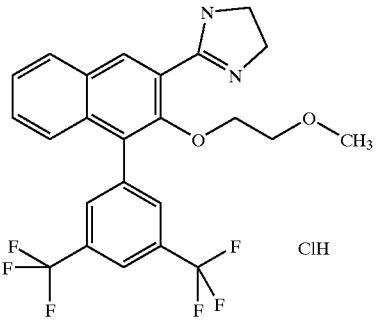 | 2-[3-(2-Methoxyethoxy)-4-(3,5-bis(trifluoromethyl)phenyl)-naphthalen-2-yl]-4,5-dihydro-1H-imidazole Hydrochloride | 22 | 482 | 223 |
| 94i | 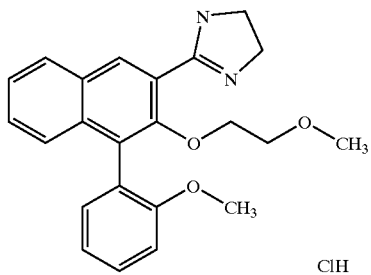 | 2-[3-(2-Methoxyethoxy)-4-(2-methoxyphenyl)naphthalen-2-yl]-4,5-dihydro-1H-imidazole Hydrochloride | 36 | 377 | 202 |
| 94j | 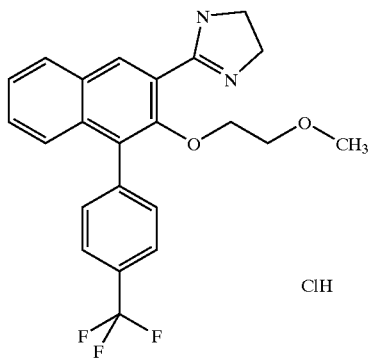 | 2-[3-(2-Methoxyethoxy)-4-(4-trifluoromethylphenyl)naphthalen-2-yl]-4,5-dihydro-1H-imidazole Hydrochloride | 31 | 414 | 154 |

TABLE VI-continued

| Structure and E.g. # | Name | Yield % | MS (M+) | M.P. ° C. |
|---|---|---|---|---|
| 94k | 2-[3-(2-Methoxyethoxy)-4-(4-methylthiophenyl)naphthalen-2-yl]-4,5-dihydro-1H-imidazole Hydrochloride | 17 | 393 | 220 |
| 94l | 2-[4-(2,4-Dichlorphenyl)-3-propoxynaphthalen-2-yl]-4,5-dihydro-1H-imidazole Hydrochloride | 38 | 399 | 181 |
| 94m | 2-[3-(2-Methoxyethoxy)-4-(2-methylphenyl)naphthalen-2-yl]-4,5-dihydro-1H-imidazole Hydrochloride | 35 | 361 | 122 |
| 94n | 2-[4-(3-Chlorophenyl)-3-(2-methoxyethoxy)naphthalen-2-yl]-4,5-dihydro-1H-imidazole Hydrochloride | 31 | 381 | 192 |
| 94o | 2-[4-(2-Chlorophenyl)-3-(2-methoxyethoxy)naphthalen-2-yl]-4,5-dihydro-1H-imidazole Hydrochloride | 34 | 381 | 210 |

TABLE VI-continued

| Structure and E.g. # | Name | Yield % | MS (M+) | M.P. °C. |
|---|---|---|---|---|
| 94p | 2-[4-(3-Chloro-4-fluorophenyl)-3-(2-methoxyethoxy)naphthalen-2-yl]-4,5-dihydro-1H-imidazole Hydrochloride | 23 | 399 | 204 |
| 94q | 2-[4-(3,4-Dichlorophenyl)-3-(2-methoxyethoxy)naphthalen-2-yl]-4,5-dihydro-1H-imidazole Hydrochloride | 25 | 414 | 199 |
| 94r | 2-[4-(2,3-Dichlorophenyl)-3-(2-methoxyethoxy)naphthalen-2-yl]-4,5-dihydro-1H-imidazole Hydrochloride | 21 | 414 | 179 |
| 94s | 2-[4-(4-Chlorophenyl)-3-(2-ethoxyethoxy)naphthalen-2-yl]-4,5-dihydro-1H-imidazole Hydrochloride | 27 | 394 | 221 |

TABLE VI-continued

| Structure and E.g. # | Name | Yield % | MS (M+) | M.P. °C. |
|---|---|---|---|---|
| 94t | 2-[4-(4-Chlorophenyl)-3-butoxynaphthalen-2-yl]-4,5-dihydro-1H-imidazole Hydrochloride | 38 | 379 | amorphous |
| 94u | 2-[4-(4'-Chloro-4-biphenyl)-3-(2-methoxyethoxy)naphthalen-2-yl]-4,5-dihydro-1H-imidazole Hydrochloride | 22 | 457 | amorphous |
| 94v | 2-[4-(4-Chlorophenyl)-3-(cyclobutylmethoxy)naphthalen-2-yl]-4,5-dihydro-1H-imidazole Hydrochloride | 8 | 391 | 228 |
| 94w | 2-[4-(3-Chloro-4-fluorophenyl)-3-(2-ethoxyethoxy)naphthalen-2-yl]-4,5-dihydro-1H-imidazole Hydrochloride | 20 | 412 | 200 |

TABLE VI-continued

| Structure and E.g. # | | Name | Yield % | MS (M+) | M.P. °C. |
|---|---|---|---|---|---|
| 94x | 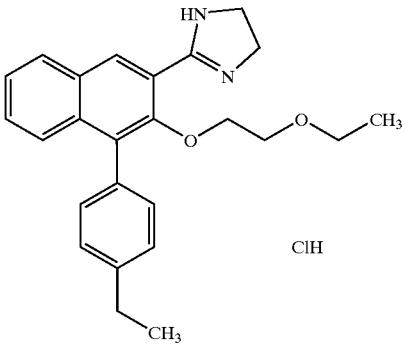 | 2-[3-2-Ethoxyethoxy)-4-(4-ethylphenyl)naphthalen-2-yl]-4,5-dihydro-1H-imidazole Hydrochloride | 24 | 388 | 215 |
| 94y | 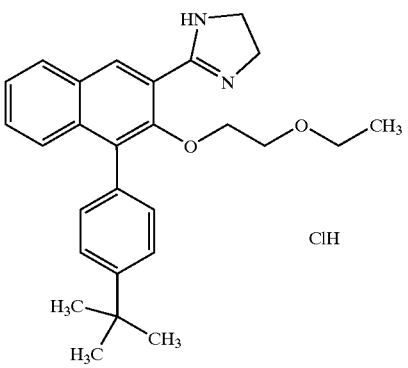 | 2-[4-(4-tert.Butylphenyl)-3-(2-ethoxyethoxy)naphthalen-2-yl]-4,5-dihydro-1H-imidazole Hydrochloride | 28 | 416 | 248 |
| 94z | 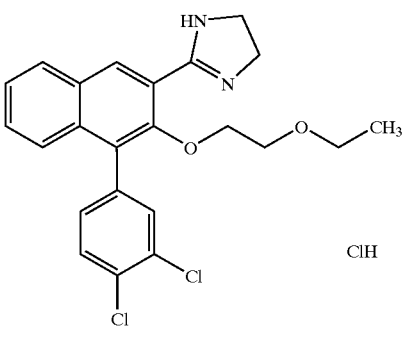 | 2-[4-(3,4-Dichlorophenyl)-3-(2-ethoxyethoxy)naphthalen-2-yl]-4,5-dihydro-1H-imidazole Hydrochloride | 9 | 428 | 192 |
| 94aa | 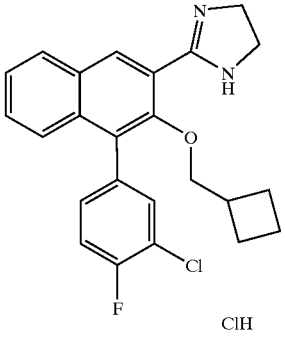 | 2-[4-(3-Chloro-4-fluorophenyl)-3-(cyclobutylmethoxy)naphthalen-2-yl)-4,5-dihydro-1H-imidazole Hydrochloride | 4 | 409 | 173 |

TABLE VI-continued

| Structure and E.g. # | Name | Yield % | MS (M+) | M.P. °C. |
|---|---|---|---|---|
| 94ab | 2-[4-(4-Chlorophenyl)-3-propoxynaphthalen-2-yl]-4,5-dihydro-1H-imidazole Hydrochloride | 23 | 365 | amorphous |
| 94ac | 2-[4-(3,4-Dichlorophenyl)-3-(cyclobutylmethoxy)naphthalene-2-yl]-4,5-dihydro-1H-imidazole Hydrochloride | 10 | 425 | 192 |
| 94ad | 2-[4-(4-Biphenyl)-3-(2-methoxyethoxy)naphthalen-2-yl]-4,5-dihydro-1H-imidazole Hydrochloride | 15 | 423 | 214 |
| 94ae | 2-[4-(4-Ethylphenyl-3-(2-methoxyethoxy)naphthalen-2-yl]-4,5-dihydro-1H-imidazole Hydrochloride | 24 | 375 | 165 |

TABLE VI-continued

| Structure and E.g. # | Name | Yield % | MS (M+) | M.P. °C. |
|---|---|---|---|---|
| 94af | 2-[3-(2-Methoxyethoxy)-4-(3,4-methylendioxophenyl)-naphthalen-2-yl]-4,5-dihydro-1H-imidazole Hydrochloride | 12 | 390 | 168 |
| 94ag | 2-[4-(4-tert.Butylphenyl)-3-(2-methoxyethoxy)naphthalen-2-yl]-4,5-dihydro-1H-imidazole Hydrochloride | 25 | 403 | 179 |
| 94ah | 2-[4-(3,4-Dimethoxyphenyl)-3-(2-methoxyethoxy)naphthalen-2-yl]-4,5-dihydro-1H-imidazole Hydrochloride | 30 | 407 | 225 |
| 94ai | 2-[4-(2,4-Dichlorophenyl)-3-propoxynaphthalen-2-yl]-4,5-dihydro-1H-imidazole Hydrochloride | 38 | 399 | 181 |

EXAMPLE 95

7-Optionally substituted aryl- and heteroaryl- and 7-bromo-2-(4,5-dihydro-1H-imidazolin-2-yl)-3-substituted napthalenes The compounds of Table VII, Examples 95a to 95at, are prepared by methods known in the art, or by the procedures as described herein, for example in Scheme V.

TABLE VII

| Structure and E.g. # | Name | Yield % | MS (M+) | M.P. °C. |
|---|---|---|---|---|
| 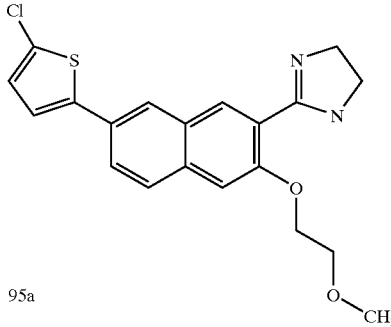 95a | 2-[7-(5-Chlorothien-2-yl)-3-(2-methoxyethoxy)naphthalen-2-yl]-4,5-1H-imidazole | 41 | 386 | amorphous |
| 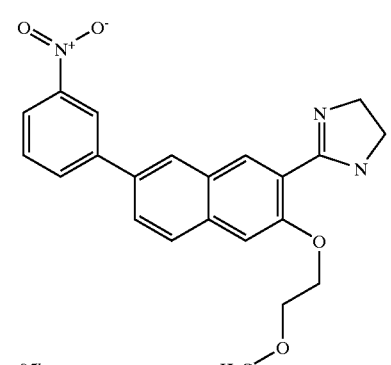 95b | 2-[3-(2-Methoxyethoxy)-7-(3-nitrophenyl)naphthalen-2-yl]-4,5-1H-imidazole | 22 | 391 | amorphous |
| 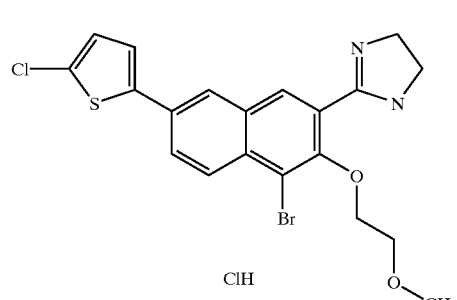 95c | 2-[4-Bromo-7-(5-chlorothien-2-yl)-3-(2-methoxyethoxy)naphthalen-2-yl]-4,5-1H-imidazole Hydrochloride | 33 | 466 | amorphous |
| 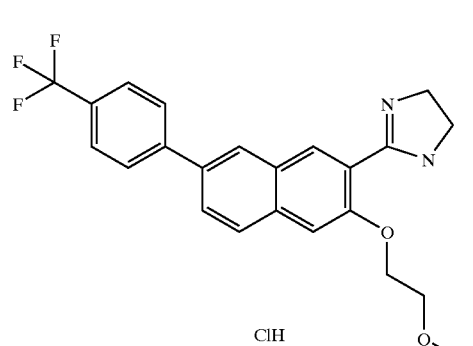 95d | 2-[3-(2-Methoxyethoxy)-7-(4-trifluoromethylphenyl)-naphthalen-2-yl]-4,5-dihydro-1H-imidazole Hydrochloride | 34 | 414 | amorphous |

TABLE VII-continued

| Structure and E.g. # | Name | Yield % | MS (M+) | M.P. ° C. |
|---|---|---|---|---|
| 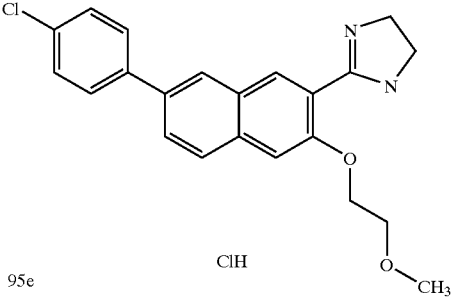 95e | 2-[3-(2-Methoxyethoxy)-7-(4-chlorophenyl)naphthalen-2-yl]-4,5-dihydro-1H-imidazole Hydrochloride | 27 | 381 | amorphous |
| 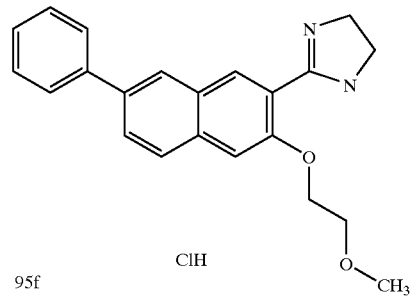 95f | 2-[3-(2-Methoxyethoxy)-7-phenylnaphthalen-2-yl]-4,5-dihydro-1H-imidazole Hydrochloride | 36 | 346 | amorphous |
| 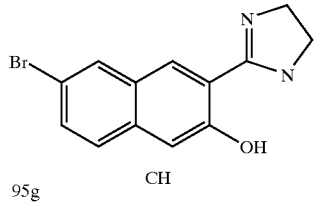 95g | 2-(7-Bromo-3-hydroxynaphthalen-2-yl)-4,5-1H-imidazole Hydrochloride | 60 | 291 | amorphous |
| 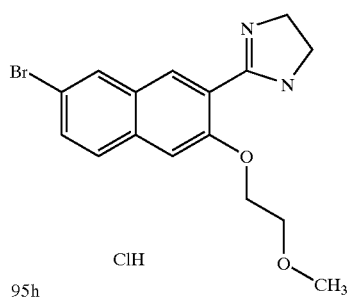 95h | 2-(7-Bromo-3-butoxynaphthalen-2-yl)-4,5-1H-imidazole Hydrochloride | 3 | 347 | amorphous |
| 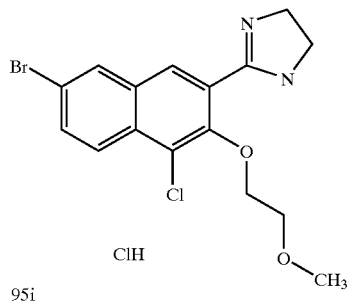 95i | 2-[7-Bromo-4-chloro-3-(2-methoxyethoxy)naphthalen-2-yl]-4,5-dihydro-1H-imidazole Hydrochloride | 5 | 384 | amorphous |

TABLE VII-continued

| Structure and E.g. # | Name | Yield % | MS (M+) | M.P. ° C. |
|---|---|---|---|---|
| 95j | 2-[3-Butoxy-7-(4-methylphenyl)naphthalen-2-yl]-4,5-1H-imidazole Hydrochloride | 41 | 359 | amorphous |
| 95k | 2-[3-Butoxy-7-(3-nitrophenyl)naphthalen-2-yl]-4,5-1H-imidazole Hydrochloride | 50 | 390 | amorphous |
| 95l | 2-[4-Chloro-7-(5-chlorothien-2-yl)-3-(2-methoxyethoxy)naphthalen-2-yl]-4,5-1H-imidazole Hydrochloride | 64 | 421 | amorphous |
| 95m | 2-[4-Chloro-3-(2-methoxyethoxy)-7-(4-methylphenyl)naphthalen-2-yl]-4,5-1H-imidazole Hydrochloride | 62 | 395 | amorphous |

TABLE VII-continued

| Structure and E.g. # | Name | Yield % | MS (M+) | M.P. ° C. |
|---|---|---|---|---|
| 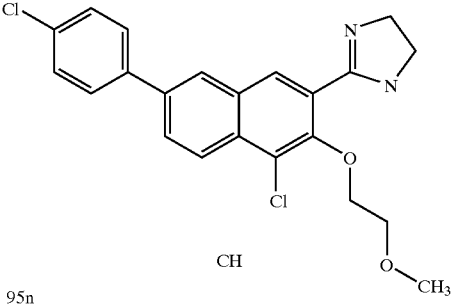 95n | 2-[4-Chloro-7-(4-chlorophenyl)-3-(2-methoxyethoxy)naphthalen-2-yl]-4,5-1H-imidazole Hydrochloride | 43 | 415 | 200 |
| 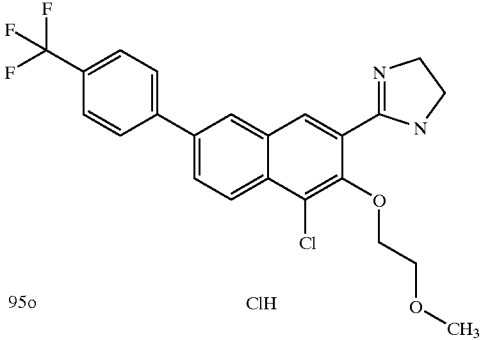 95o | 2-[4-Chloro-3-(2-methoxyethoxy)-7-(4-trifluoromethylphenyl)-naphthalen-2-yl]-4,5-1H-imidazole Hydrochloride | 40 | 449 | 216 |
| 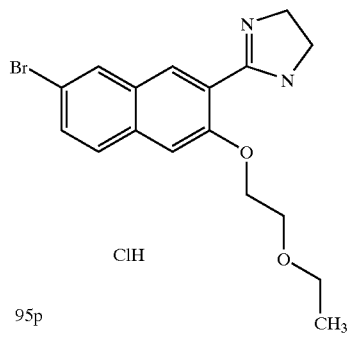 95p | 2-[7-Bromo-3-(2-ethoxyethoxy)naphthalen-2-yl]-4,5-1H-imidazole Hydrochloride | 32 | 363 | 256 |
| 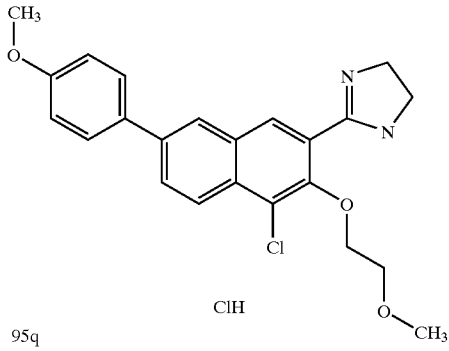 95q | 2-[4-Chloro-3-(2-methoxyethoxy)-7-(4-methoxyphenyl)naphthalen-2-yl]-4,5-1H-imidazole Hydrochloride | 60 | 411 | 206 |

TABLE VII-continued

| Structure and E.g. # | Name | Yield % | MS (M+) | M.P. ° C. |
|---|---|---|---|---|
| 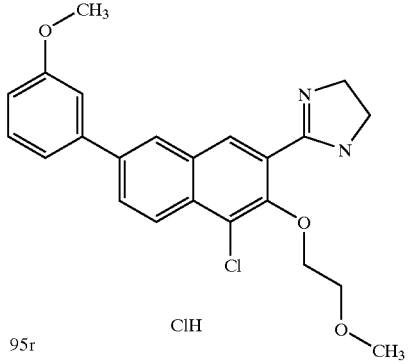 95r | 2-[3-(2-Methoxyethoxy)-7-(3-methoxyphenyl)naph-thalen-2-yl]-4,5-1H-imidazole Hydrochloride | 44 | 377 | 230 |
| 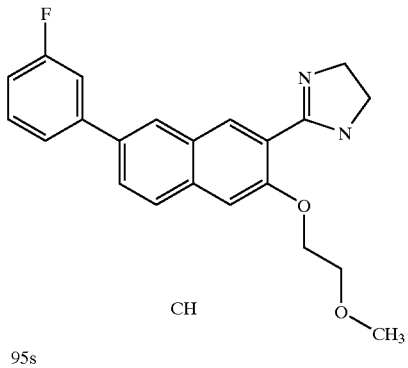 95s | 2-[7-(3-Fluorophenyl)-3-(2-methoxyethoxy)naph-thalen-2-yl]-4,5-1H-imidazole Hydrochloride | 37 | 364 | amorphous |
| 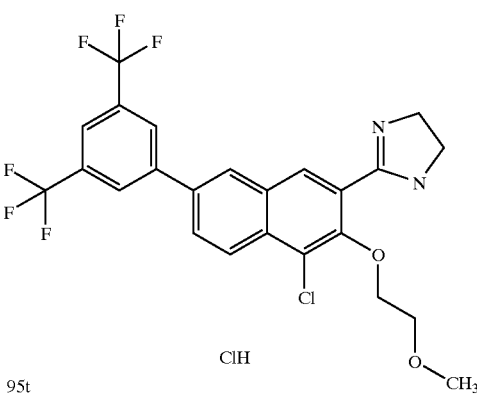 95t | 2-[3-(2-Methoxyethoxy)-7-(3,5-bis(trifluoromethyl)-phenyl)naphthalen-2-yl]-4,5-1H-imidazole Hydrochloride | 25 | 482 | 264 |
| 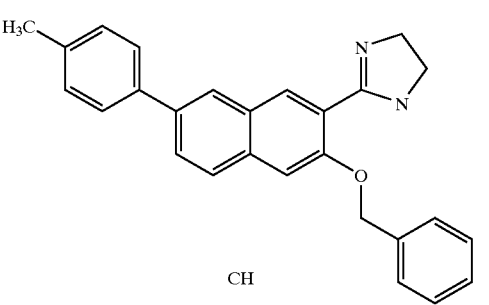 95u | 2-[7-(4-Methylphenyl)-3-(phenylmethoxy)naph-thalen-2-yl]-4,5-1H-imidazole Hydrochloride | 35 | 393 | 224 |

TABLE VII-continued

| Structure and E.g. # | Name | Yield % | MS (M+) | M.P. ° C. |
|---|---|---|---|---|
| 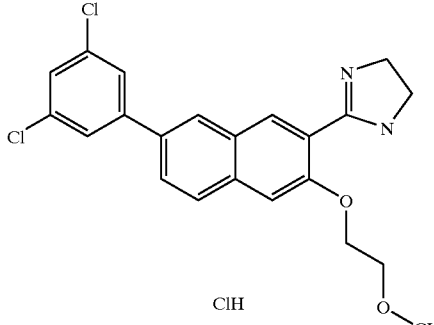 95v | 2-[7-(3,5-Dichlorophenyl)-3-(2-methoxyethoxy)naphthalen-2-yl]-4,5-1H-imidazole Hydrochloride | 28 | 415 | 240 |
| 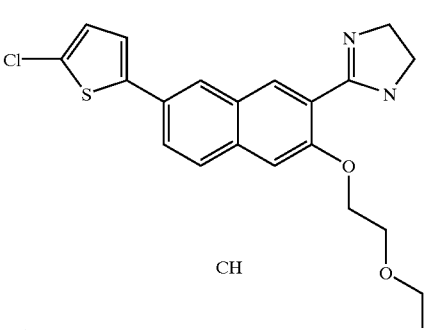 95w | 2-[7-(5-Chlorothien-2-yl)-3-(2-ethoxyethoxy)-naphthalen-2-yl]-4,5-1H-imidazole Hydrochloride | 36 | 401 | 206 |
| 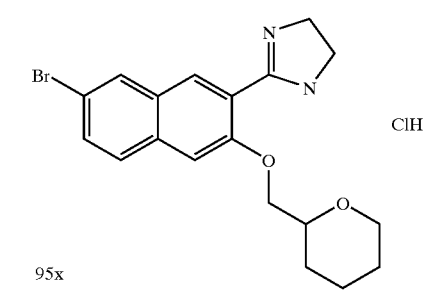 95x | 2-]7-Bromo-3-(3,4,5,6-tetrahydropyran-2-yl-methoxy)naphthalen-2-yl]-4,5-dihydro-1H-imidazole Hydrochloride | 50 | 389 | 284 |
| 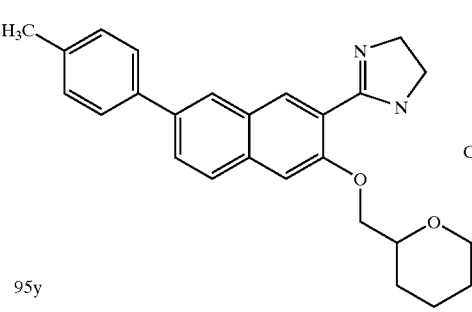 95y | 2-[7-(4-Methylphenyl)-3-(3,4,5,6-tetrahydropyran-2-yl-methoxy)naphthalen-2-yl]-4,5-dihydro-1H-imidazole Hydrochloride | 26 | 401 | 290 |

TABLE VII-continued
| Structure and E.g. # | Name | Yield % | MS (M+) | M.P. °C. |
|---|---|---|---|---|
| 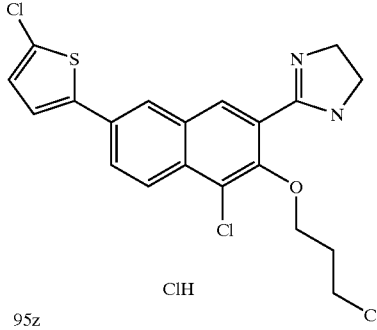<br>95z | 2-[3-Butoxy-7-(5-chlorothien-2-yl)naphthalen-2-yl]-4,5-1H-imidazole Hydrochloride | 50 | 385 | 240 |
| 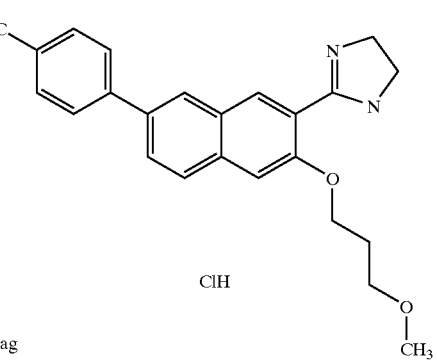<br>95ag | 2-[3-(3-Methoxypropoxy)-7-(4-methylphenyl)naphthalen-2-yl]-4,5-1H-imidazole Hydrochloride | 30 | 375 | 238 |
| 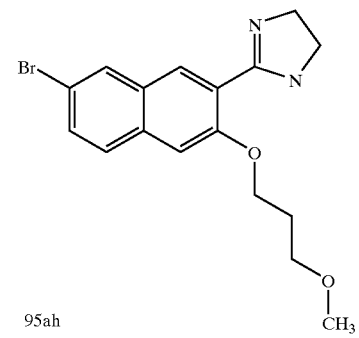<br>95ah | 2-[7-Bromo-3-(3-methoxypropoxy)naphthalen-2-yl]-4,5-1H-imidazole | 37 | 327 | 228 |
| 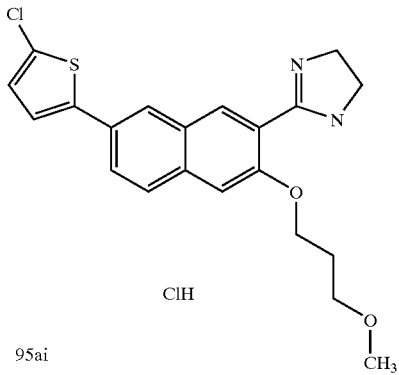<br>95ai | 2-[7-(5-Chlorothien-2-yl)-3-(3-methoxypropoxy)naphthalen-2-yl]-4,5-dihydro-1H-imidazole Hydrochloride | 38 | 401 | 210 |

TABLE VII-continued

| Structure and E.g. # | Name | Yield % | MS (M+) | M.P. °C. |
|---|---|---|---|---|
| 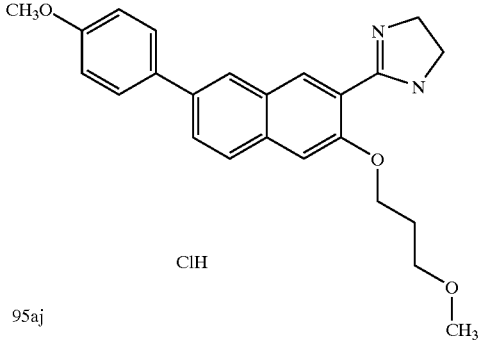 95aj | 2-[7-(4-Methoxyphenyl)-3-(3-methoxypropoxy)naphthalen-2-yl]-4,5-dihydro-1H-imidazole Hydrochloride | 31 | 391 | 226 |
| 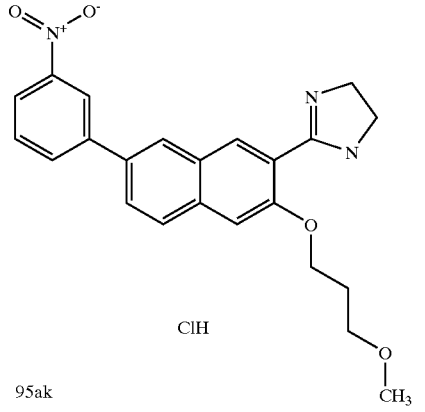 95ak | 2-[3-(3-Methoxypropoxy)-7-(3-nitrophenyl)naphthalen-2-yl]-4,5-dihydro-1H-imidazole Hydrochloride | 41 | 406 | 248 |
| 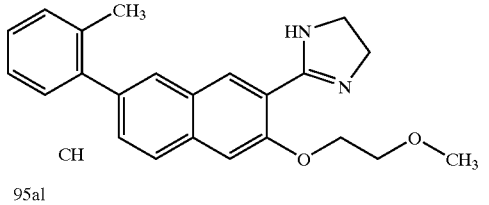 95al | 2-[3-(2-Methoxyethoxy)-7-(2-methoxyphenyl)naphthalen-2-yl]-4,5-dihydro-1H-imidazole Hydrochloride | 27 | 361 | 276 |
| 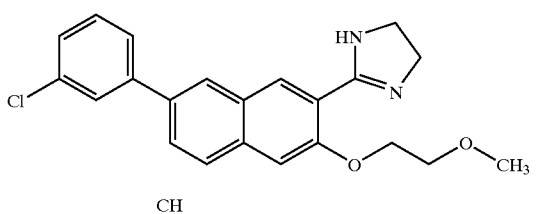 95am | 2-[7-(3-Chlorophenyl)-3-(2-methoxyethoxy)naphthalen-2-yl]-4,5-dihydro-1H-imidazole Hydrochloride | 32 | 381 | 264 |
| 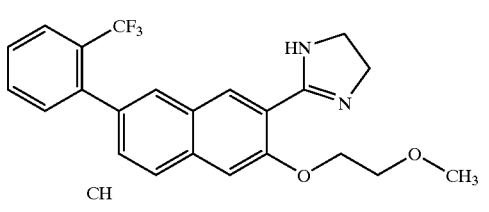 95an | 2-[3-(2-Methoxyethoxy-7-(2-trifluoromethylphenyl)-naphthalen-2-yl]-4,5-dihydro-1H-imidazole Hydrochloride | 28 | 414 | 271 |

TABLE VII-continued

| Structure and E.g. # | Name | Yield % | MS (M+) | M.P. °C. |
|---|---|---|---|---|
| 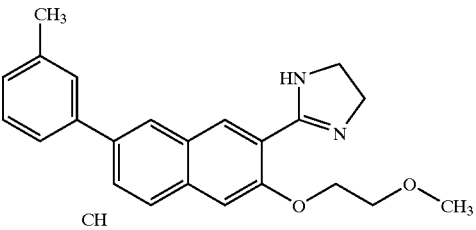 95ao | 2-[3-(2-Methoxyethoxy)-7-(3-methylphenyl)naphthalen-2-yl]-4,5-dihydro-1H-imidazole Hydrochloride | 32 | 361 | 260 |
| 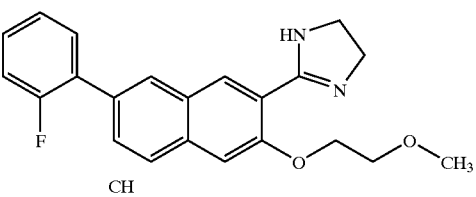 95ap | 2-[7-(2-Fluorophenyl)-3-(2-methoxyethoxy)naphthalen-2-yl]-4,5-dihydro-1H-imidazole Hydrochloride | 34 | 364 | 272 |
| 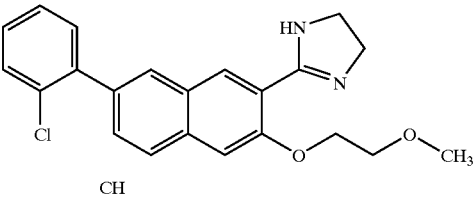 95aq | 2-[7-(2-Chlorophenyl)-3-(2-methoxyethoxy)naphthalen-2-yl]-4,5-dihydro-1H-imidazole Hydrochloride | 32 | 381 | 281 |
| 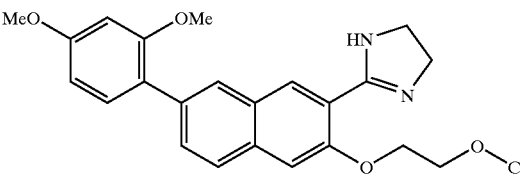 95ar | 2-[7-(2,4-Dimethoxyphenyl-3-(2-methoxyethoxy)naphthalen/-2-yl]-4,5-dihydro-1H-imidazole Hydrochloride | 27 | 407 | 239 |
| 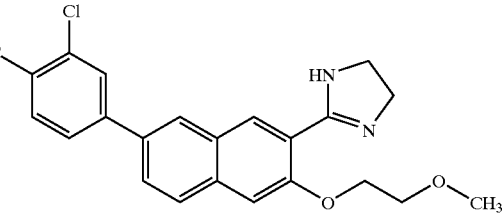 95as | 2-[7-(3-Chloro-4-fluorophenyl)-3-(2-methoxyethoxy)naphthalen-2-yl]-4,5-dihydro-1H-imidazole Hydrochloride | 29 | 399 | amorphous |

TABLE VII-continued

| Structure and E.g. # | Name | Yield % | MS (M+) | M.P. °C. |
|---|---|---|---|---|
| 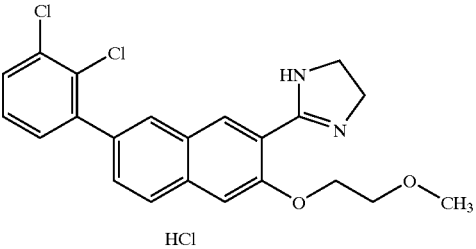<br>95at | 2-[7-(2,3-Dichlorophenyl-3-(2-methoxyethoxy)naphthalen-2-yl]-4,5-dihydro-1H-imidazole Hydrochloride | 28 | 415 | 279 |

EXAMPLE 96

6-Chloro-3-(4,5-dihydro-1H-imidazol-2-yl)-3-methylquinoline (X=Cl, R=CH₃)

The variables "X" and "R" refer to the structure illustrated herein above in Example 5.

Step 1: Ethyl 3-(4-Chlorophenylamino)but-2-enoate

A solution of 70 g (0.54 mol) of 4-chloroaniline, 70 ml (0.54 mol) of ethyl acetoacetate, and 0.6 ml acetic acid in 400 ml toluene was heated in a Dean-Stark apparatus for 19 at 130° C. The mixture was evaporated, and the remaining crystalline precipitate stirred with diisopropylether and filtered. The filtrate was concentrated and the residue purified via column chromatography on silica gel with dichloromethane/hexane 4:1.

yield: 62 g (48%)

Step 2: Ethyl 6-Chloro-2-methylquinoline-3carboxylate

To a solution of 6.2 g (83 mmol) DMF in 50 ml of 1,2 dichloroethane was carefully added 19.1 g (126 mmol) of phosphoryl chloride. After stirring for 10 min at ambient temperature a solution of 20 g (83 mol) of ethyl 3-(4-chlorophenylamino)but-2-enoate in 50 ml of 1,2 dichloroethane was added slowly, while the mixture turned dark in an exothermic reaction. Stirring at ambient temperature was continued for another hour followed by heating with reflux for 6 h. The mixture was poured on to crushed ice, washed twice with water, dried over sodium sulfate, and concentrated under reduced pressure. The title ester was obtained from the residue via flash chromatography on silica gel with dichloromethane/hexane 4:1.

yield: 15 g (72%)

Step 3: 2-Aminoethyl 6-Chloro-2-methylquinoline-3-carbamide

A mixture of 10 g (38 mMol) of the ester from the previous step was heated in 45 ml of neat ethylene diamine for 16 h at 95° C. The excess of amine was removed in a vacuo and the residue was purified via flash chromatography on silica gel with dichloromethane followed by dichloromethane/ethanolic ammonia 7:3.

yield: 7.2 g (72%)

Step 4: 6-Chloro-3-(4,5-dihydro-1H-imidazol-2-yl)-3-methylquinoline

To a solution of 3 g (114 mmol) of the 2-aminoethylamide in 75 ml of dichloromethane under argon 15.2 g of diethylaminomethyl polystyrene and 6.31 ml of TMS iodide were added. After stirring for 170 h at ambient temperature the resin was removed by filtration and repeatedly rinsed with dichloromethane and ethanol (3×30 ml each). The filtrate was concentrated under reduced pressure and the residue purified via preparative BPLC on RP-18 silica gel with an acetonitrile/water gradient.

yield: 1 g (36%); brown crystalline solid

The following two quinolines were prepared analogously using substantially similar procedures, starting from ethyl 2-oxobutyrate and 3-chloroaniline. The intermediate mixture of ethyl 5-chloro-3-methylquinoline-2-carboxylate and the isomeric ethyl 7-chloro-3-methylquinoline-2-carboxylate was separated by preparative HPLC, and both esters were converted to the corresponding imidazolines as described above: In these following examples, the variable "X" refers to the following illustrated structure:

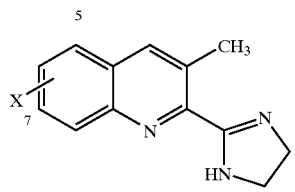

EXAMPLE 96a

5-Chloro-2-(4,5-dihydro-1H-imidazol-2-yl)-3-methylquinoline (X=5-Cl)

colorless crystals

EXAMPLE 96b

7-Chloro-2-(4,5-dihydro-1H-imidazol-2-yl)-3-methylquinoline (X=7-Cl)

beige crystalline solid, m.p. 139–141° C.

EXAMPLE 97

2,5-Bistrifluoromethyl-3-(4,5-dihydroimidazol-2-yl)-1H-indole

Step 1: 2–4-Iodo-4-trifluoromethyl-aniline

The intermediate was prepared according to a literature procedure (Tetrahedron 50 (1994), 7343).

Step 2: 2,2,2-Trifluoro-N-(2-iodo-4-trifluoromethylphenyl)acetamide

The compound was prepared from the aniline of the previous step with trifluoro acetanhydride in tert.-butylmethylether by a standard procedure in quantitative yield.

Step 3: Ethyl 2,5-Bistrifluoromethyl-1H-indole-3-carboxylate

The indole was prepared from the trifluoroacetamide according to a literature method (J. Chem. Soc., Perkin Trans 1, 1997, 2056).

Step 4: 2,5-Bistrifluoromethyl-1H-indole-3-carboxylic Acid

The indole-3-carboxylate was saponified with 5% aqueous potassium hydroxide solution to give the carboxylic acid in 25% yield.

Step 5: 2,5-Bistrifluoromethyl-1H-indole-3-carbonyl chloride

A mixture of 500 mg (1.68 mmol) of the indolecarboxylic acid from Step 4 and 20 ml of thionyl chloride was heated for 3 at 70° C. The excess of thionyl chloride was removed under reduced pressure and the remaining crude acid chloride was dissolved in 30 ml of dry dichloromethane. This solution was used in the next step.

Step 6: 2-Aminoethyl 2,5-Bistrifluoromethyl-1H-indole-3-carbamide

A solution of 5 g of ethylenediamine in 30 ml of dry dichloromethane was cooled to −20° C. followed by addition of the 2,5-bistrifluoromethyl-1H-indole-3-carbonyl chloride solution. After stirring for 1 h the mixture was brought to ambient temperature and all volatiles were removed in a vacuo. The residue was redissolved in a small amount of dichloromethane, coated on silica gel, and the title amide was purified by flash chromatography with dichloromethane/ethanol gradient 9:1 to 1:1.

yield: 240 mg (42%)

Step 7: 2,5-Bistrifluoromethyl-3-(4,5-dihydroimidazol-2-yl)-1H-indole

A mixture of 120 mg of the amide and 1.5 ml of neat HMDS containing 1% of TMS chloride was stirred for 16 h at 100° C. After quenching with ethanol all volatiles were removed in vacuo. The residue was redissolved in a small amount of dichloromethane, coated on silica gel, and purified by flash chromatography with dichloromethane followed by dichloromethane/ethanolic ammonia 95:5.

yield: 65 mg (57%); pale beige crystalline solid

The pharmacological activity of compounds of the present invention may be determined by methods well known in the art and by the assays disclosed herein.

Assays

BTC6,F7 Insulinoma Cell Screening Models

BTC6,F7 are cultured in DMEM 4.5 g/l glucose with the following supplements: 15% (v/v) equine serum; 2.5% (v/v) FCS; and 50 U/ml Penicillin/50 μg/ml Streptomycin.

A) Adherent $BTC_6F7$ Cells $BTC_6F7$ are seeded after trypsinization to 30.000 cells/well in a 96 well multiplate. The cells grow to 50% confluence and at day 2 or 3 after seeding, the insulin secretion experiments were performed as follows:

Discard the supernatant of the 96 well plates after the cells have been seeded, wash 3 times with EBSS (Earl's balanced salt solution) (0 mM glucose)/0.1% BSA and incubate in the EBSS solution 30 min at 5% $CO_2$, 37° C.

The experiments with the compounds were run in the presence of 10 mM glucose and also in the absence of glucose in different concentrations. Incubation time is 1 our. The supernatante is filtered and the insulin amounts measured by radioimmunoassay using an antibody directed against rat insulin.

B) Dissociated $BTC_6F7$ Cells $BTC_6F7$ cells at 50% confluence were dislodged using enzyme free cell dissociation solution. Dislodged cells were dissociated by pressing the cell suspension through a needle (25 gauge). Cells were washed three times in EBSS (0 mM glucose)/0.1% BSA and insulin secretion experiments are performed as described above.

Dose response titrations on the agonists described revealed $EC_{50}$ values of <10 mM, preferably <1 mmol.

Rat Islet Assay

The number of islets of three rats is usually sufficient to test 8 compounds including standards.

Solutions 1. 100 ml EBSS (Earl's balanced salt solution): For example, as commercially available Cat. No. BSS-008-B (Specialty Media) without Glucose & Phenol Red, with 0.1% BSA, other comparable commercially available media are acceptable.

2. 100 ml EBSS/13SA buffer+130.8 mg D(+)-Glucose monohydrate (MW: 198.17) (=3.3 mM final concentration).

3. 100 ml EBSS/BSA buffer+661.8 mg D(+)-Glucose monohydrate (MW: 198.17) (=16.7 mM final concentration).

4. 100 ml EBSS (Earl's balanced salt solution). For example, as commercially available,Cat. No. BSS-008-B (Specialty Media) without Glucose & Phenol Red, with 0.1% BSA, with 0.6% DMSO; other comparable solutions may be used as well;

Dilution of Compounds

Each dilution of compound has to be double concentrated as it will be diluted 1+1 by EBSSA/SA+Glucose (either high Glucose, 16.7 mM final conc. or low Glucose, 3.3 mM final conc.) in a 24-well tissue culture plate (or other appropriate tissue culture receptacle, if desired).

A stock solution of the compound to be tested of 10 mM in DMSO is made, and the following solutions made for the compounds to be tested, and for standards.

| Tube No. | Concentration (μM) | final Concentration (μM) | Dilution (μl) |
|---|---|---|---|
| 1 | 200 | 100 | 40 μl of stock + 2000 μl EBSS/BSA |
| 2 | 60 | 30 | 900 μl of tube 1 + 2100 μl EBSS/BSA |
| 3 | 20 | 10 | 300 μl of tube 1 + 2700 μl EBSS/BSA/ 0.6 % DMSO |
| 4 | 6 | 3 | 300 μl of tube 2 + 2700 μl EBSS/BSA/ 0.6 % DMSO |
| 5 | 2 | 1 | 300 μl of tube 3 + 2700 μl EBSS/BSA/ 0.6% DMSO |
| 6 | 0.6 | 0.3 | 300 μl of tube 4 + 2700 μl EBSS/BSA/ 0.6% DMSO |

-continued

| Tube No. | Concentration ($\mu M$) | final Concentration ($\mu M$) | Dilution ($\mu l$) |
|---|---|---|---|
| 7 | 0.2 | 0.1 | 300 $\mu l$ of tube 5 + 2700 $\mu l$ EBSS/BSA/ 0.6% DMSO |
| 8 | 0.06 | 0.03 | 300 $\mu l$ of tube 6 + 2700 $\mu l$ EBSS/BSA/ 0.6% DMSO |

Culture dishes are prepared (untreated, 100×20 mm, one per two compounds) with 10 ml EBSS/BSA and 10 ml low glucose EBSS/BSA or similar preparative solution and place in an incubator at 37° C., 5% $CO_2$, for at least 15 min.

Preparation of Rat Islets in Culture Dishes

Approximately half of an islet is selected with a 100 $\mu l$ pipette and transfered to a prepared culture dishe with EBSS/BSA/low Glucose by using binoculars (magnification about 30×.

The dish is put back into the incubator (37° C., 5% $CO_2$) for preincubation (30 min)

If a 24 well plate is used for the assay, the dilutions are distributed (500 $\mu l$ each) as shown in the scheme below.

500 $\mu l$ of EBSS/BSA+0.6% DMSO (0=Control).

| 0 | 0 | 0.03 | 0.03 | 0.1 | 0.1 |
|---|---|---|---|---|---|
| 1 | 2 | 3 | 4 | 5 | 6 |
| 0.3 | 0.3 | 1 | 1 | 3 | 3 |
| 7 | 8 | 9 | 10 | 11 | 12 |
| 10 | 10 | 30 | 30 | 0 | 0 |
| 13 | 14 | 15 | 16 | 17 | 18 |
| 0.1 | 0.1 | 1 | 1 | 10 | 10 |
| 19 | 20 | 21 | 22 | 23 | 24 |

EBSS/BSA/high Glucose, 500 $\mu l$ is added to wells 1–16, and EBSS/BSA/low Glucose, 500 $\mu l$ is added to wells 17–24.

This scheme is repeated with the other compounds in tissue culture plates and the plates are placed into the incubator (37° C., 5% $CO_2$) for at least 15 min.

The culture dish with the second half of the islets is taken out of the incubator. The rest of the islet is picked up with a 100 $\mu l$ pipette and placed into the second of the prepared culture dishes with EBSS/BSA/low Glucose using binoculars, and placed back into the incubator (37° C., 5% $CO_2$) for preincubation (30 min).

Take out the tissue culture plates 1 and 2 and the first preincubated islets. Place 8 islets into each well by using a 10 $\mu l$ pipette and binoculars (general guideline-magnification about 40×), generally trying to select islets of similar size which are not digested. The plates are placed back in the incubator (37° C., 5% $CO_2$) for 90 min.

Remove the second of the overnight cultured culture dishes with islets from incubator. Approximately half of the islets are placed into the 3rd of the prepared culture dishes with EBSS/BSA/low Glucose with a 100 $\mu l$ pipette and using binoculars (general guideline-magnification about 30×), then placed back into the incubator (37° C., 5% $CO_2$) for preincubation (30 min).

The 24-well tissue culture plates 3 and 4 and the second preincubated islets culture dish are removed from the incubator and 8 islets placed into each well by using a 10 $\mu l$ pipette and binoculars (magnification about 40×), again selecting islets of similar size which are not digested. Put the plates back to the incubator (37° C., 5% $CO_2$) for 90 min.

Take the culture dish with the second half of the islets out of the incubator. with a 100 $\mu l$ pipette into the 4th of the prepared culture dishes with EBSS/BSA/low Glucose by using binoculars (magnification about 30×) and put them back into the incubator (37° C., 5% $CO_2$) for preincubation (30 min)

Take out the 24-well tissue culture plates 5 and 6 and the 3rd preincubated islets culture dish. Place 8 islets into each well with a 10 $\mu l$ pipette by using binoculars (magnification about 40×). Put the plates back into the incubator (37° C., 5% $CO_2$) for 90 min.

Take out the 24-well tissue culture plates 7 and 8 and the last preincubated islets culture dish. Place 8 islets into each well with a 10 $\mu l$ pipette by using binoculars (magnification about 40×). Put the plates back to the incubator (37° C., 5% $CO_2$) for 90 min.

When 90 minutes of incubation are over, transfer approximately 300 $\mu l$ of each well into one well of the 96 well filter plate and by using a vacuum pump filter it into a 96 well Microplate. 4 of the 24-well tissue culture plates cover one filterplate and 96-well-Microplate.

The insulin secreted by the islets is measured in a RIA after dilution (1:5).

Intravenous Glucose Tolerance Test

This test is used to examine in vivo efficacy of compounds of the present invention on insulin secretion and blood glucose at hyperglycemia.

The intravenous glucose tolerance test (IVGTT) is performed in overnight fasted anesthetized male wistar rats weighing 280–350 g. Under pentobarbitone anesthesia (50 mg/kg ip) polyethylene catheters are placed in the left jugular vein and in the left common carotid artery. Glucose (10% solution) is administered intravenously at a dose of 0.5 g/kg, followed directly by an iv injection of the compound to be tested.

Blood samples are drawn before and 3, 6, 10, 15, 30 and 45 min after glucose administration, centrifuged and the obtained serum is stored at −20° C. for analytics. Test compounds are examined along with a reference (positive control) and a vehicle control with n=8 animals per group. Glucose is determined by the hexokinase method, and insulin via radioimmunoassay (RIA) from serum.

In order to examine the effects of test compounds on insulin and blood glucose at euglycemia in vivo, the protocol of the IVGTT as described above is used except for the administration of intravenous glucose.

The compounds of Formula I are preferably formulated prior to administration. Therefore, yet another embodiment of the present invention is a pharmaceutical formulation comprising a compound of Formula I and one or more pharmaceutically acceptable carriers, diluents or excipients.

The present pharmaceutical formulations are prepared by known procedures using well-known and readily available ingredients. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient.

The compositions are preferably formulated in a unit dosage form, each dosage containing from about 0.1 to about 500 mg, more usually about 0.5 to about 200 mg, of the active ingredient. However, it will be understood that the therapeutic dosage administered will be determined by the physician in the light of the relevant circumstances including the condition to be treated, the choice of compound to be administered and the chosen route of administration, and therefore the above dosage ranges are not intended to limit the scope of the invention in any way. The compounds can be administered by a variety of routes including the oral, rectal, transdermal, subcutaneous, topical, intravenous, intramuscular or intranasal routes. For all indications, a typical daily dose will contain from about 0.05 mg/kg to about 20 mg/kg of the active compound of this invention. Preferred daily doses will be about 0.1 to about 10 mg/kg, ideally about 0.1 to about 5 mg/kg. However, for topical administration a typical dosage is about 1 to about 500 mg compound per cm² of an affected tissue. Preferably, the applied amount of compound will range from about 30 to about 300 mg/cm², more preferably, from about 50 to about 200 mg/cm², and, most preferably, from about 60 to about 100 mg/cm².

The following formulation examples are illustrative only and are not intended to limit the scope of the invention in any way.

Formulation 1
Hard gelatin capsules are prepared using the following ingredients:

| | Quantity (mg/capsule) |
|---|---|
| Active ingredient | 25 |
| starch, dried | 425 |
| magnesium stearate | 10 |
| Total | 460 mg |

The above ingredients are mixed and filled into hard gelatin capsules in 460 mg quantities.

Formulation 2
Tablets each containing 10 mg of active ingredient are made up as follows:

| | |
|---|---|
| Active ingredient | 10 mg |
| Starch | 160 mg |

-continued

Formulation 2
Tablets each containing 10 mg of active ingredient are made up as follows:

| | |
|---|---|
| Microcrystalline cellulose | 100 mg |
| Polyvinylpyrrolidone (as 10% solution in water) | 13 mg |
| Sodium carboxymethyl starch | 14 mg |
| Magnesium stearate | 3 mg |
| Total | 300 mg |

The active ingredient, starch and cellulose are mixed thoroughly. The solution of polyvinylpyrrolidone is mixed with the resultant powders and passed through a sieve. The granules so produced are dried and re-passed through a sieve. The sodium carboxymethyl starch and magnesium stearate are then added to the granules which, after mixing, are compressed on a tablet machine to yield tablets each weighing 300 mg.

The principles, preferred embodiments and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention.

We claim:

1. A compound of Formula (I):

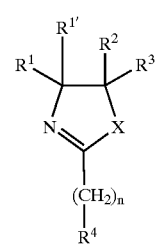

(I)

wherein

X is —O—, —S—, or —NR⁵—;

R⁵ is hydrogen, $C_{1-8}$ alkyl, or an amino protecting group;

$R^1$, $R^{1'}$, $R^2$, and $R^3$ are independently hydrogen or $C_{1-8}$ alkyl;

$R^1$ and $R^2$ optionally together form a bond and $R^{1'}$ and $R^3$ are independently hydrogen or $C_{1-8}$ alkyl;

$R^1$ and $R^2$ optionally combine together with the carbon atoms to which they are attached form a $C_{3-7}$ carbocyclic ring and $R^{1'}$ and $R^3$ are independently hydrogen or $C_{1-8}$ alkyl;

$R^1$ and $R^{1'}$ together with the carbon atom to which they are attached optionally combine to form a $C_{3-7}$ spirocarbocyclic ring and $R^2$ and $R^3$ are independently hydrogen or $C_{1-8}$ alkyl;

$R^2$ and $R^3$ together with the carbon atom to which they are attached optionally combine to form a $C_{3-7}$ spirocarbocyclic and $R^1$ and $R^{1'}$ are independently hydrogen or $C_{1-8}$ alkyl;

n is 0, 1, or 2;

m is 0, 1 or 2;

m' is 0, 1, or 2;

q' is 0,1,2,3,4, or 5;

$R^4$ is

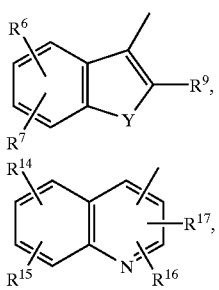 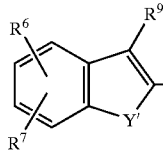, or

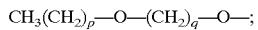

Y is —O—, —S—, or —NR$^8$—;
Y' is —O— or —S—;
$R^6$ and $R^7$ are independently hydrogen, $C_{1-8}$ alkyl, $C_{3-7}$ cycloalkyl, $C_{1-8}$ alkoxy, $C_{1-8}$ alkylthio, halo $C_{1-8}$ alkylthio, $C_{1-8}$ alkylsulfinyl, $C_{1-8}$ alkylsulfonyl, $C_{3-7}$ cycloalkoxy, aryl-$C_{1-8}$ alkoxy, halo, halo-$C_{1-8}$ alkyl, halo-$C_{1-8}$ alkoxy, nitro, —NR$^{10}$R$^{11}$, —CONR$^{10}$R$^{11}$, aryl $C_{1-8}$ alkyl, optionally substituted heterocyclyl, optionally substituted phenyl, optionally substituted naphthyl, optionally halo substituted acylamino, cyano, hydroxy, COR$^{12}$, halo $C_{1-8}$ alkylsulfinyl, or halo $C_{1-8}$ alkylsulfonyl, or alkoxyalkyl of the formula $$CH_3(CH_2)_p—O—(CH_2)_q—O—;$$

where
p is 0, 1, 2, 3, or 4; and
q is 1, 2, 3, 4, or 5;
$R^{12}$ is $C_{1-8}$ alkyl or optionally substituted phenyl;
$R^8$ is hydrogen, $C_{1-8}$ alkyl, halo-$C_{1-8}$ alkyl, optionally substituted phenyl, optionally substituted heterocyclyl, COO $C_{1-8}$ alkyl, optionally substituted COaryl, COC$_{1-8}$ alkyl, SO$_2$C$_{1-8}$ alkyl, optionally substituted SO$_2$ aryl, optionally substituted phenyl-$C_{1-8}$ alkyl, $CH_3(CH_2)_p$—O —$(CH_2)_q$—O—;
$R^9$ is hydrogen, halo, $C_{1-8}$ alkyl, halo $C_{1-8}$ alkyl, $C_{1-8}$ alkylthio, halo $C_{1-8}$ alkylthio, $C_{3-7}$ cycloalkylthio, optionally substituted arylthio or heteroarylthio, $C_{1-8}$ alkoxy, $C_{3-7}$ cycloalkoxy, optionally substituted aryloxy, optionally substituted heteroaryloxy, or optionally substituted aryl or heteroaryl, $C_{3-7}$ cycloalkyl, halo $C_{3-7}$ cycloalkyl, $C_{3-7}$ cycloalkenyl, cyano, COOR$^{10}$,CONR$^{10}$R$^{11}$ or NR$^{10}$R$^{11}$, $C_{2-6}$ alkenyl, optionally substituted heterocyclyl, optionally substituted aryl $C_{1-8}$ alkyl, optionally substituted heteroaryl $C_{1-8}$ alkyl in which the alkyl group can be substituted by hydroxy, or $C_{1-8}$ alkyl substituted by hydroxy,
$R^{10}$ and $R^{11}$ are independently hydrogen, $C_{1-8}$ alkyl, optionally substituted aryl $C_{1-8}$ alkyl, optionally substituted phenyl, or $R^{10}$ and $R^{11}$ together with the nitrogen atom to which they are attached may combine to form a ring with up to six carbon atoms which optionally may be substituted with up to two $C_{1-8}$ alkyl groups or one carbon atom may be replaced by oxygen or sulfur;
$R^{14}$ and $R^{16}$ are independently hydrogen, halo, $C_{1-8}$ alkyl, $C_{3-7}$ cycloalkyl, $C_{3-7}$ cycloalkoxy, $C_{3-7}$ cycloalkyl$C_{1-8}$ alkoxy, halo-$C_{1-8}$ alkyl, halo-$C_{1-8}$ alkoxy, $C_{1-8}$ alkoxy, carbo($C_{1-8}$)alkoxy, optionally substituted aryl, or optionally substituted heteroaryl;

$R^{15}$ and $R^{17}$ are independently hydrogen, halo, $C_{1-8}$ alkoxy, $C_{3-7}$-cycloalkyl, $C_{3-7}$ cycloalkyl$C_{1-8}$ alkoxy, $C_{1-8}$ alkyl, $C_{3-7}$ cycloalkoxy, hydroxy, halo $C_{1-8}$ alkoxy, carbo($C_{1-8}$)alkoxy, optionally substituted phenyl, optionally substituted phenyl-$C_{1-8}$ alkyl, optionally substituted phenyloxy, optionally substituted phenyl-$C_{1-8}$ alkoxy, (tetrahydropyran-2-yl)methoxy, $C_{1-8}$ alkyl-S(O)$_m$—, optionally substituted aryl-$C_{1-8}$ alkyl-S(O)$_m$—, $CH_3(CH_2)_p$—Z$^1$—$(CH_2)_q$—Z$^2$—, or Z$^3$—$(CH_2)_{q'}$—Z$^2$—;
$Z^1$ and $Z^2$ are independently a bond, O, S, SO, SO$_2$, sulphoximino, or NR$^{10}$; and
$Z^3$ is hydroxy, protected hydroxy, NR$^{10}$R$^{11}$, protected amino, SH or protected SH;

provided that when $R^4$ is

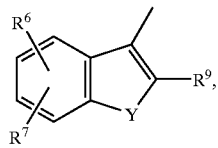

and Y is O or S, then $R^7$ is hydrogen, $R^6$ is hydrogen, halo, $C_{1-6}$ alkyl, or halo $C_{1-6}$ alkyl; and $R^9$ is $C_{1-6}$ alkyl or optionally substituted phenyl;

further provided that when $R^4$ is

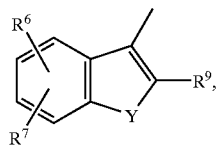

and Y is —NR$^8$— then $R^1$, $R^{1'}$, $R^2$ and $R^3$ are hydrogen or methyl;

X is —NH—;
n is 0, 1 or 2;
$R^4$ is

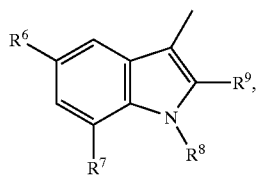

$R^6$ is chloro, fluoro, methyl, trifluoromethyl, or pentafluoroethyl;
$R^7$ is hydrogen or chloro, and most preferably hydrogen;
$R^8$ is hydrogen; and
$R^9$ is hydrogen, methyl, benzyl, 3-chlorobenzyl, 4-chlorophenyl, 3-chlorophenyl, 2-chlorophenyl, 3-methylphenyl, 4-chloro-3-methylphenyl, 4-methoxyphenyl, or 2-methoxyphenyl;

further provided that when R⁴ is

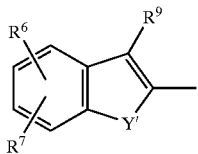

and Y' is O, then R⁷ is hydrogen, R⁹ is hydrogen, and R⁶ is hydrogen, halo, $C_{1-6}$ alkyl, or optionally substituted phenyl, naphthyl, or thienyl;
further provided that when R⁴ is

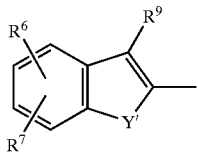

and Y' is S then R⁷ is hydrogen, R⁶ is hydrogen halo, $C_{1-6}$ alkyl, halo $C_{1-6}$ alkyl, $C_{1-6}$ alkoxy; and
R⁹ is hydrogen, halo, $C_{1-4}$ alkoxy, $C_{1-4}$ alkyl, optionally substituted phenyl, naphthyl, or thienyl, or an optionally substituted phenylmethyl, optionally substituted naphthylmethyl, optionally substituted thienylmethyl, or optionally substituted pyridylmethyl group in which the methyl group is substituted by hydroxy;
Further provided that when R⁴ is

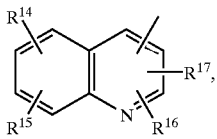

then R⁴ is

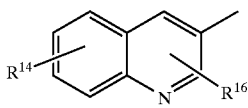

R¹⁴ is hydrogen, halo, C1–4 alkyl, C1–4 alkoxy, or halo C1–4 alkyl; and
R¹⁶ is C1–4 alkyl, halo C1–4 alkyl, or optionally substituted phenyl;
or a pharmaceutically acceptable salt or ester thereof.

2. A method of using compound of Formula (I):

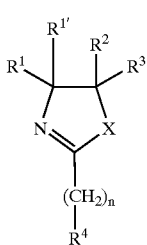

(I)

in which
X is —O—T—S—, or —NR⁵—;
R⁵ is hydrogen, $C_{1-8}$ alkyl, or an amino protecting group;

R¹, R¹', R², and R³ are independently hydrogen or $C_{1-8}$ alkyl;
R¹ and R² together form a bond and R¹' and R³ are independently hydrogen or $C_{1-8}$ alkyl;
R¹ and R² can combine together with the carbon atoms to which they are attached form a $C_{3-7}$ carbocyclic ring and R¹' and R³ are independently hydrogen or $C_{1-8}$ alkyl;
R¹ and R¹' together with the carbon atom to which they are attached combine to form a $C_{3-7}$ spirocarbocyclic ring and R² and R³ are independently hydrogen or $C_{1-8}$ alkyl;
R² and R³ together with the carbon atom to which they are attached combine to form a $C_{3-7}$ spirocarbocyclic and R¹ and R¹' are independently hydrogen or $C_{1-8}$ alkyl;
n is 0, 1, or 2;
R⁴ is

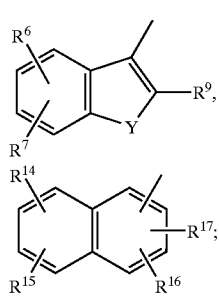 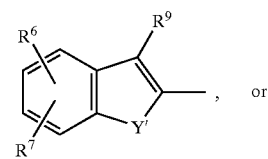, or

Y is —O—, —S—, or —NR⁸—;
Y' is —O— or —S—;
R⁶ and R⁷ are independently hydrogen, $C_{1-8}$ alkyl, $C_{3-7}$ cycloalkyl, $C_{1-8}$ alkoxy, $C_{1-8}$ alkylthio, halo $C_{1-8}$ alkylthio, $C_{1-8}$ alkylsulfinyl, $C_{1-8}$ alkylsulfonyl, $C_{3-7}$ cycloalkoxy, aryl-$C_{1-8}$ alkoxy, halo, halo-$C_{1-8}$ alkyl, halo-$C_{1-8}$ alkoxy, nitro, —NR¹⁰R¹¹, — CONR¹⁰R¹¹, aryl $C_{1-8}$ alkyl optionally substituted heterocyclyl, optionally substituted phenyl, optionally halo substituted acylamino, cyano, hydroxy, COR¹², halo $C_{1-8}$ alkylsulfinyl, or halo $C_{1-8}$ alkylsulfonyl, or alkoxyalkyl of the formula $CH_3(CH_2)_p—O—(CH_2)_q—O—$;

where
p is 0, 1, 2, 3, or 4; and
q is 1, 2, 3, 4, or 5;
R¹² is $C_{1-8}$ alkyl or optionally substituted phenyl;
R⁸ is hydrogen, $C_{1-8}$ alkyl, halo-$C_{1-8}$ alkyl, optionally substituted phenyl, optionally substituted heterocyclyl, COO $C_{1-8}$ alkyl, optionally substituted COaryl, COC$_{1-8}$ alkyl, SO₂C$_{1-8}$ alkyl, optionally substituted SO2 aryl, optionally substituted phenyl-$C_{1-8}$ alkyl, $CH_3(CH_2)_p—O—(CH_2)_q—O—$;
R⁹ is hydrogen, halo, $C_{1-8}$ alkyl, halo $C_{1-8}$ alkyl, $C_{1-8}$ alkylthio, halo $C_{1-8}$ alkylthio, $C_{3-7}$ cycloalkylthio, optionally substituted arylthio or heteroarylthio, $C_{1-8}$ alkoxy, $C_{3-7}$ cycloalkoxy, optionally substituted aryloxy, optionally substituted heteroaryloxy, or optionally substituted aryl or heteroaryl, $C_{3-7}$ cycloalkyl, halo $C_{3-7}$ cycloalkyl, $C_{3-7}$ cycloalkenyl, cyano, COOR¹⁰, CONR¹⁰R¹¹ or NR¹⁰R¹¹, $C_{2-6}$ alkenyl, optionally substituted heterocyclyl, optionally substituted aryl $C_{1-8}$ alkyl, optionally substituted heteroaryl $C_{1-8}$ alkyl in which the alkyl group can be substituted by hydroxy, $R^{10}$ and $R^{11}$ are independently hydrogen, $C_{1-8}$ alkyl, optionally substituted aryl $C_{1-8}$ alkyl, optionally substituted phenyl, or $R^{10}$ and $R^{11}$ together with the nitrogen atom to which they are attached may combine to form a ring with up to six carbon atoms which optionally may be substituted with up to two $C_{1-8}$ alkyl groups or one carbon atom may be replaced by oxygen or sulfur;

$R^{14}$ and $R^{16}$ are independently hydrogen, halo, $C_{1-8}$ alkyl, $C_{3-7}$ cycloalkyl, $C_{3-7}$ cycloalkoxy, halo-$C_{1-8}$ alkyl, halo-$C_{1-8}$ alkoxy, $C_{1-8}$ alkoxy, optionally substituted aryl, or optionally substituted heteroaryl;

$R^{15}$ and $R^{17}$ are independently hydrogen, halo, $C_{1-8}$ alkoxy, $C_{3-7}$-cycloalkyl, $C_{1-8}$ alkyl, $C_{3-7}$ cycloalkoxy, hydroxy, halo $C_{1-8}$ alkoxy, optionally substituted phenyl, optionally substituted phenyl-$C_{1-8}$ alkyl, optionally substituted phenyloxy, optionally substituted phenyl-$C_{1-8}$ alkoxy, tetrahydropyran-2-ylmethoxy, $C_{1-8}$ alkyl-$S(O)_n$—, optionally substituted aryl-$C_{1-8}$ alkyl-$S(O)_n$—, $CH_3(CH_2)_p$—$Z^1$—$(CH_2)_q$—$Z^2$—, or $Z^3$—$(CH_2)_q$—$Z^2$—;

$Z^1$ and $Z^2$ are independently a bond, O, S, SO, $SO_2$, sulphoximino, or $NR^{10}$;

$Z^3$ is hydroxy, protected hydroxy, $NR^{10}R^{11}$, or protected amino, and pharmaceutically acceptable salts and esters thereof, for the treatment of diabetes.

3. A method of using compound of Formula (I):

(I)

in which

X is —O—, —S—, or —$NR^5$—;

$R^5$ is hydrogen, $C_{1-8}$ alkyl, or an amino protecting group;

$R^1$, $R^{1'}$, $R^2$, and $R^3$ are independently hydrogen or $C_{1-8}$ alkyl;

$R^1$ and $R^2$ together form a bond and $R^{1'}$ and $R^3$ are independently hydrogen or $C_{1-8}$ alkyl;

$R^1$ and $R^2$ can combine together with the carbon atoms to which they are attached form a $C_{3-7}$ carbocyclic ring and $R^{1'}$ and $R^3$ are independently hydrogen or $C_{1-8}$ alkyl;

$R^1$ and $R^{1'}$ together with the carbon atom to which they are attached combine to form a $C_{3-7}$ spirocarbocyclic ring and $R^2$ and $R^3$ are independently hydrogen or $C_{1-8}$ alkyl;

$R^2$ and $R^3$ together with the carbon atom to which they are attached combine to form a $C_{3-7}$ spirocarbocyclic and $R^1$ and $R^{1'}$ are independently hydrogen or $C_{1-8}$ alkyl;

n is 0, 1, or 2;

$R^4$ is

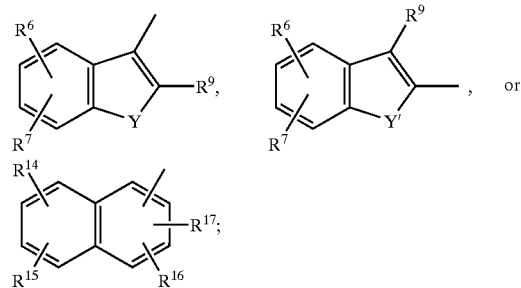

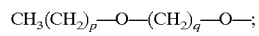

Y is —O—, —S—, or —$NR^8$—;

Y' is —O— or —S—;

$R^6$ and $R^7$ are independently hydrogen, $C_{1-8}$ alkyl, $C_{3-7}$ cycloalkyl, $C_{1-8}$ alkoxy, $C_{1-8}$ alkylthio, halo $C_{1-8}$ alkylthio, $C_{1-8}$ alkylsulfinyl, $C_{1-8}$ alkylsulfonyl, $C_{3-7}$ cycloalkoxy, aryl-$C_{1-8}$ alkoxy, halo, halo-$C_{1-8}$ alkyl, halo-$C_{1-8}$ alkoxy, nitro, —$NR^{10}R^{11}$, —$CONR^{10}R^{11}$, aryl $C_{1-8}$ alkyl, optionally substituted heterocyclyl, optionally substituted phenyl, optionally halo substituted acylamino, cyano, hydroxy, $COR^{12}$, halo $C_{1-8}$ alkylsulfinyl, or halo $C_{1-8}$ alkylsulfonyl, or alkoxyalkyl of the formula $CH_3(CH_2)_p$—O—$(CH_2)_q$—O—;

where p is 0, 1, 2, 3, or 4; and q is 1, 2, 3, 4, or 5;

$R^{12}$ is $C_{1-8}$ alkyl or optionally substituted phenyl;

$R^8$ is hydrogen, $C_{1-8}$ alkyl, halo-$C_{1-8}$ alkyl, optionally substituted phenyl, optionally substituted heterocyclyl, COO $C_{1-8}$ alkyl, optionally substituted COaryl, $COC_{1-8}$ alkyl $SO_2C_{1-8}$ alkyl, optionally substituted SO2 aryl, optionally substituted phenyl-$C_{1-8}$ alkyl, $CH_3(CH_2)_p$—O—$(CH_2)_q$—O—;

$R^9$ is hydrogen, halo, $C_{1-8}$ alkyl, halo $C_{1-8}$ alkyl, $C_{1-8}$ alkylthio, halo $C_{1-8}$alkylthio, $C_{3-7}$ cycloalkylthio, optionally substituted arylthio or heteroarylthio, $C_{1-8}$ alkoxy, $C_{3-7}$ cycloalkoxy, optionally substituted aryloxy, optionally substituted heteroaryloxy, or optionally substituted aryl or heteroaryl, $C_{3-7}$ cycloalkyl, halo $C_{3-7}$ cycloalkyl, $C_{3-7}$ cycloalkenyl, cyano, $COOR^{10}$,$CONR^{10}R^{11}$ or $NR^{10}R^{11}$, $C_{2-6}$ alkenyl, optionally substituted heterocyclyl, optionally substituted aryl $C_{1-8}$ alkyl, optionally substituted heteroaryl $C_{1-8}$ alkyl in which the alkyl group can be substituted by hydroxy, $R^{10}$ and $R^{11}$ are independently hydrogen, $C_{1-8}$ alkyl, optionally substituted aryl $C_{1-8}$ alkyl, optionally substituted phenyl, or $R^{10}$ and $R^{11}$ together with the nitrogen atom to which they are attached may combine to form a ring with up to six carbon atoms which optionally may be substituted with up to two $C_{1-8}$ alkyl groups or one carbon atom may be replaced by oxygen or sulfur;

$R^{14}$ and $R^{16}$ are independently hydrogen, halo, $C_{1-8}$ alkyl, $C_{3-7}$ cycloalkyl, $C_{3-7}$ cycloalkoxy, halo-$C_{1-8}$ alkyl, halo-$C_{1-8}$ alkoxy, $C_{1-8}$ alkoxy, optionally substituted aryl, or optionally substituted heteroaryl;

$R^{15}$ and $R^{17}$ are independently hydrogen, halo, $C_{1-8}$ alkoxy, $C_{3-7}$-cycloalkyl, $C_{1-8}$ alkyl, $C_{3-7}$ cycloalkoxy, hydroxy, halo $C_{1-8}$ alkoxy, optionally substituted phenyl, optionally substituted phenyl-$C_{1-8}$ alkyl, optionally substituted phenyloxy, optionally substituted phenyl-$C_{1-8}$ alkoxy, tetrahydropyran-2-ylmethoxy, $C_{1-8}$ alkyl-$S(O)_n$—, optionally substituted aryl-$C_{1-8}$ alkyl-$S(O)_n$—, $CH_3(CH_2)_p$—$Z^1(CH_2)_q$—$Z^2$—, or $Z^3$—$(CH_2)_q$—$Z^2$—;

$Z^1$ and $Z^2$ are independently a bond, O, S, SO, $SO_2$, sulphoximino, or $NR^{10}$;

$Z^3$ is hydroxy, protected hydroxy, $NR^{10}R^{11}$, or protected amino;

and pharmaceutically acceptable salts and esters thereof, for the treatment of Type II diabetes.

4. A compound according to claim 1 wherein $R^1$ and $R^{1'}$ are hydrogen and $R^2$ and $R^3$ are hydrogen or methyl.

5. A compound according to claim 1 wherein X is —NH—.

6. A compound according to claim 1 wherein n is 0.

7. A compound according to claim 1 wherein $R^4$ is

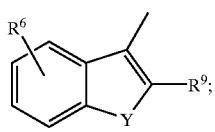

Y is O or S;
$R^6$ is hydrogen, halo, $C_{1-6}$ alkyl, or halo $C_{1-6}$ alkyl; and
$R^9$ is $C_{1-6}$ alkyl or optionally substituted phenyl.

8. A compound according to claim 1 wherein $R^4$ is

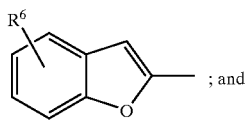

$R^6$ is hydrogen, halo, C1–6 alkyl, or optionally substituted phenyl, naphthyl, or thienyl.

9. A compound according to claim 1 wherein $R^4$ is

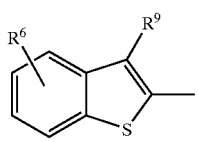

$R^6$ is hydrogen, halo, $C_{1-6}$ alkyl, halo $C_{1-6}$ alkyl, $C_{1-6}$ alkoxy; and $R^9$ is hydrogen, halo, $C_{1-4}$ alkoxy, $C_{1-4}$ alkyl, optionally substituted phenyl, naphthyl, or thienyl, or an optionally substituted phenylmethyl, optionally substituted naphthylmethyl, optionally substituted thienylmethyl, or optionally substituted pyridylmethyl group in which the methyl group is substituted by hydroxy.

10. A compound according to claim 1 wherein $R^4$ is

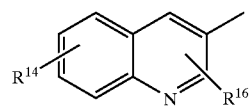

$R^{14}$ is hydrogen, halo, C1–4 alkyl, C1–4 alkoxy, or halo C1–4 alkyl; and $R^{16}$ is C1–4 alkyl, halo C1–4 alkyl, or optionally substituted phenyl.

11. A compound according to claim 1 wherein $R^1$, $R^{1'}$, $R^2$ and $R^3$ are hydrogen or methyl;

X is —NH—; and n is 0.

12. A compound according to claim 11 wherein $R^4$ is

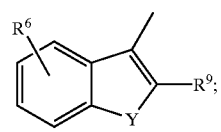

Y is O or S;
$R^6$ is chloro; and
$R^9$ is methyl or 2-chlorophenyl.

13. A compound according to claim 11 wherein $R^4$ is

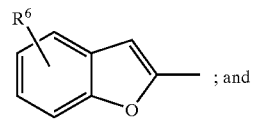

$R^6$ is bromo, phenyl, 4-methylphenyl, 5-chloro-2-thienyl, 2-thienyl, 3-thienyl, 3-trifluoromethylphenyl, 3-methoxyphenyl, 2-methoxyphenyl, 3,5-bistrifluoromethylphenyl, 4-fluorophenyl, or 3-fluorophenyl.

14. A compound according to claim 11 wherein $R^4$ is

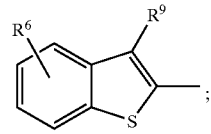

$R^6$ is hydrogen, chloro, bromo, methoxy, methyl, or trifluoromethyl; and $R^9$ is hydrogen, halo, $C_{1-4}$ alkoxy, $C_{1-4}$ alkyl, optionally substituted phenyl, naphthyl, or thienyl, or an optionally substituted phenylmethyl, optionally substituted naphthylmethyl, optionally substituted thienylmethyl, or optionally substituted pyridylmethyl group in which the methyl group is substituted by hydroxy.

15. A compound according to claim 11 wherein R⁴ is

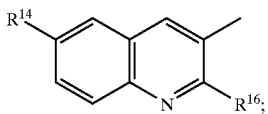

R¹⁴ is chloro, methyl, or trifluoromethyl; and
R¹⁶ is methyl.

16. A compound according to claim 1 wherein
R¹, R¹', R² and R³ are hydrogen or methyl;
X is —NH—;
n is 0, 1, or 2,
R is

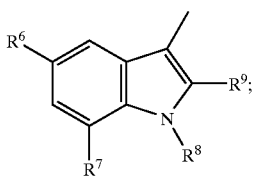

R⁶ is chloro, fluoro, methyl, trifluoromethyl, or pentafluoroethyl;
R⁷ is hydrogen;
R⁸ is hydrogen; and
R⁹ is hydrogen, methyl, benzyl, 3-chlorobenzyl, 4-chlorophenyl, 3-chlorophenyl, 2-chlorophenyl, 3-methylphenyl, 4-chloro-3-methylphenyl, 4-methoxyphenyl, or 2-methoxyphenyl.

17. A compound according to claim 16 wherein n is 0.

18. A compound according to claim 1 which is
3-(4,5-Dihydroimidazol-2-yl)-2,5-dimethyl-1H-indole;
5-Chloro-3-(4,5-dihydroimidazol-2-yl)-2-methyl-1H-indole;
3-(4,5-Dihydroimidazol-2-yl)-2-methyl-5-trifluoromethyl-1H-indole;
3-(4,5-Dihydroimidazol-2-yl)-2-methyl-5-pentafluoroethyl-1H-indole;
5,7-Dichloro-3-(4,5-dihydroimidazol-2-yl)-2-methyl-1H-indole;
3-(4,5-Dihydroimidazol-2-yl)-5-fluoro-2-methyl-1H-indole;
3-(4,5-Dihydroimidazol-2-yl)-2-methyl-5-nitro-1H-indole;
5-Bromo-3-(4,5-dihydroimidazol-2-yl)-2-methyl-1H-indole;
5-Chloro-3-(4,5-dihydroimidazol-2-yl)-2-phenyl-1H-indole;
5,7-Dichloro-3-(4,5-dihydroimidazol-2-yl)-2-phenyl-1H-indole;
5-Chloro-3-(4,5-dihydroimidazol-2-yl)-7-methyl-2-phenyl-1H-indole;
5-Chloro-2-(4-chlorophenyl)-3-(4,5-dihydroimidazol-2-yl)-1H-indole;
5-Chloro-2-(3-chlorophenyl)-3-(4,5-dihydroimidazol-2-yl)-1H-indole;
5-Chloro-2-(2-chlorophenyl)-3-(4,5-dihydroimidazol-2-yl)-1H-indole;
2-(4-Chlorophenyl)-5,7-dichloro-3-(4,5-dihydroimidazol-2-yl)-1H-indole;
2-(2-Chlorophenyl)-3-(4,5-dihydroimidazol-2-yl)-5-fluoro-1H-indole;
2-(2-Bromophenyl)-5-chloro-3-(4,5-dihydroimidazol-2-yl)-1H-indole;
5-Chloro-3-(4,5-dihydroimidazol-2-yl)-2-(3-fluorophenyl)-1H-indole;
5-Chloro-3-(4,5-dihydroimidazol2-y)-2-(4-iodophenyl)-1H-indole;
5-Chloro-3-(4,5-dihydroimidazol-2-yl)-2-(4-methylphenyl)-1H-indole;
5-Chloro-3-(4,5-dihydroimidazol-2-yl)-2-(3-methylphenyl)-1H-indole;
5,7-Dichloro-3-(4,5-dihydroimidazol-2-yl)-2-(3-methylphenyl)-1H-indole;
5-Chloro-3-(4,5-dihydroimidazol-2-yl)-2-(2-methylphenyl)-1H-indole;
5-Chloro-3-(4,5-dihydroimidazol-2-y)-2-(2-trifluoromethylphenyl)-1H-indole;
2-(2,4-Dichlorophenyl)-3-(4,5-dihydroimidazol-2-yl)-5-fluoro-1H-indole;
3-(4,5-Dihydroimidazol-2-yl)-2-(2,4-dimethylphenyl)-5-fluoro-1H-indole;
5-Chloro-3-(4,5-dihydroimidazol-2-yl)-2-(2,4-dimethylphenyl)-1H-indole;
5-Chloro-3-(4,5-dihydroimidazol-2-yl)-2-(2,5-dimethylphenyl)-1H-indole;
5-Chloro-3-(4,5-dihydroimidazol-2-yl)-2-(2-methoxyphenyl)-1H-indole;
5-Chloro-3-(4,5-dihydroimidazol-2-yl)-2-(4-methoxyphenyl)-1H-indole;
5-Chloro-2-(4-chloro-3-methylphenyl)-3-(4,5-dihydroimidazol-2-yl)-1H-indole;
5-Chloro-3-(4,5-dihydroimidazol-2-yl)-2-(4-(2-methoxyethoxy)phenyl)-1H-indole;
5-Chloro-3-(4,5-dihydroimidazol-2-yl)-2-(2-(2-methoxyethoxy)phenyl)-1H-indole;
5-Chloro-3-(4,5-dihydroimidazol-2-yl)-1H-indole;
5-Chloro-2-cyclohexyl-3-(4,5-dihydroimidazol-2-yl)-1H-indole;
5-Chloro-2-(cyclohexen-1-yl)-3-(4,5-dihydroimidazol-2-yl)-1H-indole;
2,5-Bistrifluoromethyl-3-(4,5-dihydroimidazol-2-yl)-1H-indole;
2-Benzyl-5-chloro-3-(4,5-dihydroimidazol-2-yl)-1H-indole;
5-Chloro-2-(2-chlorobenzyl)-3-(4,5-dihydroimidazol-2-yl)-1H-indole;
5-Chloro-2-(3-chlorobenzyl)-3-(4,5-dihydroimidazol-2-yl)-indole;
5-Chloro-2-(2-chlorobenzyl)-3-(4,5-dihydroimidazol-2-yl)-2-methyl-1H-indole;
5-Chloro-3-(4,5-dihydro-4,4-dimethylimidazol-2-yl)-2-methyl-1H-indole;
5-Chloro-2-(2-chlorophenyl)-3-(4,5-dihydro-4,4-dimethylimidazol-2-yl)-1H-indole;
5-Chloro-3-(4,5-dihydroimidazol-2-yl)-2-(pyridin4-yl)-1H-indole;
5-Chloro-3-(4,5-dihydroimidazol-2-yl)-2-(3-thienyl)-1H-indole;
5-Chloro-3-(4,5-dihydroimidazol-2-yl)-2-(2,5-dimethyl-3-thienyl)-1H-indole;
5-Chloro-3-(4,5-dihydroimidazol-2-yl)-2-(3-methyl-2-thienyl)-1H-indole;
2-[2-(2-(2-Fluorophenyl)indol-3-yl)ethyl]-4,5-dihydroimidazole; or
2-[2-(2-(2-Chlorophenyl)indol-3-yl)ethyl4,5-dihydroimidazole;
or a pharmaceutically acceptable salt or ester thereof.

19. A compound according to claim 1 which is
2-[5-Chloro-2-(2-chlorophenyl)benzofuran-3-yl]-4,5-dihydro-1H-imidazole;

2-[5-Chloro-2-(3-chlorophenyl)benzofuran-3-yl]-4,5-dihydro-1H-imidazole;
2-[5-Chloro-2-methylbenzofuran-3-yl]-4,5-dihydro-1H-imidazole; or
2-[5-Fluoro-2-methylbenzofuran-3-yl]-4,5-dihydro-1H-imidazole;
or a pharmaceutically acceptable salt or ester thereof.

20. A compound according to claim 1 which is
2-[2-(2-Chlorophenyl)-5-fluorobenzo[b]thiophen-3-yl]-4,5-dihydro-1H-imidazole;
2-[5-Fluoro-2-(4-methylphenyl)benzo[b]thiophen-3-yl]-4,5-dihydro-1H-imidazole; or
2-(5-Chloro-2-methylbenzo[b]thiophen-3-yl)-4,5-dihydro-4,4-dimethyl-1H-imidazole;
or a pharmaceutically acceptable salt or ester thereof.

21. A compound according to claim 1 which is
6-Chloro-3-(4,5-dihydro-1H-imidazol-2-yl)-3-methylquinoline; or
3-(4,5-Dihydro-1H-imidazol-2-yl)-3-phenylquinoline;
or a pharmaceutically acceptable salt or ester thereof.

22. A compound according to claim 1 which is
2-(3-Phenylbenzo[b]thiophen-2-yl)-4,5-dihydro-1H-imidazole;
2-(3-Butoxybenzo[b]thiophen-2-yl)-4,5-dihydro-1H-imidazole;
(2-(4,5-Dihydro-1H-imidazol-2-yl)benzo[b]thiophen-3-yl)-(naphthalen-1-yl)methanol; or
(4-tert.-Butylphenyl)-(2-(4,5-dihydro-1H-imidazol-2-yl)benzo[b]thiophen-3-yl)methanol;
or a pharmaceutically acceptable salt or ester thereof.

23. A compound according to claim 1 which is
2-(5-Phenylbenzofuran-2-yl)-4,5-dihydro-1H-imidazole;
2-(5-(3,5-Bistrifluoromethylphenyl)benzofuran-2-yl)-4,5-dihydro-1H-imidazole;
2-(5-(4-Fluorophenyl)benzofuran-2-yl)-4,5-dihydro-1H-imidazole;
2-(5-(4-Methylphenyl)benzofuran-2-yl)-4,5-dihydro-1H-imidazole;
2-(5-(3-Thienyl)benzofuran-2-yl)-4,5-dihydro-1H-imidazole;
2-(5-(3-Fluorophenyl)benzofuran-2-yl)-4,5-dihydro-1H-imidazole;
2-(5-(3-Trifluoromethylphenyl)benzofuran-2-yl)-4,5-dihydro-1H-imidazole;
2-(5-(2-Thienyl)benzofuran-2-yl)-4,5-dihydro-1H-imidazole;
2-(5-(5-Chloro-2-thienyl)benzofuran-2-yl)-4,5-dihydro-1H-imidazole;
2-(5-(3-Methoxyphenyl)benzofuran-2-yl)-4,5-dihydro-1H-imidazole;
2-(5-(2-Methoxyphenyl)benzofuran-2-yl)-4,5-dihydro-1H-imidazole;
2-(7-(4-Methylphenyl)benzofuran-2-yl)-4,5-dihydro-1H-imidazole;
2-(7-(3-Thienyl)benzofuran-2-yl)-4,5-dihydro-1H-imidazole;
2-(7-(2-Thienyl)benzofuran-2-yl)-4,5-dihydro-1H-imidazole; or
2-(4-(5-Chloro-2-thienyl)benzofuran-2-yl)-4,5-dihydro-1H-imidazole;
or a pharmaceutically acceptable salt or ester thereof.

24. A compound according to claim 1 which is
5-Chloro-3-(4,5-dihydroimidazol-2-yl)-2-methyl-1H-indole;
or a pharmaceutically acceptable salt or ester thereof.

25. A compound according to claim 1 which is
6-Chloro-3-(4,5-dihydro-1H-imidazol-2-yl)-3-methylquinoline
or a pharmaceutically acceptable salt or ester thereof.

26. A compound according to claim 1 which is
2-[3-(2-Methoxyethoxy)-7-(4-methylphenyl)naphthalen-2-yl]-4,5-dihydro-1H-imidazole;
or a pharmaceutically acceptable salt or ester thereof.

27. A compound according to claim 1 which is
3-(4,5-Dihydroimidazol-2-yl)-2-methyl-5-trifluoromethyl-1H-indole;
or a pharmaceutically acceptable salt or ester thereof.

28. A compound according to claim 1 which is
5-Chloro-2-(3-chlorophenyl)-3-(4,5-dihydroimidazol-2-yl)-1H-indole;
or a pharmaceutically acceptable salt or ester thereof.

29. A compound according to claim 1 which is
5-Chloro-2-(2-chlorophenyl)-3-(4,5-dihydroimidazol-2-yl)-1H-indole;
or a pharmaceutically acceptable salt or ester thereof.

30. A pharmaceutical formulation comprising as an active ingredient a compound of Formula I as claimed in claim 1, or a pharmaceutically acceptable salt or ester thereof, together with one or more pharmaceutically acceptable carriers, diluents or excipients.

31. A method of treating a mammal for diabetes, diabetic complications, metabolic disorders, or related diseases where impaired glucose disposal is present, which comprises administering to said mammal a therapeutically effective amount of a compound of Formula I, according to claim 1.

32. A method of treating a mammal for diabetes, diabetic complications, metabolic disorders, or related diseases where impaired glucose disposal is present, which comprises administering to said mammal a therapeutically effective amount of a formulation according to claim 30.

33. A method of treating a mammal for diabetes, which comprises administering to said mammal a therapeutically effective amount of a compound of Formula I, according to claim 1.

34. A method of treating a mammal for diabetes, which comprises administering to said mammal a therapeutically effective amount of a formulation according to claim 30.

35. A method for stimulating insulin secretion in a mammal in need thereof comprising administering to said mammal a therapeutically effective amount of a compound of Formula I, according to claim 1.

36. A method for stimulating insulin secretion in a mammal in need thereof comprising administering to said mammal a therapeutically effective amount of a formulation according to claim 30.

37. A method of using a compound of Formula I, according to claim 1, for the treatment of a mammal for diabetes, diabetic complications, metabolic disorders, or related diseases where impaired glucose disposal is present.

38. A formulation for the treatment of a mammal for diabetes, diabetic complications, metabolic disorders, or related diseases where impaired glucose disposal is present, comprising as an active ingredient a compound of Formula I as claimed in claim 1, or a pharmaceutically acceptable salt or ester thereof, together with one or more pharmaceutically acceptable carriers, diluents or excipients.

* * * * *